(12) United States Patent
Milosevic et al.

(10) Patent No.: US 12,331,095 B2
(45) Date of Patent: Jun. 17, 2025

(54) INDUCIBLE T CELL RECEPTORS AND USES THEREOF

(71) Applicant: MEDIGENE IMMUNOTHERAPIES GMBH, Planegg-Martinsried (DE)

(72) Inventors: Slavoljub Milosevic, Munich (DE); Adriana Turqueti Neves, Olching (DE); Kristina Schoedel, Munich (DE); Alexander Schmidt, Zangberg (DE)

(73) Assignee: MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 1221 days.

(21) Appl. No.: 16/980,345

(22) PCT Filed: Mar. 13, 2019

(86) PCT No.: PCT/EP2019/056228
§ 371 (c)(1),
(2) Date: Sep. 11, 2020

(87) PCT Pub. No.: WO2019/175209
PCT Pub. Date: Sep. 19, 2019

(65) Prior Publication Data
US 2021/0038647 A1 Feb. 11, 2021

(30) Foreign Application Priority Data
Mar. 14, 2018 (EP) .................................... 18161766

(51) Int. Cl.
| | |
|---|---|
| *C07K 14/725* | (2006.01) |
| *A61K 31/138* | (2006.01) |
| *A61K 40/11* | (2025.01) |
| *A61K 40/32* | (2025.01) |
| *A61K 40/42* | (2025.01) |
| *C12N 15/86* | (2006.01) |

(52) U.S. Cl.
CPC ........ *C07K 14/7051* (2013.01); *A61K 31/138* (2013.01); *A61K 40/11* (2025.01); *A61K 40/32* (2025.01); *A61K 40/4269* (2025.01); *A61K 40/427* (2025.01); *C12N 15/86* (2013.01); *C12N 2799/027* (2013.01)

(58) Field of Classification Search
None
See application file for complete search history.

(56) References Cited

U.S. PATENT DOCUMENTS

2010/0068186 A1* 3/2010 Jakobsen ........... C07K 14/7051
435/325

FOREIGN PATENT DOCUMENTS

| WO | 2005113595 | A2 | 12/2005 | |
|---|---|---|---|---|
| WO | WO-2014127261 | A1 * | 8/2014 | ........... A61K 35/17 |
| WO | 2017/158116 | A1 | 9/2014 | |
| WO | 2016/098078 | A2 | 6/2016 | |
| WO | 2016/135470 | A1 | 9/2016 | |
| WO | 2019175209 | A1 | 9/2019 | |

OTHER PUBLICATIONS

International Search Report issued May 17, 2019 in PCT/EP2019/056228 (5 pages).
"Anti-human TCR alpha chain R10P1A7 constant region (TRAC) Seq ID No. 9.", XP002784602, retrieved from EBI accession No. GSP:BEI46378, Database accession No. BEI46378 sequence, Nov. 2, 2017.
"Anti-human TCR beta chain R10P1A7 constant region (TRBC2) Seq ID No. 17.", XP002784603, retrieved from EBI accession No. GSP:BEI46386 Database accession No. BEI46386 sequence, Nov. 2, 2017.
Reuss et al., "TCR-engi neered T cells: A model of inducible TCR expression to dissect the interrelationship between two TC Rs : Molecular immunology", European Journal of Immunology, vol. 44, No. 1, Oct. 20, 2013, pp. 265-274.
Chenqi Xu et al., "A Membrane-proximal Tetracysteine Motif Contributes to Assembly of CD3[delta] [epsilon] and CD3[gamma] [epsilon] Dimers with the T Cell Receptor", Journal of Biological Chemistry, vol. 281, No. 48, Dec. 1, 2006 (Dec. 1, 2006), pp. 36977-36984.
Felker et al., "In Vivo Performance and Properties of Tamoxifen Metabolites for CreERT2 Control", Plos One, vol. 11, No. 4, Apr. 14, 2016 (Apr. 14, 2016) , p. e0152989, XP055501858, DOI: 10.1371/journal.pone.0152989 abstract.
Written Opinion issued May 17, 2019 in PCT/EP2019/056228 (9 pages).
Ballister et al., Localized light-induced protein dimerization in living cells using a photocaged dimerizer. Nat Commun. Nov. 17, 2014;5:5475.
Ballister, Inducible Protein Dimerization: New Tools and Applications to Understanding the Mitotic Checkpoint. Publicly Accessible Penn Dissertations, University of Pennsylvania Scholarly Commons. 2014:118 pages.
Belshaw et al., Controlling protein association and subcellular localization with a synthetic ligand that induces heterodimerization of proteins. Proc Natl Acad Sci USA. May 14, 1996;93(10):4604-4607.
Call et al., The Organizing Principle in the Formation of the T Cell Receptor-CD3 Complex. Cell. Dec. 27, 2002;111(7):967-979.
Erhart et al., Chemical Developmentof Intracellular Protein Heterodimerizers. Chem Biol. Apr. 18, 2013;20(4):549-557.

(Continued)

Primary Examiner — Christopher M Babic
Assistant Examiner — Kimberly A Aron
(74) Attorney, Agent, or Firm — Michael A. Whittaker

(57) ABSTRACT

Combinations comprising one or more nucleic acid molecules comprising a nucleic acid sequence A encoding for a TCR alpha chain linked to a dimerization domain, and a nucleic acid sequence B encoding for a TCR beta chain linked to a dimerization domain, as well as proteins encoded by such nucleic acid molecules and corresponding uses and methods.

19 Claims, 25 Drawing Sheets

Specification includes a Sequence Listing.

(56) References Cited

OTHER PUBLICATIONS

Farrar et al., Coumermycin-Induced Dimerization of GyrB-Containing Fusion Proteins. Methods Enzymol. 2000;327:421-429.
Feil et al., Regulation of Cre Recombinase Activity by Mutated Estrogen Receptor Ligand-Binding Domains. Biochem Biophys Res Commun. Aug. 28, 1997;237(3):752-757.
Glusman et al., Comparative Genomics of the Human and Mouse T Cell Receptor Loci. Immunity. Sep. 2001;15(3):337-349.
Ho et al., Dimeric ligands define a role for transcriptional activation domains in reinitiation. Nature. Aug. 29, 1996;382(6594):822-826.
Lefranc, Unique database numbering system for immunogenetic analysis. Immunol Today. Nov. 1997;18(11):509.
Milosevic et al., Identification of Major Histocompatibility Complex Class II-Restricted Antigens and Epitopes of the Epstein-Barr Virus by a Novel Bacterial Expression Cloning Approach. J Virol. Nov. 2006;80(21):10357-10364.
Miyamato et al., Rapid and Orthogonal Logic Gating with a Gibberellin-induced Dimerization System. Nat Chem Biol. Mar. 25, 2012;8(5):465-470.

* cited by examiner

Figure 11

Alignment of alleles: Human TRAC

The nucleitide between parantheses at the beginning of exons comes from a DONOR-SPLICE (n from ngt). The first nucleotide from an INT-DONOR-SPLICE is underlines (n from ngt).

Exon names are shown between parantheded on the first line.
Cysteine involved in the disulfide bridge are shown in bright grey.
STOP-CODON is indicated by an asterisk.

When several alleles are shown, the nucleotide mutation and amino acid changes for a given codon are indicated in brighter grey letters.
Dashes indicate identical nucleotides. Dots indicate gaps by comparison to the longest sequence. Blankd indicate partial sequences (blanks at the 5' and/or 3' end).

First codon and amino acid position 1.3 depends on the last nucleotide of the TRA-J-REGION (Alignment of alleles: Human (*Homo sapiens*) TRAJ). This amino acid my be an N (aat), H (cat), D (gat) or Y (tat).

```
                                            1.3 1.2 1.1  1   2   3   4   5   6   7   8   9  10  11
                                             N   I   Q   N   P   D   P   A   V   Y   Q   L   R   D
    X02883  ,TRAC*01 (EX1)                 (A)AT ATC CAG AAC CCT GAC CCT GCC GTG TAC CAG CTG AGA GAC
    X02592  ,TRAC*01,(cDNA)                (-)-- --- --- --- --- --- --- --- --- --- --- --- --- ---
    M14859  ,TRAC*01                       (-)-- --- --- --- --- --- --- --- --- --- --- --- --- ---
    AE000662,TRAC*01                       (-)-- --- --- --- --- --- --- --- --- --- --- --- --- ---
    M94081  ,TRAC*01                       (-)-- --- --- --- --- --- --- --- --- --- --- --- --- ---

_____AB_____
                                    15.1    15.3
                     12  13  14  15  15.2    16  17  18  19  20  21  22  23  24  25  26  27  28
                      S   K                   S   S   D   K   S   V   C   L   F   T   D   F
    X02883  ,TRAC*01 (EX1)  TCT AAA ... ... ... ... ... ... TCC AGT GAC AAG TCT GTC TGC CTA TTC ACC GAT TTT
    X02592  ,TRAC*01,(cDNA) --- --- ... ... ... ... ... ... --- --- --- --- --- --- --- --- --- --- --- ---
    M14859  ,TRAC*01        --- --- ... ... ... ... ... ... --- --- --- --- --- --- --- --- --- --- --- ---
    AE000662,TRAC*01        --- --- ... ... ... ... ... ... --- --- --- --- --- --- --- --- --- --- --- ---
    M94081  ,TRAC*01        --- --- ... ... ... ... ... ... --- --- --- --- --- --- --- --- --- --- --- ---

_____BC_____                               _____CD_____
                                                                                   45.1   45.3    45.5
                     29  30  31  32  33  34  35  36  39  40  41  42  43  44  45   45.2    45.4
                      D   S               Q   T   N   V   S   Q   S   K   D   S
    X02883  ,TRAC*01 (EX1)   GAT TCT ... ... ... CAA ACA AAT GTG TCA CAA AGT AAG GAT TCT ... ... ... ... ...
    X02592  ,TRAC*01,(cDNA)  --- --- ... ... ... --- --- --- --- --- --- --- --- --- --- ... ... ... ... ...
    M14859  ,TRAC*01         --- --- ... ... ... --- --- --- --- --- --- --- --- --- --- ... ... ... ... ...
    AE000662,TRAC*01         --- --- ... ... ... --- --- --- --- --- --- --- --- --- --- ... ... ... ... ...
    M94081  ,TRAC*01         --- --- ... ... ... --- --- --- --- --- --- --- --- --- --- ... ... ... ... ...
```

Figure 11 continued

```
AE000662,TRAC*01                     --- ---  ...  ...  ...  --- --- --- --- --- --- --- --- --- ---  ...  ...  ...  ...  ...
M94081  ,TRAC*01                     --- ---  ...  ...  ...  --- --- --- --- --- --- --- --- --- ---  ...  ...  ...  ...  ...
                                                                                                                         DE
                                          45.7                                      84.1     84.3     84.5     84.7      85.6
                                     45.6      77  78  79  80  81  82  83  84    84.2     84.4     84.6     85.7      85.5
                                                D   V   Y   I   T   D   K   T   V   L   D   M   R   S               M   D
X02883  ,TRAC*01 (EX1)               ... ... GAT GTG TAT ATC ACA GAC AAA ACT GTG CTA GAC ATG AGG TCT ... ... ATG GAC
X02592  ,TRAC*01,(cDNA)              ... ... --- --- --- --- --- --- --- --- --- --- --- --- --- --- ... ... --- ---
M14858  ,TRAC*01                     ... ... --- --- --- --- --- --- --- --- --- --- --- --- --- --- ... ... --- ---
AE000662,TRAC*01                     ... ... --- --- --- --- --- --- --- --- --- --- --- --- --- --- ... ... --- ---
M94081  ,TRAC*01                     ... ... --- --- --- --- --- --- --- --- --- --- --- --- --- --- ... ... --- ---
                                                                                                                EF
                                      85.4    85.2                                                              96.1
                                          85.3   85.1  85  86  87  88  89  90  91  92  93  94  95  96   96.2  97  98
                                           F    K   S   N   S   A   V   A   W   S   N   K   S
X02883  ,TRAC*01 (EX1)               TTC AAG AGC AAC AGT GCT GTG GCC TGG AGC AAC AAA TCT ... ... ... ... ... ...
X02592  ,TRAC*01,(cDNA)              --- --- --- --- --- --- --- --- --- --- --- --- --- ... ... ... ... ... ...
M14858  ,TRAC*01                     --- --- --- --- --- --- --- --- --- --- --- --- --- ... ... ... ... ... ...
AE000662,TRAC*01                     --- --- --- --- --- --- --- --- --- --- --- --- --- ... ... ... ... ... ...
M94081  ,TRAC*01                     --- --- --- --- --- --- --- --- --- --- --- --- --- ... ... ... ... ... ...
                                                                                              FG
                                      99 100 101 102 103 104 105 106 107 108 109 110 111 112 113 114 115 116 117 118
                                          D   F   A   C   A   N   A   F   N   N               S   I   I   P   E   D
X02883  ,TRAC*01 (EX1)               ... ... GAC TTT GCA TGT GCA AAC GCC TTC AAC AAC ... ... AGC ATT ATT CCA GAA GAC
X02592  ,TRAC*01,(cDNA)              ... ... --- --- --- --- --- --- --- --- --- --- ... ... --- --- --- --- --- ---
M14858  ,TRAC*01                     ... ... --- --- --- --- --- --- --- --- --- --- ... ... --- --- --- --- --- ---
AE000662,TRAC*01                     ... ... --- --- --- --- --- --- --- --- --- --- ... ... --- --- --- --- --- ---
M94081  ,TRAC*01                     ... ... --- --- --- --- --- --- --- --- --- --- ... ... --- --- --- --- --- ---

119 120 121 122 123 124
                                       T   F   F   P   S   P
X02883  ,TRAC*01 (EX1)               ACC TTC TTC CCC AGC CCA G
X02592  ,TRAC*01,(cDNA)              --- --- --- --- --- --- -
M14858  ,TRAC*01                     --- --- --- --- --- --- -
AE000662,TRAC*01                     --- --- --- --- --- --- -
M94081  ,TRAC*01                     --- --- --- --- --- --- -
```

Figure 11 continued

```
                                      1   2   3   4   5   6   7   8   9   10  11  12  13  14  15
                                      E   S   S   C   D   V   K   L   V   E   K   S   F   E   T
X02883  ,TRAC*01 (EX2)                AA  AGT TCC TGT GAT GTC AAG CTG GTC GAG AAA AGC TTT GAA ACA G

X02592  ,TRAC*01,(cDNA)               --  --- --- --- --- --- --- --- --- --- --- --- --- --- --- -

M14859  ,TRAC*01                      --  --- --- --- --- --- --- --- --- --- --- --- --- --- --- -

AE000662,TRAC*01                      --  --- --- --- --- --- --- --- --- --- --- --- --- --- --- -

M94081  ,TRAC*01                      --  --- --- --- --- --- --- --- --- --- --- --- --- --- --- -

1   2   3   4   5   6   7   8   9   10  11  12  13  14  15  16  17  18  19  20
                                      D   T   N   L   N   F   Q   N   L   S   V   I   G   F   R   I   L   L   L   K
X02883  ,TRAC*01 (EX3)                AT  ACG AAC CTA AAC TTT CAA AAC CTG TCA GTG ATT GGG TTC CGA ATC CTC CTC CTG AAA

X02592  ,TRAC*01,(cDNA)               --  --- --- --- --- --- --- --- --- --- --- --- --- --- --- --- --- --- --- ---

M14860  ,TRAC*01                      --  --- --- --- --- --- --- --- --- --- --- --- --- --- --- --- --- --- --- ---

AE000662,TRAC*01                      --  --- --- --- --- --- --- --- --- --- --- --- --- --- --- --- --- --- --- ---

M94081  ,TRAC*01                      --  --- --- --- --- --- --- --- --- --- --- --- --- --- --- --- --- --- --- ---

21  22  23  24  25  26  27  28  29  30  31  32  33  34  35  36
                                      V   A   G   F   N   L   L   M   T   L   R   L   W   S   S   *
X02883  ,TRAC*01 (EX3)                GTG GCC GGG TTT AAT CTG CTC ATG ACG CTG CGG CTG TGG TCC AGC TGA G

X02592  ,TRAC*01,(cDNA)               --- --- --- --- --- --- --- --- --- --- --- --- --- --- --- --- -

M14860  ,TRAC*01                      --- --- --- --- --- --- --- --- --- --- --- --- --- --- --- --- -

AE000662,TRAC*01                      --- --- --- --- --- --- --- --- --- --- --- --- --- --- --- --- -

M94081  ,TRAC*01                      --- --- --- --- --- --- --- --- --- --- --- --- --- --- --- --- -
```

Figure 12

Alignment of alleles: human (*Homo sapiens*) TRBC1

When several alleles are shown, the nucleotides and amino acid changes for a given codon are indicated in brighter grey. These polymorphic mutations are reported in Tables of alleles.
Dashes indicate identical nucleotides. Dots indicate gaps according to the IMGT unique numbering.
Blanks indicate partial sequences (blanks at the 5' and/or 3' end).
- Dots indicate gaps according to the IMGT unique numbering.
- Blanks at the 5' and/or 3' end indicate partial sequences.
- Asterisk (*) in the sequence indicate a STOP-CODON.
- Letters in brighter grey correspond to amino acids which are polymorphic in the other alleles.
- Letters in bold correspond to additional positions in the IMGT unique numbering.
- N (Asn, asparagin) of potential N-glycosylation sites (NXS/T, where X is different from P), (N-linked glycosylation) is shown in brighter grey.

The nucleitide between parantheses at the beginning of exons comes from a DONOR-SPLICE (n from ngt). The first nucleotide from an INT-DONOR-SPLICE is underlines (n from ngt).

Exon names are shown between parantheded on the first line.
Cysteine involved in the disulfide bridge are shown in bright grey.
STOP-CODON is indicated by an asterisk.

When several alleles are shown, the nucleotide mutation and amino acid changes for a given codon are indicated in brighter grey letters.
Dashes indicate identical nucleotides. Dots indicate gaps by comparison to the longest sequence.
Blankd indicate partial sequences (blanks at the 5' and/or 3' end).

Figure 12 continued (1)

```
                                       1.8 1.7 1.6 1.5 1.4 1.3 1.2 1.1  1   2   3   4   5   6   7   8   9  10  11  12
                                        E   D   L   N   K   V   F   P   P   E   V   A   V   F   E   P   S   E   A
M12887      TRBC1*01 F EX1 gDNA        gag gac ctg aac aag gtg ttc cca ccc gag gtc gct gtg ttt gag cca tca gaa gca M14157      TRBC1*01 F EX1 gDNA         -- --- --- --- --- --- --- --- --- --- --- --- --- --- --- --- --- --- ---

L36092(1)   TRBC1*02 F EX1 gDNA        --- --- --- --- --- --- --- --- --- --- --- --- --- --- --- --- --- --- ---

IMGT000021  TRBC1*03 F EX1 gDNA        --- --- --- --- --- --- --- --- --- --- --- --- --- --- --- --- --- --- ---

AB
                                                     15.1    15.3
                                        13  14  15        15.2     16  17  18  19  20  21  22  23  24  25  26  27  28  29
                                         E   I   S    H              T   Q   K   A   T   L   V   C   L   A   T   G   F   F
M12887      TRBC1*01 F EX1 gDNA         gag atc tcc  cac ... ...    acc caa aag gcc aca ctg gtg tgc ctg gcc aca ggc ttc ttc M14157      TRBC1*01 F EX1 gDNA         --- --- ---  --- ... ...    --- --- --- --- --- --- --- --- --- --- --- --- --- ---

L36092(1)   TRBC1*02 F EX1 gDNA         --- --- ---  --- ... ...    --- --- --- --- --- --- --- --- --- --- --- --- --- ---

IMGT000021  TRBC1*03 F EX1 gDNA         --- --- ---  --- ... ...    --- --- --- --- --- --- --- --- --- --- --- --- --- ---

BC                                                          CD
                                                                                                       45.1    45.3    45.5
                                        30  31  34  35  36  37  38  39  40  41  42  43  44  45       45.2    45.4    45.6
                                         P           D   H   V   E   L   S   W   W   V   N   G   K   E   V   H   S
M12887      TRBC1*01 F EX1 gDNA         ccc ... ... gac cac gtg gag ctg agc tgg tgg gtg aat ggg aag gag gtg cac agt ...

M14157      TRBC1*01 F EX1 gDNA         --- ... ... --- --- --- --- --- --- --- --- --- --- --- --- --- --- --- --- ...

L36092(1)   TRBC1*02 F EX1 gDNA         --- ... ... --- --- --- --- --- --- --- --- --- --- --- --- --- --- --- --- ...

IMGT000021  TRBC1*03 F EX1 gDNA         --t ... ... --- --- --- --- --- --- --- --- --- --- --- --- --- --- --- --- ...

DE
                                        45.7                              84.1    84.3    84.5    84.7    85.6    85.4
                                         77  78  79  80  81  82  83  84      84.2    84.4    84.6    85.7    85.5
                                          G   V   S   T   D   P   Q   P   L   K   E   Q   P   A   L       N   D   S
M12887      TRBC1*01 F EX1 gDNA         ... ggg gtc agc acg gac ccg cag ccc ctc aag gag cag ccc gcc ctc ... aat gac tcc M14157      TRBC1*01 F EX1 gDNA         ... --- --- --- --- --- --- --- --- --- --- --- --- --- --- --- ... --- --- ---

L36092(1)   TRBC1*02 F EX1 gDNA         ... --- --- --- --- --a --- --- --- --- --- --- --- --- --- --- ... --- --- ---

IMGT000021  TRBC1*03 F EX1 gDNA         ... --- --- --- --- --- --- --- --- --- --- --- --- --- --- --- ... --- --- ---
```

Figure 12 continued (2)

```
                                                                                                              EF
                                      _____85.2_____                                                      __96.1__
                                     85.3     85.1 85  86  87  88  89  90  91  92  93  94  95  96    96.2 97  98  99
                                      R   Y    C   L   S   S   R   L   R   V   S   A   T   F   W  Q    N   P   R
M12887    TRBC1*01 F EX1 gDNA        aga tac  tgc ctg agc agc cgc ctg agg gtc tcg gcc acc ttc tgg cag ... aac ccc cgc M14157    TRBC1*01 F EX1 gDNA        --- ---  --- --- --- --- --- --- --- --- --- --- --- --- --- --- ... --- --- ---

L36092(1) TRBC1*02 F EX1 gDNA        --- ---  --- --- --- --- --- --- --- --- --- --- --- --- --- --- ... --- --- ---

IMGT000021 TRBC1*03 F EX1 gDNA       --- ---  --- --- --- --- --- --- --- --- --- --- --- --- --- --- ... --- --- ---

_____FG_____
                                     100 101 102 103 104 105 106 107 108 109 110 111 111.111.111.111.111.111.112 112.
                                      N   H   F   R   C   Q   V   Q   F   Y   G   L   S   E   N   D   E   W   T   Q
M12887    TRBC1*01 F EX1 gDNA        aac cac ttc cgc tgt caa gtc cag ttc tac ggg ctc tcg gag aat gac gag tgg acc cag M14157    TRBC1*01 F EX1 gDNA        --- --- --- --- --- --- --- --- --- --- --- --- --- --- --- --- --- --- --- ---

L36092(1) TRBC1*02 F EX1 gDNA        --- --- --- --- --- --- --- --- --- --- --- --- --- --- --- --- --- --- --- ---

IMGT000021 TRBC1*03 F EX1 gDNA       --- --- --- --- --- --- --- --- --- --- --- --- --- --- --- --- --- --- --- ---

_____
                                     112.112.112.112.112.113 114 115 116 117 118 119 120 121 122 123 124 125
                                      D   R   A   K   P   V   T   Q   I   V   S   A   E   A   W   G   R   A
M12887    TRBC1*01 F EX1 gDNA        gat agg gcc aaa ccc gtc acc cag atc gtc agc gcc gag gcc tgg ggt aga gca g M14157    TRBC1*01 F EX1 gDNA        --- --- --- --- --- --- --- --- --- --- --- --- --- --- --- --- --- --- -

L36092(1) TRBC1*02 F EX1 gDNA        --- --- --- --- --- --- --- --- --- --- --- --- --- --- --- --- --- --- -

IMGT000021 TRBC1*03 F EX1 gDNA       --- --- --- --- --- --- --- --- --- --- --- --- --- --- --- --- --- --- -

1   2   3   4   5   6
                                      D   C   G   F   I   S
M12887    TRBC1*01 F EX2 gDNA        gac tgt ggc ttt acc tcg g M14157    TRBC1*01 F EX2 gDNA        --- --- --- --- --- --- -

L36092(1) TRBC1*02 F EX2 gDNA        --- --- --- --- --- --- -

IMGT000021 TRBC1*03 F EX2 gDNA       --- --- --- --- --- --- -
```

Figure 12 continued (3)

|  |  | | 1<br>V | 2<br>S | 3<br>Y | 4<br>Q | 5<br>Q | 6<br>G | 7<br>V | 8<br>L | 9<br>S | 10<br>A | 11<br>T | 12<br>I | 13<br>L | 14<br>Y | 15<br>E | 16<br>I | 17<br>L | 18<br>L | 19<br>G | 20<br>K |
|---|---|---|---|---|---|---|---|---|---|---|---|---|---|---|---|---|---|---|---|---|---|---|
| M12887 | TRBC1*01 F EX3 gDNA | | gtg | tcc | tac | cag | caa | ggg | gtc | ctg | tct | gcc | acc | atc | ctc | tat | gag | atc | ctg | cta | ggg | aag |
| M14157 | TRBC1*01 F EX3 gDNA | | --- | --- | --- | --- | --- | --- | --- | --- | --- | --- | --- | --- | --- | --- | --- | --- | --- | --- | --- | --- |
| L36092(1) | TRBC1*02 F EX3 gDNA | | --- | --- | --- | --- | --- | --- | --- | --- | --- | --- | --- | --- | --- | --- | --- | --- | --- | --- | --- | --- |
| IMGT000021 | TRBC1*03 F EX3 gDNA | | --- | --- | --- | --- | --- | --- | --- | --- | --- | --- | --- | --- | --- | --- | --- | --- | --- | --- | --- | --- |

|  |  | | 21<br>A | 22<br>T | 23<br>L | 24<br>Y | 25<br>A | 26<>V | 27<br>L | 28<br>V | 29<br>S | 30<br>A | 31<br>L | 32<br>V | 33<br>L | 34<br>M | 35<br>A | 36<br>M |
|---|---|---|---|---|---|---|---|---|---|---|---|---|---|---|---|---|---|---|
| M12887 | TRBC1*01 F EX3 gDNA | | gcc | acc | ctg | tat | gct | gtg | ctg | gtc | agc | gcc | ctt | gtg | ttg | atg | gcc | atg |
| M14157 | TRBC1*01 F EX3 gDNA | | --- | --- | --- | --- | --- | --- | --- | --- | --- | --- | --- | --- | --- | --- | --- | --- |
| L36092(1) | TRBC1*02 F EX3 gDNA | | --- | --- | --- | --- | --- | --- | --- | --- | --- | --- | --- | --- | --- | --- | --- | --- |
| IMGT000021 | TRBC1*03 F EX3 gDNA | | --- | --- | --- | --- | --- | --- | --- | --- | --- | --- | --- | --- | --- | --- | --- | --- |

|  |  | | 1<br>V | 2<br>K | 3<br>R | 4<br>K | 5<br>D | 6<br>F |
|---|---|---|---|---|---|---|---|---|
| M12887 | TRBC1*01 F EX4 gDNA | | gtc | aag | aga | aag | gat | ttc |
| M14157 | TRBC1*01 F EX4 gDNA | | --- | --- | --- | --- | --- | --- |
| L36092(1) | TRBC1*02 F EX4 gDNA | | --- | --- | --- | --- | --- | --- |
| IMGT000021 | TRBC1*03 F EX4 gDNA | | --- | --- | --- | --- | --- | --- |

INDUCIBLE T CELL RECEPTORS AND USES THEREOF

The present invention relates to (nucleic acids encoding) inducible T cell receptors, compositions and kits, vectors and host cells comprising such (nucleic acids encoding) inducible T cell receptors, uses thereof in preparing inducible T cell receptors and host cells comprising such T cell receptors, methods for preparing such inducible T cell receptors and for dimerizing T cell receptors, as well as medical uses of such compounds and pharmaceutical compositions comprising them, particularly for treating cancer. Particularly, the present invention relates to combinations comprising one or more nucleic acid molecules, said one or more nucleic acid molecules comprising a nucleic acid sequence A encoding for a TCR alpha chain linked to a dimerization domain, and a nucleic acid sequence B encoding for a TCR beta chain linked to a dimerization domain, as well as proteins encoded by such nucleic acid molecules and corresponding uses and methods as defined herein and in the claims.

The development of potent T cell therapy also comes with increased risk of adverse events such as on-target and off-target side effects. Acute toxicities, such as cytokine release syndrome, have become more evident as T cell therapies become more efficient. For a safe adoptive T cell therapy, the ability to control genetically modified T cells is of crucial importance. The development of methods to control genetically modified T cells have been the focus of intense research. Administration of T cell suppressive drugs is generally incomplete and non-specific. Engineering T cells with additional safety switches such as suicide genes has ultimately led to depletion of most of those cells. However, the resultant increase in basal apoptosis as well as the expansion of the remaining T cells potentially limits its efficacy.

Accordingly, the technical problem underlying the present invention was to comply with the objectives set out above. The technical problem has been solved by means and methods as described herein, illustrated in the examples and as defined in the claims.

The current inventors have addressed the above mentioned problems and developed modifications to recombinant T cell receptors (TCR) eliciting a controllable TCR protein expression. The inducible TCRs according to the present invention comprise mutations in the constant alpha and/or beta chains, resulting in the loss of pairing of both chains. In addition, the inventive inducible TCRs comprise dimerizing domains added downstream of the constant alpha and beta chains. The dimerizing domains are characterized by a conditional state of dimerization depending on the addition of a dimerizing agent. Upon induction of dimerization with the respective dimerizing agent, membrane expression of the given TCR is achieved.

The present invention thus provides modifications to recombinant antigen-specific T cell receptors (TCR), wherein the modifications elicit control of the protein membrane expression of the antigen-specific recombinant TCR. In a further aspect, the invention provides nucleic acids encoding such TCR modifications, vectors comprising such nucleic acids, host cells comprising such vectors and nucleic acids, and various uses and applications thereof.

Specifically, as has surprisingly been found in context of the present invention, point mutations in the C-terminal constant alpha and/or beta chains of a TCR result in the suppression or inhibition of the natural pairing of the two chains. As a result, the TCR cannot form a complex of the correctly paired alpha and beta chain together with the T cell receptor complex CD3. Thus, either none or only a very small number of TCRs are expressed on the surface of the recombinant T cells which results in inability of the T cell to recognize antigen with subsequent triggering of functions.

Additionally, dimerization domains are introduced downstream of the constant regions of the alpha and beta chains of the TCR to allow dimerization of the TCR upon addition of a dimerization agent, wherein the dimerization domains and the dimerization agent overcome the suppressed/inhibited pairing of the TCRs due to the point mutations. The overlaying principle is thus an induced dimerization, e.g. a chemically induced dimerization (CID) of the TCR alpha and beta chains, wherein the chains do not pair in the absence of dimerization agents.

Accordingly, the present invention relates to inducible T cell receptors (TCR) with a dimerization domain downstream to the constant alpha and the beta chain respectively which dimerize and, thus, are expressed on the surface of the cell membrane upon induction by a dimerization agent.

In one aspect, the present invention relates to a combination comprising one or more nucleic acid molecules, said one or more nucleic acid molecules comprising:
(a) a nucleic acid sequence A, comprising (i) a nucleic acid sequence encoding an amino acid sequence being at least 90%, 91%, 92%, 93%, 94%, 95%, 96%, 97%, 97.5%, 98%, 98.5% or 99% identical to SEQ ID NO: 2, and (ii) a nucleic acid sequence encoding an inducible dimerization domain being downstream linked to said nucleic acid sequence encoding an amino acid sequence being at least 90%, 91%, 92%, 93%, 94%, 95%, 96%, 97%, 97.5%, 98%, 98.5% or 99% identical to SEQ ID NO: 2; and (b) a nucleic acid sequence B, comprising (i) a nucleic acid sequence encoding an amino acid sequence being at least 90%, 91%, 92%, 93%, 94%, 95%, 96%, 97%, 98%, 98.5% or 99% identical to SEQ ID NO: 4, and (ii) a nucleic acid sequence encoding an inducible dimerization domain being downstream linked to said nucleic acid sequence encoding an amino acid sequence being at least 90%, 91%, 92%, 93%, 94%, 95%, 96%, 97%, 97.5%, 98%, 98.5% or 99% identical to SEQ ID NO: 4, analogously to the localization of the dimerization domain linked to the nucleic acid sequence encoding an amino acid sequence being at least 90%, 91%, 92%, 93%, 94%, 95%, 96%, 97%, 97.5%, 98%, 98.5% or 99% identical to SEQ ID NO: 2 of (a)(ii), said dimerization domain corresponding to the dimerization domain linked to the nucleic acid sequence encoding an amino acid sequence being at least 90%, 91%, 92%, 93%, 94%, 95%, 96%, 97%, 97.5%, 98%, 98.5% or 99% identical to SEQ ID NO: 2 of (a)(ii), wherein said amino acid sequence being at least 90%, 91%, 92%, 93%, 94%, 95%, 96%, 97%, 97.5%, 98%, 98.5% or 99% identical to SEQ ID NO: 2 of (a)(i) comprises at least one, preferably at least two amino acid substitution(s) compared to SEQ ID NO: 2, and/or said amino acid sequence being at least 90%, 91%, 92%, 93%, 94%, 95%, 96%, 97%, 97.5%, 98%, 98.5% or 99% identical to SEQ ID NO: 4 of (b)(i) comprises at least one, preferably at least two, more preferably at least three amino acid substitution(s) compared to SEQ ID NO: 4.

In accordance with the present invention, the description of nucleic acid sequence A or B comprising a nucleic acid sequence encoding an inducible dimerization domain being linked downstream to said nucleic acid sequence encoding an amino acid sequence being at least 90%, 91%, 92%, 93%, 94%, 95%, 96%, 97%, 97.5%, 98%, 98.5% or 99% identical to SEQ ID NO: 2 (encoding a TCR constant alpha chain) or SEQ ID NO: 4 (encoding a TCR constant beta chain allele 2), respectively, also means that the corresponding amino acid sequence (i.e. protein) encoded by said nucleic acid sequence A or B comprises an inducible dimerization domain linked downstream to the amino acid sequence (i.e. protein) encoded by said nucleic acid sequence encoding an amino acid sequence being at least 90%, 91%, 92%, 93%, 94%, 95%, 96%, 97%, 97.5%, 98%, 98.5% or 99% identical to SEQ ID NO: 2 or 4, respectively. In other words, not only the encoding nucleic acid sequences encoding the TCR constant alpha or beta chain and the dimerization domain are linked, but also the encoded and expressed amino acid sequences and, thus, polypeptides are linked (i.e. resulting in a protein comprising a TCR constant alpha chain linked to an inducible dimerization domain and/or a protein comprising a TCR constant beta chain linked to an inducible dimerization domain, respectively). As understood in context with the present invention, said nucleic acid sequence encoding an amino acid sequence being at least 90%, 91%, 92%, 93%, 94%, 95%, 96%, 97%, 97.5%, 98%, 98.5% or 99% identical to SEQ ID NO: 2 or 4 encode a TCR constant alpha or beta chain, respectively. The amino acid sequences (i.e. proteins) encoded by nucleic acid sequences A and B (and, thus, the nucleic acid molecules comprising said sequences) are preferably understood in context of the present invention to encode a TCR alpha and beta chain (including the respective variable and constant regions) comprising an inducible dimerization domain, respectively, and are thus suitable for provision and preparation of an inducible TCR as described herein.

In accordance with the present invention, nucleic acid sequence A preferably encodes a TCR alpha chain including the variable and the constant region, and nucleic acid sequence B preferably encodes a TCR beta chain including the variable and the constant region. As known in the art, a TCR is mainly composed of an alpha and beta chain, each chain comprising a variable and a constant region, the TCR further comprising an adjacent transmembrane region and cytoplasmic region. The constant region is located downstream to the variable region of the TCR and proximal to the cell membrane, followed by a transmembrane region and a short cytoplasmic region. The constant regions of the alpha and beta chains normally pair by cysteine-based disulfide bonds in the extracellular domain (see, e.g., Glusman et al., Immunity (2001), 15: 337-349; Call et al., Cell (2002), 111: 967-979). The gist of the present invention lies in that the constant regions of the alpha and/or beta chain of the TCR comprise one or more mutations which lead to a loss of said pairing of the alpha and beta chains (i.e. amino acid sequence being at least 90%, 91%, 92%, 93%, 94%, 95%, 9697%, 97.5%, 98%, 98.5% or 99% identical to SEQ ID NO: 2 encoding a corresponding TCR constant alpha chain comprised by nucleic acid sequence A, and amino acid sequence being at least 90%, 91%, 92%, 93%, 94%, 95%, 96%, 97%, 97.5%, 98%, 98.5% or 99% identical to SEQ ID NO: 4 encoding a corresponding TCR constant beta chain comprised by nucleic acid sequence B, where the chains exhibit impaired pairing abilities due to one or more mutations in the TCR constant alpha and/or beta chain). Accordingly, nucleotide differences comprised by nucleic acid sequences A and/or B compared to SEQ ID NO: 1 and/or 3, respectively, which lead to amino acid substitutions as described herein, preferably result in a loss of natural pairing of the alpha and beta chains of the TCR. In accordance of the present invention, this loss of natural pairing can be overcome by induced (controlled) dimerization via the dimerization domains encoded by the sequences which are introduced into nucleic acid sequences A and B, wherein said dimerization domains dimerize upon addition of a suitable dimerization agent as described herein. That is, said dimerization domains do not or at least not to a substantial extent dimerize unless being induced by addition of a suitable dimerization agent and are therefore also referred to as inducible dimerization domains. Thus, the combination of nucleic acid molecules described and provided herein provide for or can be used for preparation of an inducible TCR (iTCR) which can be induced (i.e. induction of dimerization of the respective alpha and beta chain) upon addition of a dimerization agent as described herein. As used herein, the term "combination" may also comprise or be referred to as "a composition" where one or more of said nucleic acid molecules are comprised or brought together in combination.

The nucleic acid sequence A of the nucleic acid molecules as described herein comprises a nucleic acid sequence encoding an amino acid sequence being at least 90%, 91%, 92%, 93%, 94%, 95%, 96%, 97%, 97.5%, 98%, 98.5% or 99% identical to SEQ ID NO: 2 (SEQ ID NO: 2 encoding the aa sequence of human constant region of TCR alpha chain), preferably at least 97.5%, 98%, 98.5% or 99%, more preferably at least 98.5% or even 99%. The nucleic acid sequence B of the nucleic acid molecules as described herein comprises a nucleic acid sequence encoding an amino acid sequence being at least 90%, 91%, 92%, 93%, 94%, 95%, 96%, 97.5%, 98%, 98.5% or 99% identical to SEQ ID NO: 4 (SEQ ID NO: 4 encoding the aa sequence of human constant region of TCR beta chain), preferably at least 97.5%, 98%, 98.5% or 99%, more preferably at least 98% or even 98.5%. In context with the present invention, amino acid substitutions compared to SEQ ID NO: 2 are preferably conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be in an acidic amino acid substituted for another acidic amino acid, an amino acid with a nonpolar side chain substituted for another amino acid with a nonpolar side chain, a basic amino acid substituted for another basic amino acid, an amino acid with a polar side chain substituted for another amino acid with a polar side chain, etc. that may be made, for instance, on the basis of similarity in polarity, charge, solubility, hydrophobicity, hydrophilicity, and/or the amphipathic nature of the residues involved. For example, "conservative" substitutions may mean substitutions as listed as "Exemplary Substitutions" in Table I below. "Highly conservative" substitutions as used herein mean substitutions as shown under the heading "Preferred Substitutions" in Table I below.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |

TABLE I-continued

Amino Acid Substitutions

| Original | Exemplary Substitutions | Preferred Substitutions |
|---|---|---|
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

In one embodiment of the present invention, said amino acid sequence being at least 90%, 91%, 92%, 93%, 94%, 95%, 96%, 97.5%, 98%, 98.5% or 99% (preferably at least 98.5 or 99%%) identical to SEQ ID NO: 2 of (a)(i) comprises amino acid substitutions at positions 44 and/or 47 compared to SEQ ID NO: 2, and/or said amino acid sequence being at least 90%, 91%, 92%, 93%, 94%, 95%, 96%, 97.5%, 98%, 98.5% or 99% (preferably at least 98% or 98.5%) identical to SEQ ID NO: 4 of (b)(i) comprises amino acid substitutions at positions 4, 5, 37, 63, 77 and/or 79 compared to SEQ ID NO: 4. In one embodiment of the present invention, the amino acid substitutions at positions 44 and/or 47 compared to SEQ ID NO: 2 are conservative amino acid substitutions.

The amino acid sequence shown in SEQ ID NO: 2 may be encoded by a nucleotide sequence shown in SEQ ID NO: 1. Accordingly, the amino acid sequences being at least 90%, 91%, 92%, 93%, 94%, 95%, 96%, 97.5%, 98%, 98.5% or 99% (preferably at least 98.5% or 99%) identical to SEQ ID NO: 2 and encoded by the nucleic acid sequences of (a)(i) as described herein may be encoded by nucleotide sequences according to SEQ ID NO: 1 where the respective nucleotides are replaced in order to result in the corresponding amino acid substitutions compared to SEQ ID NO: 2. The amino acid sequence of SEQ ID NO: 2 may also be encoded by a nucleotide sequence according to SEQ ID NO: 1 where one or more nucleotides are replaced, where such replacements do not translate into an amino acid substitution (silent mutation). Accordingly, the nucleic acid sequence encoding an amino acid sequence being at least 90%, 91%, 92%, 93%, 94%, 95%, 96%, 97.5%, 98%, 98.5% or 99% (preferably at least 98% or 98.5%) identical to SEQ ID NO: 2 may correspond to the nucleotide sequence of SEQ ID NO: 1 where the respective nucleotides are replaced in order to result in the corresponding amino acid substitutions compared to SEQ ID NO: 2, and which further comprises additional nucleotide replacements which do not result in amino acid substitutions.

Likewise, the amino acid sequence shown in SEQ ID NO: 4 may be encoded by a nucleotide sequence shown in SEQ ID NO: 3. Accordingly, the amino acid sequences being at least 90%, 91%, 92%, 93%, 94%, 95%, 96%, 97.5%, 98%, 98.5% or 99% (preferably at least 98.5% or 99%) identical to SEQ ID NO: 4 and encoded by the nucleic acid sequences of (b)(i) as described herein may be encoded by nucleotide sequences according to SEQ ID NO: 3 where the respective nucleotides are replaced in order to result in the corresponding amino acid substitutions compared to SEQ ID NO: 4. The amino acid sequence of SEQ ID NO: 4 may also be encoded by a nucleotide sequence according to SEQ ID NO: 3 where one or more nucleotides are replaced, where such replacements do not translate into an amino acid substitution (silent mutation). Accordingly, the nucleic acid sequence encoding an amino acid sequence being at least 90%, 91%, 92%, 93%, 94%, 95%, 96%, 97.5%, 98%, 98.5% or 99% (preferably at least 98% or 98.5%) identical to SEQ ID NO: 4 may correspond to the nucleotide sequence of SEQ ID NO: 3 where the respective nucleotides are replaced in order to result in the corresponding amino acid substitutions compared to SEQ ID NO: 4, and which further comprises additional nucleotide replacements which do not result in amino acid substitutions.

Table 1 shows the amino acid changes introduced in both alpha and beta constant regions of alpha and beta chain of human TCR (cf. SEQ ID NO: 2 and 4, respectively), wherein the changes in the amino acid sequence compared to SEQ ID NO: 2 (for TCR constant alpha chain) and SEQ ID NO: 4 (for TCR constant beta chain) leads to an impairment of alpha and beta chains pairing, yet still allowing the correct assembly of the alpha chain of the TCR with CD3 epsilon and delta subunits and assembly of the beta chain of the TCR with CD3 gamma and epsilon subunits, as can be seen in Examples 1-6. The amino acid position of the substitution is shown with reference to the sequence listing and with reference to the IMGT numbering system as shown in FIGS. 11 and 12. As is clear to the skilled person following the IMGT numbering, position 84.1 is a position between positions 84 and 85 of human TCR amino acid sequence (Lefranc, M.-P., Immunology Today 18, 509 (1997)).

| TCR constant chain | Amino acid position SEQ ID | Amino acid position IMGT numbering | Amino Acid | Mutated to: |
|---|---|---|---|---|
| Alpha | SEQ ID NO: 2 44 | TRAC FIG. 11 81 | T | A |
|  | SEQ ID NO: 2 47 | TRAC FIG. 11 84 | T | A |
| Beta | SEQ ID NO: 4: 63 | TRBC FIG. 12 84.1 | L | A |
|  | SEQ ID NO: 4: 77 | TRBC FIG. 12 86 | S | A |
|  | SEQ ID NO: 4: 79 | TRBC FIG. 12 88 | R | A |

Table 2 shows the amino acid changes introduced in the beta constant regions of human TCR (SEQ ID NO: 4), wherein the changes in the amino acid sequence compared to SEQ ID NO: 4 (for TCR constant beta chain) leads to an impairment of alpha and beta chains pairing, yet still allowing the correct assembly of the alpha chain of the TCR with CD3 epsilon and delta subunits and assembly of the beta chain of the TCR with CD3 gamma and epsilon subunits, as can be seen from Examples 7 and 8. There are two alleles for the TCR beta chain constant region which are termed C1 and C2. The amino acid position of the substitution is shown with reference to the sequence listing and with reference to the IMGT numbering system as shown in FIG. 12. The table 2 below shows the differences between the two alleles of the Beta constant chain. While SEQ ID NO: 4 refers to the C2 constant chain showing the Amino acids K, N and Y at positions 4, 5 and 37 (1.3, 1.4 and 29 using IMGT numbering shown in the table below), FIG. 12 shows the C1 constant chain. Mutations in the constant chains at the positions outlined in Table 2 lead to a reduced pairing of the alpha and the beta chain.

| TCR constant chain | Amino acid position | Amino acid | Mutated to: |
|---|---|---|---|
| Beta (TRBC1) | 13 | K | V |
| | 14 | N | P |
| | 29 | F | K |

In one embodiment of the present invention, said dimerization domains being downstream linked to the nucleic acid sequences A and B, respectively, are located C-terminally of the TCR when expressed, preferably in the cytoplasmic region after expression and localization of the TCR. In this context, as clear to the skilled person, the TCR is normally localized in the membrane of the cell after complex formation of the alpha and beta chain (together with the CD3 complex) (see, e.g., Call et al., loc. cit.), i.e. after dimerization of said dimerization domains encoded by nucleic acid sequences A and B as defined and provided herein.

In one embodiment of the present invention, for the combination (or composition) described and provided herein, said nucleic acid sequence A and nucleic acid sequence B may be comprised by separate nucleic acid molecules or comprised in one nucleic acid molecule. For example, nucleic acid sequences A and B may be located on the same nucleic acid molecule, e.g., on an expression cassette. In such an expression cassette, nucleic acid sequences A and B may preferably be under the same expression control, e.g. under the control of the same promoter or the same promoter type in order to allow comparable amounts of expression.

In one embodiment of the present invention, said nucleic acid sequence of (a)(i) encodes an amino acid sequence being at least 90%, 91%, 92%, 93%, 94%, 95%, 96%, 97.5%, 98%, 98.5% or 99% (preferably at least 98.5% or 99%) identical to SEQ ID NO: 2 comprising at least one amino acid substitution compared to the amino acid sequence of SEQ ID NO: 2, said substitution being selected from the group consisting of T44A, and T47A; and/or said nucleic acid sequence of (b)(i) encodes an amino acid sequence being at least 90%, 91%, 92%, 93%, 94%, 95%, 96%, 97.5%, 98%, 98.5% or 99% (preferably at least 98% or 98.5%) identical to SEQ ID NO: 4 comprising at least one amino acid substitution compared to the amino acid sequence of SEQ ID NO: 4, said substitution being selected from the group consisting of L63A, S77A, and R79A. In another embodiment, said nucleic acid of (b)(i) encodes an amino acid sequence being at least 90%, 91%, 92%, 93%, 94%, 95%, 96%, 97.5%, 98%, 98.5% or 99% (preferably at least 98% or 98.5%) identical to SEQ ID NO: 4 comprising at least one amino acid substitution compared to the amino acid sequence of SEQ ID NO: 4, said substitution being selected from the group consisting of K4V, N5P and Y37K.

In one preferred embodiment of the present invention, said nucleic acid sequence of (a)(i) encodes an amino acid sequence being at least 90%, 91%, 92%, 93%, 94%, 95%, 96%, 97.5%, 98%, 98.5% or 99% (preferably at least 98.5% or 99%) identical to SEQ ID NO: 2 comprising two amino acid substitutions compared to the amino acid sequence of SEQ ID NO: 2, said two substitutions being T44A and T47A; and said nucleic acid sequence of (b)(i) encodes an amino acid sequence being at least 90%, 91%, 92%, 93%, 94%, 95%, 96%, 97.5%, 98%, 98.5% or 99% (preferably at least 98% or 98.5%) identical to SEQ ID NO: 4 comprising three amino acid substitutions compared to the amino acid sequence of SEQ ID NO: 4, said three substitutions being L63A, S77A, and R79A.

In another preferred embodiment, said nucleic acid sequence of (a)(i) encodes an amino acid sequence being at least 90%, 91%, 92%, 93%, 94%, 95%, 96%, 97.5%, 98%, 98.5% or 99% (preferably at least 98.5% or 99%) identical to SEQ ID NO: 2 and said nucleic acid sequence of (b)(i) encodes an amino acid sequence being at least 90%, 91%, 92%, 93%, 94%, 95%, 96%, 97.5%, 98%, 98.5% or 99% (preferably at least 98% or 98.5%) identical to SEQ ID NO: 4 comprising three amino acid substitutions compared to the amino acid sequence of SEQ ID NO: 4, said three substitutions being K4V, N5P and Y37K.

In one embodiment of the present invention, the nucleic acid sequence A encodes an amino acid sequence shown in SEQ ID NO: 5.

In one embodiment of the present invention, the nucleic acid sequence B encodes an amino acid sequence shown in SEQ ID NO: 6.

In context with the present invention, the inducible dimerization domain is a dimerization domain which dimerizes upon addition of a dimerization agent. In the amino acid sequence (i.e. protein) encoded by nucleic acid sequence A and B, respectively, the dimerization domain is linked to and located downstream (i.e. C-terminally) of the constant alpha or beta chain (encoded by the nucleic acid sequence being at least 90%, 91%, 92%, 93%, 94%, 95%, 96%, 97%, 98%, 98.5% or 99% identical to SEQ ID NO: 2 or SEQ ID NO: 4, respectively) which exhibit impaired pairing abilities. Preferably the inducible dimerization domain is located in the cytoplasmic domain of the iTCR. As the skilled person is aware, a TCR is formed at the endoplasmic reticulum (ER) and then, upon pairing of the alpha and beta chains, formed with CD3 to a complex and then localized to the cell membrane/cell surface via the Golgi apparatus. In context with the present invention, the alpha and beta chains of the iTCR do not pair due to the mutation(s) in the respective constant region(s) as described and provided herein, and, thus, do not leave the ER upon dimerization via the inducible dimerization domains (which, in turn, dimerize upon addition of a suitable dimerization agent). In context with the present invention, the inducible dimerization domain may be a homo- or a heterodimerization domain, preferably a homodimerization domain. In context with the present invention, suitable Examples for such dimerization domains are known in the art and comprise, inter alia, estrogen receptor (e.g., ERT2; cf. Ballister, Publicly Accessible Penn Dissertations (2014), 1202: Inducible Protein Dimerization: New Tools and Applications to Understanding the Mitotic Checkpoint), FKBP (cf. Ballister, loc.cit), FKBP/Calcineurin A (CNA) (cf. Ho et al., Nature (1996), 382: 822-826); FKBP/CyP-Fas (cf. Belshaw et al., PNAS (1996), 93: 4304-4607), FKBP/FRB domain of mTOR (. Ballister, Publicly Accessible Penn Dissertations (2014), 1202: Inducible Protein Dimerization: New Tools and Applications to Understanding the Mitotic Checkpoint), GyrB (M. A. Farrar et al., Methods in Enzymology, Volume 327, 2000, pages 421-429).), GAI/GID1 (Miyamato et al., Nature Chemical Biology (2012), 8: 465-470), Snap-Tag/HaloTag (cf. Erhart et al., Chem & Biol (2013), 20: 549-557), and eDHFR/HaloTag (Ballister et al., Nature Communications 5, Article number: 5475 (2014), doi: 10.1038/ncomms6475).

The present invention relates to an expression cassette comprising the nucleic acid sequence A and the nucleic acid sequence B as described and provided herein, or at least two expression cassettes, wherein at least one expression cassette comprises the nucleic acid sequence A as described and provided herein and at least one expression cassette comprises the nucleic acid sequence B as described and provided herein. In one embodiment of the present invention, nucleic acid sequences A and B are under the control of the same elements (e.g., promoter and/or enhancer, operators, repressors, and transcription termination signals and the like), and, if comprised by the same expression control, may be under common control of the same element. Promoters may be, e.g., constitutive promoters or inducible promoters. Suitable promoters/enhancers for mammalian host cells are known in the art and comprise, e.g., SV40, AdMLP, metallothionein promoter, 7.5K promoter, MIEP, EF1A, CMV, PGK and others.

The present invention further relates to vectors comprising nucleic acid sequences A and/or B as described and provided herein, or expression cassettes as described and provided herein. Suitable vectors depend on the respective host cell where the vector is to be introduced (transformed, transduced) and are known in the art. The term "vector" as used herein encompasses, without limitation plasmids, viral vectors (including retroviral vectors, lentiviral vectors, adenoviral vectors, vaccinia virus vectors, polyoma virus vectors, and adenovirus-associated vectors (AAV); retroviral and lentiviral vectors being preferred in context with the present invention), phages, phagemids, cosmids and artificial chromosomes (including BACs and YACs). The vector itself is generally a nucleotide sequence, commonly a DNA sequence that comprises an insert (transgene) and a larger sequence that serves as the "backbone" of the vector. Engineered vectors typically comprise an origin for autonomous replication in the host cells (if stable expression of the polynucleotide is desired), selection markers, and restriction enzyme cleavage sites (e.g. a multiple cloning site, MCS). Vector may additionally comprise promoters/enhancers and other control elements as described herein and known in the art such as operators, repressors, and transcription termination signals, as well as genetic markers, reporter genes, targeting sequences, and/or protein purification tags. As known to those skilled in the art, large numbers of suitable vectors are available and many are commercially available. Examples of suitable vectors are provided, e.g., in J. Sambrook et al., Molecular Cloning: A Laboratory Manual (4th edition), Cold Spring Harbor Laboratory, Cold Spring Harbor Laboratory Press, New York (2012).

The vector of the present invention can also be an expression vector. "Expression vectors" or "expression constructs" can be used for the transcription of heterologous polynucleotide sequences, for instance those encoding the TCR chains described and provided in context with the present invention (encoded by nucleic acid sequences A and B), and translation of their mRNA in a suitable host cell. Besides an origin of replication, selection markers, and restriction enzyme cleavage sites, expression vectors typically include one or more regulatory sequences operably linked to the heterologous polynucleotide to be expressed. The term "regulatory sequence" refers to a nucleic acid sequence necessary for the expression of an operably linked coding sequence of a (heterologous) polynucleotide in a particular host organism or host cell and thus include transcriptional and translational regulatory sequences. Typically, regulatory sequences required for expression of heterologous polynucleotide sequences in prokaryotes include a promoter(s), optionally operator sequence(s), and ribosome binding site(s). In eukaryotes, promoters, polyadenylation signals, enhancers and optionally splice signals are typically required. Moreover, specific initiation and secretory signals also may be introduced into the vector in order to allow for secretion of the polypeptide of interest into the culture medium. A nucleic acid is "operably linked" when it is placed into a functional relationship with another nucleic acid sequence, in particular on the same polynucleotide molecule. For example, a promoter is operably linked with a coding sequence of a heterologous gene when it is capable of effecting the expression of that coding sequence. The promoter is typically placed upstream of the gene encoding the polypeptide of interest and regulates the expression of said gene. Exemplary regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. As set out before, the expression vectors may also include origins of replication and selectable markers. Vectors of the invention may further comprise one or more selection markers. Suitable selection markers for use with eukaryotic host cells include, without limitation, the herpes simplex virus thymidine kinase (tk), hypoxanthine-guanine phosphoribosyltransferase (hgprt), and adenine phosphoribosyltransferase (aprt) genes. Other genes include dhfr (methotrexate resistance), gpt (mycophenolic acid resistance) neo (G-418 resistance) and hygro (hygromycin resistance). Vector amplification can be used to increase expression levels. In general, the selection marker gene can either be directly linked to the polynucleotide sequences to be expressed, or introduced into the same host cell by co-transformation. In view of the above, the present invention thus further provides one or more of the nucleotide sequences described herein inserted into (i.e. comprised by) a vector. Specifically, the invention provides (replicable) vectors comprising nucleic acid sequence A and/or B as described and provided herein.

The skilled person will readily be able to select a suitable expression vector based on, e.g., the host cell intended for expression of the amino acid sequences (proteins) encoded by nucleotide sequences A and/or B. Particular examples for suitable expression vectors are viral vectors, such as retroviral vectors e.g. MP71 vectors or retroviral SIN vectors; and lentiviral vectors or lentiviral SIN vectors. Viral vectors are for instance capable of infecting lymphocytes, which are envisaged to subsequently express the amino acid sequences (proteins) encoded by nucleotide sequences A and/or B. Another example for a suitable expression vector is the Sleeping Beauty (SB) transposon transposase DNA plasmid system, SB DNA plasmid. The nucleic acids and/or in particular expression constructs of the invention can also be transferred into cells by transient RNA transfection. Currently used viral vectors for native TCR expression typically link the TCR-alpha and TCR-beta chain genes in one vector with either an internal ribosomal entry site (IRES) sequence or the 2A peptide sequence derived from a porcine tsechovirus, resulting in the expression of a single messenger RNA (mRNA) molecule under the control of the viral promoter within the transduced cell. However, the skilled person will readily be able to select and use also other known systems for introducing the nucleotide sequences A and/or B of the present invention into suitable expression systems, such as CRISPR/Cas or Sleeping Beauty (SB) transposons.

The present invention also relates to amino acid sequences and proteins (used interchangeably in this context) encoded by nucleic acid sequences as described and provided herein, inter alia encoded by nucleic acid sequence A and/or B. The combination of amino acid sequences (proteins) encoded by nucleic acids comprising nucleic acid sequence A and B provides or is useful for preparation of an iTCR as described and provided herein. Thus, the present invention also relates to an iTCR prepared by using amino acid sequences (proteins) encoded by nucleic acids comprising nucleic acid sequence A and B, or prepared by using nucleic acids comprising nucleic acid sequence A and B. As described herein an iTCR is a TCR which exhibits impaired pairing of the alpha and beta chain and which comprises a C-terminal inducible dimerization domain (as described herein) on both, alpha and beta chain, but which dimerizes upon addition of a suitable dimerization agent. A pairing ability of a TCR may be considered "impaired" in context with the present invention if at least 2-, 3-, 4-, or 5-fold less TCR can be measured in the cell membrane of a given TCR producing cell compared to the amount of native human TCR (having TCR constant alpha and beta chains as shown in SEQ ID NO: 2 and 4, respectively) in the cell membrane. Suitable measurement methods are known in the art and comprise, e.g., flow cytometry as exemplified herein.

The present invention also relates to amino acid sequences and proteins encoded nucleic acid sequences being at least 90%, 91%, 92%, 93%, 94%, 95%, 96%, 97.5%, 98%, 98.5% or 99% (preferably at least 98.5% or 99%) identical to SEQ ID NO: 2 and encoding a TCR constant alpha chain, which is not able to pair with a native human TCR constant beta chain according to SEQ ID NO: 4. The present invention also relates to amino acid sequences and proteins encoded nucleic acid sequences being at least 90%, 91%, 92%, 93%, 94%, 95%, 96%, 97.5%, 98%, 98.5% or 99% (preferably at least 98% or 98.5%) identical to SEQ ID NO: 4 and encoding a TCR constant beta chain, which is not able to pair with a native human TCR constant alpha chain according to SEQ ID NO: 2.

As described herein, the inducible dimerization domain which is linked to the amino acid sequence being at least 90%, 91%, 92%, 93%, 94%, 95%, 96%, 97.5%, 98%, 98.5% or 99% (preferably at least 98.5% or 99%) identical to SEQ ID NO: 2 or 4 (encoding a TCR constant alpha or beta chain, respectively) as encoded by nucleic acid A or B (encoding a TCR alpha or beta chain, respectively, with the downstream linked dimerization domain) dimerizes and, thus, brings both chains together upon addition of a proper dimerization agent. Such dimerization agent depends on the corresponding dimerization domain linked to the alpha and beta chain of the iTCR to be prepared using the nucleic acid molecules of the combination or composition provided herein, as known to the person skilled in the art. For example, suitable dimerization agents comprise (dependent on the respective dimerization domain) tamoxifen (e.g., 4-hydroxytamoxifen), Endoxifen, AP21967, 4-(1-[4-(Dimethylaminoethoxy)phenyl]-2-phenyl-1-butenyl)phenol, and 23,27-Epoxy-3H-pyrido[2,1-c][1,4]oxaazacyclohentriacontine, FK1012, FK506, FKCsA, Rapamycin, Coumermycin, Gibberellin, HaXS, and TMP-HTag. In one embodiment of the present invention, particularly for estrogen receptor (e.g., ERT2) being the dimerization domain encoded by nucleic acid sequence A and B, the dimerization agent is tamoxifen or endoxifen, preferably endoxifen. Examples of appropriate dimerization domain/dimerization agent pairs are shown in Table 3.

TABLE 3

Examples of suitable dimerization domain/dimerization agent pairs

| Dimerization system | Dimerization | Agent |
|---|---|---|
| Estrogen receptor | Estrogen receptor | Tamoxifen |
| FKBP | FKBP | FK1012 |
| FKBP | CalcineurinA (CNA) | FK506 |
| FKBP | CyP-Fas | FKCsA |
| FKBP | FRB domain of mTOR | Rapamycin |
| GyrB | GyrB | Coumermycin |
| GAI | GID1 | Gibberellin |
| Snap-tag | HaloTag | HaXS |
| eDHFR | HaloTag | TMP-HTag |

The present invention also relates to kits comprising the combination or composition comprising one or more nucleic acid molecules comprising nucleic acid sequence A and/or B as described and provided herein, an expression cassette as described and provided herein, a host cell described and provided herein, and/or a vector as described and provided herein, together with a dimerization agent corresponding to the dimerization domain linked to the amino acid sequence being at least 90%, 91%, 92%, 93%, 94%, 95%, 96%, 97.5%, 98%, 98.5% or 99% (preferably at least 98.5% or 99%) identical to SEQ ID NO: 2 or 4 (SEQ ID NO: 2 for nucleic acid sequence A, and SEQ ID NO: 4 for nucleic acid sequence B), respectively, said dimerization agent being capable of inducing dimerization of said dimerization domains. Capability of inducing dimerization of dimerization domains can be measured by methods known in the art and also exemplified herein. In essence, an agent is able to dimerize an inducible dimerization domain in context with the present invention if upon addition of said agent, increased expression and localization of iTCRs prepared using the methods, combinations, compositions, compounds, vectors, host cells, or kits of the present invention in the cell membrane can be measured; preferably, there at least 2-fold, 3-fold, 4-fold or 5-fold (preferably at least 5-fold) more iTCRs in the cell membrane of a given host cell than without addition of said dimerization agent. Suitable methods for measuring TCR on the cell surface are known in the art and include flow cytometry (see; e.g., FIG. 2). Suitable pairs of dimerization domains and dimerization agents are exemplified in Table 3.

The present invention also relates to host cells comprising nucleic acid molecules comprising the nucleic acid sequence A and the nucleic acid sequence B as described and provided herein, the expression cassette as described and provided herein, and/or the vector as described and provided herein. Suitable host cells are known in the art and comprise inter alia prokaryotic and eukaryotic cells, preferably eukaryotic cells, e.g., mammalian cells. Host cells may comprise, e.g., production host cells or effector host cells.

A variety of host cells can be used in accordance with the invention. As used herein, the term "host cell" encompasses cells which can be or has/have been recipients of nucleic acid molecules or vectors described herein and/or express (and optionally secreting) the amino acid sequences (i.e. proteins) of the present invention (e.g., iTCRs). The terms "cell" and "cell culture" are used interchangeably unless it is clearly specified otherwise. The term "host cell" also includes "host cell lines". In general, the term "host cell" includes prokaryotic or eukaryotic cells, and also includes without limitation bacteria, yeast cells, fungi cells, plant cells, and animal cells such as insect cells and mammalian cells, e.g., murine, rat, macaque or human cells. In view of the above, the invention thus provides, inter alia, host cells comprising a polynucleotide or a vector, e.g. an expression vector comprising a nucleotide sequence encoding amino acid sequences as described herein (e.g., iTCRs). Polynucleotides and/or vectors of the invention can be introduced into the host cells using routine methods known in the art, e.g. by transfection, transformation, or the like.

"Transfection" is the process of deliberately introducing nucleic acid molecules or polynucleotides (including vectors) into target cells. An example is RNA transfection, i.e. the process of introducing RNA (such as in vitro transcribed RNA, ivtRNA) into a host cell. The term is mostly used for non-viral methods in eukaryotic cells. The term "transduction" is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside. Exemplary techniques for transfecting eukaryotic host cells include lipid vesicle mediated uptake, heat shock mediated uptake, calcium phosphate mediated transfection (calcium phosphate/DNA co-precipitation), microinjection and electroporation.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethylene glycol mediated uptake. In view of the above, the present invention thus further provides host cells comprising at least one polynucleotide sequence and/or vector as described herein.

For expression of the amino acid sequences (i.e. proteins) of the invention, a host cell may be chosen that modulates the expression of the inserted polynucleotide sequences, and/or modifies and processes the gene product (i.e. RNA and/or protein) as desired. Such modifications (e.g., glycosylation) and processing (e.g., cleavage) of gene products may be important for the function of the TCR. Different host cells have characteristic and specific mechanisms for the post-translational processing and modification of gene products. Appropriate cell lines or host systems can be chosen to ensure the correct modification and processing of the product. To this end, eukaryotic host cells that possess the cellular machinery for proper processing of the primary transcript, glycosylation, and phosphorylation of the gene product may be used. It is envisaged herein to provide (a) host cells for expressing and obtaining proteins (e.g., iTCRs) of the invention, in particular in soluble form ("production host cells") and (b) host cells expressing a TCR of the invention and having effector function ("effector host cells"). Such "effector host cells" are particularly useful for therapeutic applications and are envisaged for administration to a subject in need thereof. Preferred "effector host cells" include lymphocytes such as cytotoxic T lymphocytes (CTLs), CD8+ T cells, CD4+ T cells, natural killer (NK) cells, natural killer T (NKT) cells, gamma/delta-T-cells.

"Production host cells" used for the expression of proteins of the invention are preferably capable of expressing high amounts of recombinant protein. Exemplary mammalian host cells that can be used for as "production host cells" include Chinese Hamster Ovary (CHO cells) including DHFR minus CHO cells such as DG44 and DUXBI 1, NSO, COS (a derivative of CVI with SV40 T antigen), HEK293 (human kidney), and SP2 (mouse myeloma) cells. Other exemplary host cell lines include, but are not limited to, HELA (human cervical carcinoma), CVI (monkey kidney line), VERY, BHK (baby hamster kidney), MDCK, 293, WI38, R1610 (Chinese hamster fibroblast) BALBC/3T3 (mouse fibroblast), HAK (hamster kidney line), P3×63-Ag3.653 (mouse myeloma), BFA-IcIBPT (bovine endothelial cells), and RAJI (human lymphocyte). Host cell lines are typically available from commercial services, the American Tissue Culture Collection (ATCC) or from published literature. Non-mammalian cells such as bacterial, yeast, insect or plant cells are also readily available and can also be used as "production host cells" as described above. Exemplary bacterial host cells include enterobacteriaceae, such *Escherichia coli, Salmonella; Bacillaceae*, such as *Bacillus subtilis; Pneumococcus; Streptococcus*, and *Haemophilus influenza*. Other host cells include yeast cells, such as *Saccharomyces cerevisiae*, and *Pichia pastoris*. Insect cells include, without limitation, *Spodoptera frugiperda* cells. In accordance with the foregoing, conceivable expressions systems (i.e. host cells comprising an expression vector as described above) include microorganisms such as bacteria (e.g., *E. coli, B. subtilis*) transformed with recombinant bacteriophage DNA, plasmid DNA or cosmid DNA expression vectors; yeast (e.g., *Saccharomyces, Pichia*) transformed with recombinant yeast expression vectors; insect cell systems infected with recombinant virus expression vectors (e.g., baculovirus); plant cell systems infected with recombinant virus expression vectors (e.g., cauliflower mosaic virus, CaMV; tobacco mosaic virus, TMV) or transformed with recombinant plasmid expression vectors (e.g., Ti plasmid). Mammalian expression systems harboring recombinant expression constructs containing promoters derived from the genome of mammalian cells (e.g., metallothionein promoter) or from mammalian viruses (e.g., the adenovirus late promoter; the vaccinia virus 7.5K promoter, the cytomegalovirus (CMV) major immediate-early promoter (MIEP) promoter) are often preferred. Suitable mammalian host cells can be selected from known cell lines (e.g., COS, CHO, BLK, 293, 3T3 cells), however it is also conceivable to use lymphocytes such as cytotoxic T lymphocytes (CTLs), CD8+ T cells, CD4+ T cells, natural killer (NK) cells, natural killer T (NKT) cells, gamma/delta-T-cells.

In accordance with the foregoing, the present invention also provides a method for producing and obtaining a protein (e.g., TCR) as described herein comprising the steps of (i) incubating a host cell (i.e., a production host cell) under conditions causing expression of said protein and (ii) purifying said protein. The host cells harboring the expression vector are grown under conditions appropriate to the production of the proteins provided herein, in particular constant alpha chains and/or beta chains encoded by nucleic acid sequences A and B, respectively, as described herein, and assayed for alpha and/or beta chain protein synthesis. For the expression of double-chained TCRs, vectors encoding both the alpha and beta chains may be co-expressed in the host cell for expression of the entire molecule.

Once a protein (i.e. iTCR) of the invention has been expressed, it may be purified by any purification method known in the art, for example, by chromatography (e.g., ion exchange chromatography (e.g. hydroxylapatite chromatography), affinity chromatography, particularly Protein A, Protein G or lectin affinity chromatography, sizing column chromatography), centrifugation, differential solubility, hydrophobic interaction chromatography, or by any other standard technique for the purification of proteins. The skilled person will readily be able to select a suitable purification method based on the individual characteristics of the protein to be recovered.

As mentioned earlier, the present invention also provides for "effector host cells" comprising a nucleotide sequence, vector or protein of the invention. Said effector host cells are modified using routine methods to comprise a nucleic acid sequence encoding the protein of the invention, and are envisaged to express the protein described herein, in particular on the cell surface. For the purposes of the present invention, "modified host cells expressing a protein of the invention" generally refers to (effector or production) host cells treated or altered to express a protein according to the present invention, for instance by RNA transfection as described in the appended Examples. Other methods of modification or transfection or transduction, such as those described elsewhere herein, are also envisaged. The term "modified host cell" thus includes "transfected", "transduced" and "genetically engineered" host cells preferably expressing the protein of the present invention. Preferably, such "(modified) effector host cells" (in particular "(modified) effector lymphocytes") are capable of mediating effector functions through intracellular signal transduction upon binding of the protein to its specific antigenic target. Such effector functions include for instance the release of perforin (which creates holes in the target cell membrane), granzymes (which are proteases that act intracellularly to trigger apoptosis), the expression of Fas ligand (which activates apoptosis in a Fas-bearing target cell) and the release of cytokines, preferably Th1/Tc1 cytokines such as IFN-γ, IL-2 and TNF-α. Thus, an effector host cell engineered to express the protein of the invention that is capable recognizing and binding to its antigenic target in the subject to be treated is envisaged to carry out the above-mentioned effector functions, thereby killing the target (e.g. cancer) cells. Cytolysis of target cells can be assessed e.g. with the CTL fluorescent killing assay (CTL, USA) detecting the disappearance of fluorescently labeled target cells during co-culture with transfected recipient T cells.

In view of the above, effector host cells preferably express a functional iTCR, i.e. that typically comprises an iTCR alpha and beta chain described herein; and also the signal transducing subunits CD3 gamma, delta, epsilon and zeta (CD3 complex). Moreover, expression of co-receptors CD4 or CD8 may also be desired. Generally, lymphocytes harboring the required genes involved in antigen binding, receptor activation and downstream signalling (e.g. Lck, FYN, CD45, and/or Zap70), T cells are particularly suitable as effector host cells. However, effector host cells expressing the TCR of the invention as a "binding domain" without the CD3 signal transducing subunit and/or aforementioned downstream signalling molecules (i.e. being capable of recognizing the antigenic target described herein, but without effecting functions mediated by CD3 and/or the aforementioned downstream signalling molecules) are also envisaged herein. Such effector cells are envisaged to be capable of recognizing the antigenic target described herein, and optionally of effecting other functions not associated with CD3 signalling and/or signalling of the aforementioned downstream signalling molecules. Examples include NK or NKT cells expressing the inventive protein and being capable of e.g. releasing cytotoxic granules upon recognition of their antigenic target. Thus, cytotoxic T lymphocytes (CTLs), CD8+ T cells, CD4+ T cells, natural killer (NK) cells, natural killer T (NKT) cells, gamma/delta-T-cells are considered useful lymphocyte effector host cells in accordance with the present invention. Such lymphocytes expressing the recombinant iTCR of the invention are also referred to as "modified effector lymphocytes" herein. The skilled person will however readily acknowledge that in general any component of the protein signalling pathway leading to the desired effector function can be introduced into a suitable host cell by recombinant genetic engineering methods known in the art. Effector host cells in particular lymphocytes such as T cells can be autologous host cells that are obtained from the subject to be treated and transformed or transduced to express the protein of the invention. Typically, recombinant expression of the protein will be accomplished by using a viral vector as described in the appended Examples. Techniques for obtaining and isolating the cells from the patient are known in the art. As mentioned earlier, the effector host cells provided herein are particularly envisaged for therapeutic applications. Further genetic modifications of the host cells may be desirable in order to increase therapeutic efficacy. E.g., when using autologous CD8+ T cells as "effector host cells" suitable additional modifications include downregulation of the endogenous TCR, CTLA-4 and/or PD-1 expression; and/or amplification of co-stimulatory molecules such as CD28, CD134, CD137. Means and methods for achieving the aforementioned genetic modifications have been described in the art.

Methods for targeted genome engineering of host cells are known in the art and include, besides gene knockdown with siRNA, the use of so-called "programmable nucleases" such as zinc-finger nucleases (ZFNs), transcription activator-like effector nucleases (TALENs) and RNA-guided engineered nucleases (RGENs) derived from the bacterial clustered regularly interspaced short palindromic repeat (CRISPR)—Cas (CRISPR-associated) system, as inter alia reviewed in Kim & Kim Nature Reviews Genetics 15, 321-334 (2014). For instance, programmable nucleases such as TALENs can be employed to cut the DNA regions that code for "unwanted" proteins, such as PD-1, CTLA-4 or an endogenous TCR, and thereby reducing their expression. When T cells are used as (effector) host cells, downregulation of the endogenous TCR has the benefit of reducing unwanted "mispairing" of endogenous and exogenous TCR alpha/beta chains.

The present invention also relates to the use of a dimerization agent as described herein for dimerizing a protein encoded by the nucleic acid sequence A and a protein encoded by the nucleic acid sequence B as described and provided herein. In one embodiment of the present invention, the dimerization agent to be used for dimerizing a protein encoded by the nucleic acid sequence A and a protein encoded by the nucleic acid sequence B as described and provided herein may be endoxifen.

The present invention further relates to a method for dimerizing a protein encoded by the nucleic acid sequence A and a protein encoded by the nucleic acid sequence B as described and provided herein, comprising the step of adding a dimerization agent (e.g., tamoxifen or endoxifen, preferably endoxifen) as described herein to said proteins.

The present invention further relates to a method for preparing an inducible T cell receptor (iTCR), comprising the step of introducing the nucleic acid sequence A and the nucleic acid sequence B as described and provided herein, the expression cassette as described and provided herein, or the vector as described and provided herein in vitro into a host cell under conditions allowing the expression of the nucleic acid sequence A and the nucleic acid sequence B. Suitable transformation/transduction methods and expression methods are known in the art and also described herein.

The present invention further relates to the use of the combination or compositions as described and provided herein, the expression cassette as described and provided herein, or the vector as described and provided herein for generating modified T cells, e.g. T lymphocytes.

The present invention further relates to the combination or composition as described and provided herein, the expression cassette as described and provided herein, the vector as described and provided herein, the host cell as described and provided herein, or the protein as described and provided herein, for use in T cell therapy.

The present invention further relates to the combination or composition as described and provided herein, the expression cassette as described and provided herein, the vector as described and provided herein, the host cell as described and provided herein, or the protein as described and provided herein, for use in treating cancer. Cancers which may be treated in this context comprise all kinds of cancers, particularly solid cancers (e.g., on-small cell lung cancer, breast cancer, colorectal cancer, pancreatic cancer, ovarian cancer, skin cancer, prostate cancer, cancer of the brain or nervous system, head and neck cancer, testicular cancer, lung cancer, liver cancer, kidney cancer, bladder cancer, gastrointestinal cancer, bone cancer, cancer of the endocrine system, cancer of the lymphatic system, fibrosarcoma, neurectodermal tumor, mesothelioma, epidermoid carcinoma, or Kaposi's sarcoma), and blood cancers (leukemias).

The present invention further relates to pharmaceutical compositions comprising the combination composition as described and provided herein, the expression cassette composition as described and provided herein, the vector composition as described and provided herein, the host cell composition as described and provided herein, or the protein composition as described and provided herein.

The term "pharmaceutical composition" particularly refers to a composition suitable for administering to a human. However, compositions suitable for administration to non-human animals are generally also encompassed by the term. The pharmaceutical composition and its components (i.e. active agents and optionally excipients) are preferably pharmaceutically acceptable, i.e. capable of eliciting the desired therapeutic effect without causing any undesirable local or systemic effects in the recipient. Pharmaceutically acceptable compositions of the invention may for instance be sterile. Specifically, the term "pharmaceutically acceptable" may mean approved by a regulatory agency or other generally recognized pharmacopoeia for use in animals, and more particularly in humans. The active agent described in the foregoing (for instance the host cell or the iTCR) is preferably present in the pharmaceutical composition in a therapeutically effective amount. By "therapeutically effective amount" is meant an amount of the active agent that elicits the desired therapeutic effect. Therapeutic efficacy and toxicity can be determined by standard procedures, e.g. in cell culture or in test animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

The exact dosage of the nucleic acid, protein, vector or host cell will be ascertainable by one skilled in the art using known techniques. Suitable dosages provide sufficient amounts of the active agent of the invention and are preferably therapeutically effective, i.e. elicit the desired therapeutic effect. As is known in the art, adjustments for purpose of the treatment (e.g. remission maintenance vs. acute flare of disease), route, time and frequency of administration, time and frequency of administration formulation, age, body weight, general health, sex, diet, severity of the disease state, drug combination(s), reaction sensitivities, and tolerance/response to therapy may be necessary. Suitable dosage ranges can be determined using data obtained from cell culture assays and animal studies and may include the $ED_{50}$. Typically, dosage amounts may vary from 0.1 to 100000 micrograms, up to a total dose of about 2 g, depending upon the route of administration. Exemplary dosages of the active agent of the invention are in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. Guidance as to particular dosages and methods of delivery is provided in the literature. It is recognized that treatment may require a single administration of a therapeutically effective dose or multiple administrations of a therapeutically effective dose of the active agent of the invention. E.g., some pharmaceutical compositions might be administered every 3 to 4 days, every week, or once every two weeks, or once within a month depending on formulation, half-life and clearance rate of the particular composition. The pharmaceutical composition may optionally comprise one or more excipients and/or additional active agents.

The term "excipient" includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers. It is within the knowledge of the skilled person to select suitable excipients for preparing the desired pharmaceutical composition of the invention. Exemplary carriers for use in the pharmaceutical composition of the invention include saline, buffered saline, dextrose, and water. Typically, choice of suitable excipients will inter alia depend on the active agent used, the disease to be treated, and the desired formulation of the pharmaceutical composition.

The present invention further provides pharmaceutical compositions comprising one or more of the inventive active agents specified above (for instance a host cell or a iTCR construct), and one or more additional active agents that are suitable for treatment and/or prophylaxis of the disease to be treated. Preferred examples of active ingredients suitable for combinations include known anti-cancer drugs such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin; and peptide cytotoxins such as ricin, diphtheria toxin, pseudomonas bacterial exotoxin A, DNAase and RNAase; radio-nuclides such as iodine 131, rhenium 186, indium 111, yttrium 90, bismuth 210 and 213, actinium 225 and astatine 213; prodrugs, such as antibody directed enzyme pro-drugs; immuno-stimulants, such as IL-2, chemokines such as IL-8, platelet factor 4, melanoma growth stimulatory protein, etc., antibodies or fragments thereof such as anti-CD3 antibodies or fragments thereof, complement activators, xenogeneic protein domains, allogeneic protein domains, viral/bacterial protein domains and viral/bacterial peptides. A variety of routes are applicable for administration of the pharmaceutical composition according to the present invention. Typically, administration will be accomplished parentally. Methods of parenteral delivery include topical, intra-arterial, intramuscular, subcutaneous, intramedullary, intrathecal, intraventricular, intravenous, intraperitoneal, intrauterine, intravaginal, sublingual or intranasal administration.

The pharmaceutical compositions of the invention can be formulated in various forms, depending inter alia on the active agent used, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration. Processes known per se for producing medicaments are indicated in 22nd edition of Remington's Pharmaceutical Sciences (Ed. Maack Publishing Co, Easton, Pa., 2012) and may include, for instance conventional mixing, dissolving, granulating, dragee-making, levigating, emulsifying, encapsulating, entrapping or lyophilizing processes. Pharmaceutical compositions comprising, for instance, host cells as described herein will typically be provided in a liquid form, and preferably comprise a pharmaceutically acceptable buffer. After pharmaceutical compositions of the invention have been prepared they can be placed in an appropriate container and labeled for treatment of an indicated condition. Such labeling would for instance include amount, frequency and method of administration.

In view of the foregoing the present invention thus provides a protein (e.g., iTCR), nucleic acid, vector and/or host cell as described herein for use as a medicament. The term "treatment" in all its grammatical forms includes therapeutic or prophylactic treatment of a subject in need thereof. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of diseases.

The terms "subject" or "individual" or "animal" or "patient" are used interchangeably herein to refer to any subject, particularly a mammalian subject, for whom therapy is desired. Mammalian subjects generally include humans, non-human primates, dogs, cats, guinea pigs, rabbits, rats, mice, horses, cattle, cows, and the like. However, it will readily be understood that the protein (e.g., iTCR), nucleic acids, vectors, host cells and pharmaceutical compositions provided herein are especially envisaged for treatment of human subjects.

For therapy, protein (e.g., iTCR), nucleic acids, vectors (such as viral vectors) or host cells of the invention can be administered directly to the subject in need thereof. Said method can comprise the steps of (a) providing one or more of (i) a protein (e.g., iTCR), (ii), a nucleic acid, (iii) a vector, (iv) a host cell, and/or (v) a pharmaceutical composition of the present invention; and (b) administering one or more of (i)-(v) to the subject in need thereof. Optionally, the method can comprise a further step of cancer therapy, e.g. radiation, or administration of one or more anti-cancer agents.

Treatment according to the invention may also comprise the steps of (a) providing a sample of a subject, said sample comprising lymphocytes; (b) providing one or more of the protein (e.g., iTCR), nucleic acid, vector host cell and/or pharmaceutical composition of the invention (c) introducing of one or more of (i) to (v) of step (b) into the lymphocytes of step (a) and, thereby, obtaining modified lymphocytes, (d) administering the modified lymphocytes of step (c) to a subject or patient in need thereof. The lymphocytes provided in step (a) are particularly envisaged to be "effector host cells" as described in the foregoing and are advantageously selected from T cells, NK cells and/or NKT cells, especially $CD8^+$ T cells; and can be obtained in a previous step (a') from a sample—in particular a blood sample—of the subject by routine methods known in the art. It is however also conceivable to use other lymphocytes that are preferably capable of expressing the protein (e.g., iTCR) of the present invention and exert the desired biological effector functions as described herein. Moreover, said lymphocytes will typically be selected for compatibility with the subject's immune system, i.e. they will preferably not elicit an immunogenic response. For instance, it is conceivable to use a "Universal Recipient Cells", i.e. universally compatible lymphocytes exerting the desired biological effector functions that can be grown and expanded in vitro. Use of such cells will thus obviate the need for obtaining and providing the subject's own lymphocytes in step (a). The ex vivo introduction of step (c) can be carried out by introducing a nucleic acid or vector described herein via electroporation into the lymphocytes, or by infecting the lymphocytes with a viral vector, such as a lentiviral or retroviral vector as described previously in the context of the effector host cell. Other conceivable methods include the use of by transfection reagents, such as liposomes, or transient RNA transfection. The transfer of antigen-specific TCR genes into (primary) T cells by e.g. (retro-)viral vectors or transient RNA transfection represents a promising tool for generating tumor-associated antigen-specific T cells that can subsequently be re-introduced into the donor, where they specifically target and destroy tumor cells expressing said antigen.

In view of the above, a further aspect of the present invention is thus the use of a protein (e.g., iTCR), a nucleic acid sequence, a vector and/or a host cell as described elsewhere herein for generating modified lymphocytes. Means and methods for introducing, e.g. a nucleic acid and a vector into the lymphocytes are known in the art and described herein above.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series or minimal amount of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Also, the term "at least" comprises the exact amount and the upper limit, e.g., "at least 5" also encompasses the meaning "exactly 5" or "at least 3" comprises "exactly 3".

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., "about 20" includes 20.

The term "less than", "at least" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Also, "comprising" and variations thereof also includes the meaning "consisting of".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The term "polynucleotide" or "nucleic acid" as used herein comprises a sequence of polyribonucleotides and polydeoxribonucleotides, e.g. modified or unmodified RNA or DNA, each in single-stranded and/or double-stranded form linear or circular, or mixtures thereof, including hybrid molecules. The nucleic acids according to this invention thus comprise DNA (such as dsDNA, ssDNA, cDNA), RNA (such as dsRNA, ssRNA, mRNA, ivtRNA), combinations thereof or derivatives (such as PNA) thereof. The terms "nucleic acid sequence" or "(poly)nucleotide sequence" are used interchangeably herein. Likewise, the terms "amino acid sequence", "polypeptide" or protein may be used interchangeably herein as clear to the skilled person.

A polynucleotide may comprise a conventional phosphodiester bond or a non-conventional bond (e.g., an amide bond, such as found in peptide nucleic acids (PNA)). The polynucleotides of the invention may also contain one or more modified bases, such as, for example, tritylated bases and unusual bases such as inosine. Other modifications, including chemical, enzymatic, or metabolic modifications, are also conceivable, as long as a binding molecule of the invention can be expressed from the polynucleotide. The polynucleotide may be provided in isolated form as defined elsewhere herein. A polynucleotide may include regulatory sequences such as transcription control elements (including promoters, enhancers, operators, repressors, and transcription termination signals), ribosome binding site, introns, or the like.

The present invention further relates to a method for screening or testing iTCR function comprising the steps of introducing a reporter gene (e.g., a fluorescent protein such as GFP, YFP, CFP, eGFP, ieGFP; preferably ieGFP) using a vector (e.g., a lentiviral vector such as, e.g., pCDH) into a host cell (e.g., a TCR⁻ host cell; preferably a T lymphocyte such as, e.g., Jurkat-76), further introducing into the same host cell one or more nucleic acid molecules comprising nucleic acid sequences A and B described and provided herein (preferably on an expression cassette; "iTCR construct") using a vector (e.g., a lentiviral vector such as, e.g., pCDH; preferably the same vector as the reporter gene), incubating said host cell with an antigen peptide recognized by the (i)TCR together with a dimerization agent as described herein (e.g., tamoxifen or endoxifen for estrogen receptor (e.g., ETR2) being the dimerization domain), and comparing the reporter gene signaling with that of a control cell in which the same vector construct(s) have been introduced, except for a human native TCR gene cassette (i.e. TCR constant alpha and beta chains according to SEQ ID NOs. 2 and 4, respectively, with no dimerization domain linked downstream of the constant alpha and beta chains). Incorporation of (i)TCR into the cell membrane can be measured by methods known in the art, e.g., by flow cytometry as exemplified herein (cf., e.g., FIG. 4 and Example 3). Comparable signaling of the host cells treated with the iTCR construct with those cells treated with native TCR indicate successful iTCR function in accordance with the present invention. "Comparable" in this context may mean, e.g., if the signaling of the host cell with the iTCR construct is at least 60%, 70%, 80%, or 90% as strong as that of the host cells with the native TCR construct, preferably at least 93%, 95%, 96%, 98%, 98.5% or 99% as strong as that of the host cells with the native TCR construct.

BRIEF DESCRIPTION OF THE FIGURES

FIG. 11: TCR Alpha constant region using the amino-acid numbering nomenclature according to IMGT for human constant alpha region:
www.imgt.org/IMGTrepertoire/Proteins/alleles/ index.php?species=Homo%20sapiens&group=TRAC&gene=TRAC1. As depicted:
SEQ ID NO: 13-(DNA) TRAC*01 exon1; length 1-47
SEQ ID NO: 14-(DNA) TRAC*01 exon1; length 1-42
SEQ ID NO: 15-(DNA) TRAC*01 exon1; length 1-30
SEQ ID NO: 16-(DNA) TRAC*01 exon1; length 1-42
SEQ ID NO: 17-(DNA) TRAC*01 exon1; length 1-45
SEQ ID NO: 18-(DNA) TRAC*01 exon1; length 1-30
SEQ ID NO: 19-(DNA) TRAC*01 exon1; length 1-37
SEQ ID NO: 20-(AMINO ACID) TRAC*01 exon1; length 1-16
SEQ ID NO: 21-(AMINO ACID) TRAC*01 exon1; length 1-14
SEQ ID NO: 22-(AMINO ACID) TRAC*01 exon1; length 1-10
SEQ ID NO: 23-(AMINO ACID) TRAC*01 exon1; length 1-14
SEQ ID NO: 24-(AMINO ACID) TRAC*01 exon1; length 1-15
SEQ ID NO: 25-(AMINO ACID) TRAC*01 exon1; length 1-10
SEQ ID NO: 26-(AMINO ACID) TRAC*01 exon1; length 1-12
SEQ ID NO: 27-(DNA) TRAC*01 exon2; length 1-47
SEQ ID NO: 28-(AMINO ACID) TRAC*01 exon2; length 1-15
SEQ ID NO: 29-(DNA) TRAC*01 exon3; length 1-47
SEQ ID NO: 30-(AMINO ACID) TRAC*01 exon3; length 1-35

FIG. 12: TCR Beta constant region using the amino acid numbering nomenclature according to IMGT for human constant beta region allele C1:
www.imgt.org/IMGTrepertoire/Proteins/alleles/ index.php?species=Homo%20sapiens&group=TRBC&gene=TRBC1. As depicted:
SEQ ID NO: 31-(DNA) TRBC1*01 exon1; length 1-69
SEQ ID NO: 32-(DNA) TRBC1*01 exon1; length 1-45
SEQ ID NO: 33-(DNA) TRBC1*01 exon1; length 1-48
SEQ ID NO: 34-(DNA) TRBC1*01 exon1; length 1-45
SEQ ID NO: 35-(DNA) TRBC1*01 exon1; length 1-57
SEQ ID NO: 36-(DNA) TRBC1*01 exon1; length 1-124
SEQ ID NO: 37-(AMINO ACID) TRBC1*01 exon1; length 1-23
SEQ ID NO: 38-(AMINO ACID) TRBC1*01 exon1; length 1-15
SEQ ID NO: 39-(AMINO ACID) TRBC1*01 exon1; length 1-16
SEQ ID NO: 40-(AMINO ACID) TRBC1*01 exon1; length 1-15
SEQ ID NO: 41-(AMINO ACID) TRBC1*01 exon1; length 1-19
SEQ ID NO: 42-(AMINO ACID) TRBC1*01 exon1; length 1-41
SEQ ID NO: 43-(DNA) TRBC1*01 exon2; length 1-19
SEQ ID NO: 44-(AMINO ACID) TRBC1*01 exon2; length 1-6
SEQ ID NO: 45-(DNA) TRBC1*01 exon3; length 1-108
SEQ ID NO: 46-(AMINO ACID) TRBC1*01 exon3; length 1-36
SEQ ID NO: 47-(DNA) TRBC1*01 exon4; length 1-18
SEQ ID NO: 48-(DNA) TRBC1*01 exon4; length 1-6

The following Examples illustrate the present invention, however, without limiting the scope of the invention and the claims.

EXAMPLES

Abbreviations and Synonyms

APC Antigen presenting cells
Blue fluorescence protein BFP
ER Endoplasmic reticulum
ERT2 Estrogen receptor (mutated variant)
GFP Green fluorescence protein
iTCR Inducible TCR
ieGFP Inducible enhanced GFP
LCL Lymphoblastoid cell line
PBL Peripheral blood lymphocytes
TCR T cell receptor
4-OH-Tamoxifen 4-Hydroxytamoxifen Example 1

Rendering a T Cell Receptor Inducible

Figure 1:
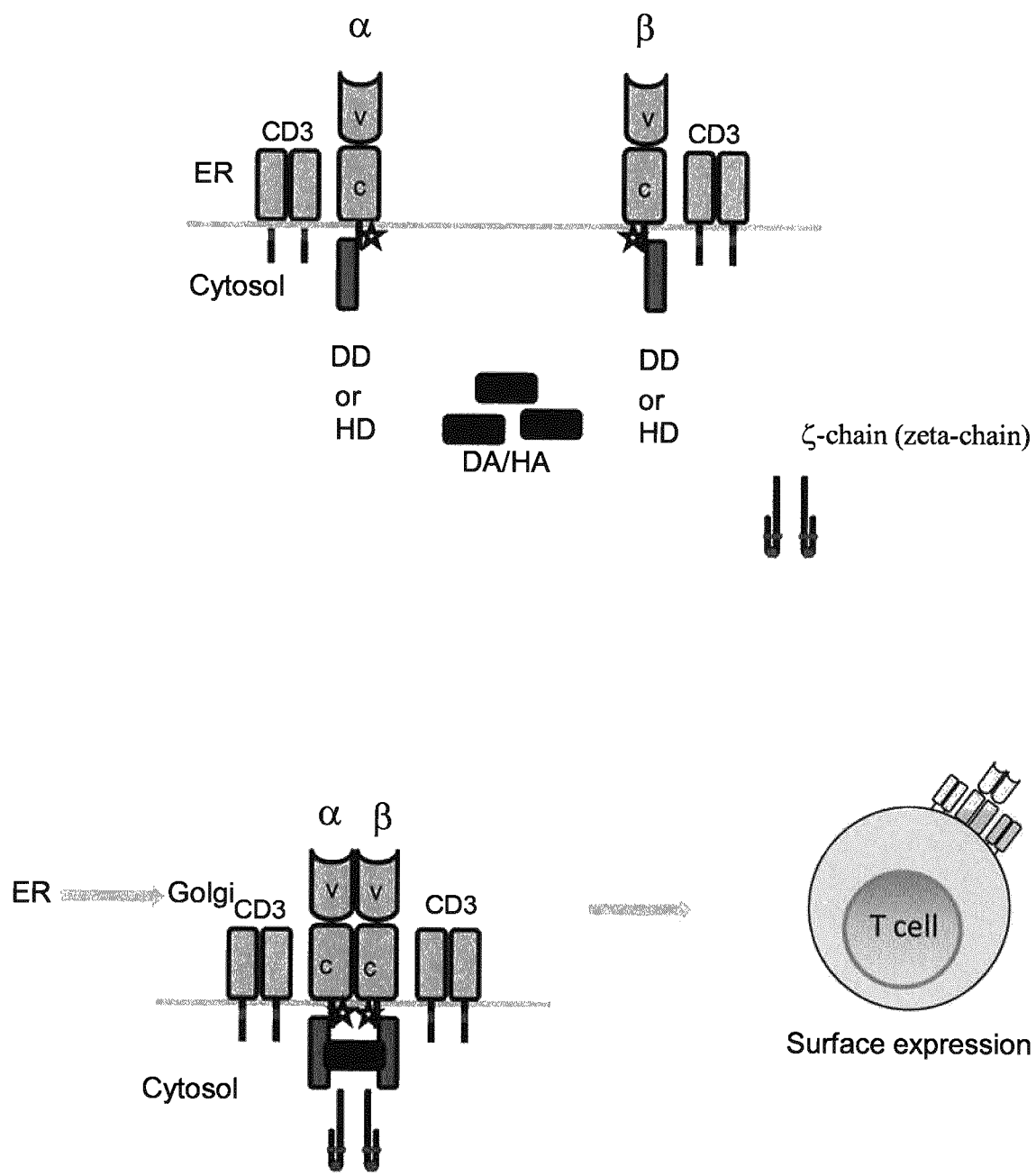
FIG. 1 shows a schematic overview of the inducible TCR. Point mutations ("asterisk") are introduced in the constant ("c") alpha ("α") and beta ("β") chains of a given TCR. Due to the mutations, the TCR alpha-CD3 and TCR beta-CD3 complexes cannot pair in the endoplasmic reticulum. Dimerizing domains ("DD") or alternatively heterodimerizing domains ("HD") are inserted in the c-terminal end of both constant alpha and beta chains of the same TCR. Upon introduction of the dimerizing or heterodimerizing agent ("DA or HA"), pairing of alpha and beta chains and subsequent formation of the functional cluster comprising CD3 ("CD3") and TCR, including the CD3 zeta-chain ("-chain, zeta-chain") can occur and accordingly the TCR can be expressed on the surface of the cell.

With the goal to impair TCR alpha and beta chains pairing the inventors searched for amino acid mutations in the TCR alpha constant and TCR beta constant regions, that would impair TCR alpha and beta chains pairing but would not disturb pairing of the TCR alpha chain with CD3 epsilon and CD3 delta and pairing of the TCR beta chain with CD3 gamma and CD3 epsilon. To identify such amino acids, the inventors conducted a vast search of the literature and considered the crystal structure of known TCRs to retain unaltered interaction of TCR alpha and beta chains with CD3 subunits (Tables 1 and 2). To render the TCR in question inducible, dimerizing (e.g. ERT2) or heterodimerizing (e.g. FKBP, FRB) domains are inserted in the C-terminus of the respective mutated non-pairing alpha and beta constant regions. By exposing cells bearing this iTCR to a dimerizing agent (e.g. 4-hydroxytamoxifen, 4-(1-[4-(Dimethylaminoethoxy)phenyl]-2-phenyl-1-butenyl)phenol, Sigma-Aldrich) or a heterodimerizing agent (e.g. AP21967, 23,27-Epoxy-3H-pyrido[2,1-c][1,4]oxaazacyclohentriacontine; Sigma-Aldrich), TCRα-CD3εδ complex should pair with TCRβ-CD3εγ complex in the endoplasmic reticulum and subsequently TCRα-CD3εδ-TCRβ-CD3εγ should be assembled with CD3ζ in the Golgi apparatus and transported to the cell surface (Feige M J., et al. J Biol Chem. 2015 Oct. 30; 290(44):26821-31). Once the iTCR is on the cell surface it should recognize its pMHC complex presented by antigen presenting cells (APC) equivalently to the original, non-inducible TCR (FIG. 1).

Example 2

Figure 2:
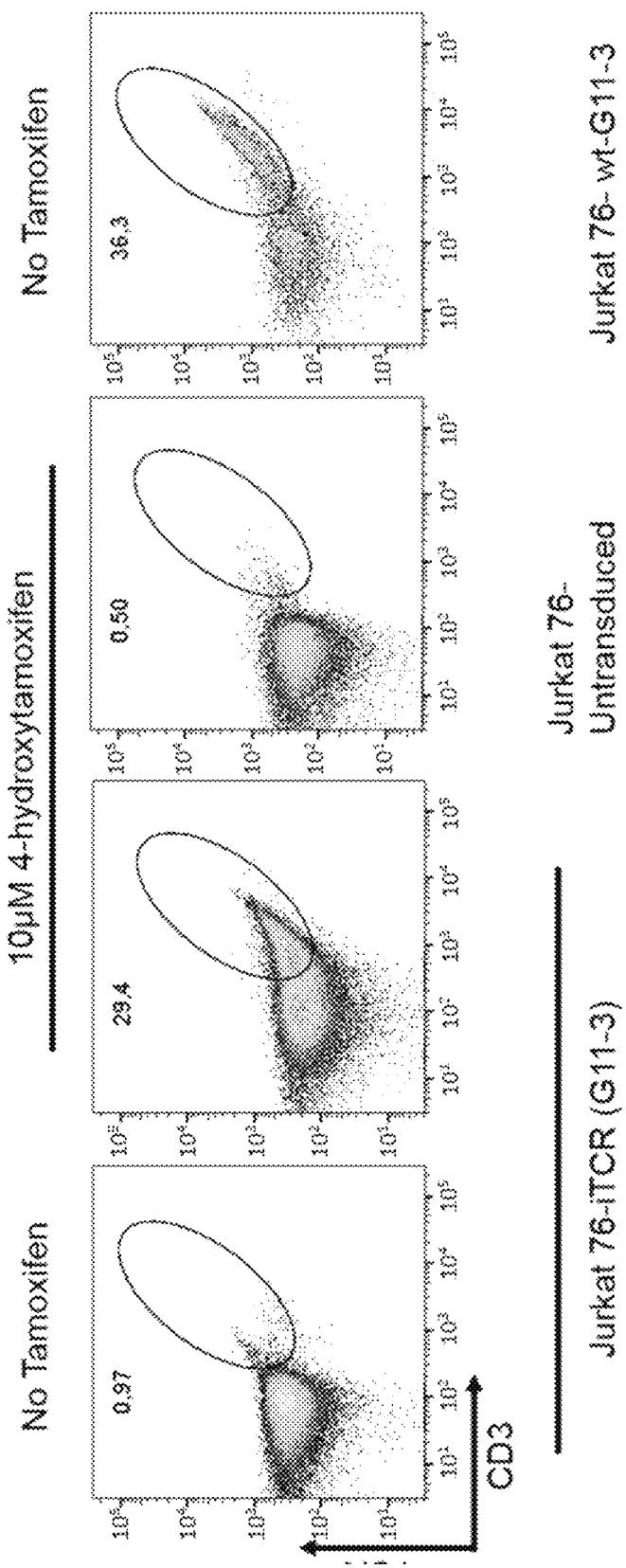
FIG. 2 shows TCR⁻ Jurkat-76 (Jurkat 76 cells are a TCR α- and β-derivative of the CD8-negative human T cell lymphoma Jurkat cell line, kindly provided by M. Heemskerk) cells transduced with the inducible TCR G11-3 (iTCR-G11-3, MHC-II restricted TCR) and tested by flow cytometry for membrane expression of CD3-TCR complex 6 h after induction with 10 µM 4-hydroxytamoxifen (4-hydroxytamoxifen, 4-(1-[4-(Dimethylaminoethoxy)phenyl]-2-phenyl-1-butenyl)phenol, Sigma-Aldrich, stock of 5 mM in DMSO). 4-hydroxytamoxifen was diluted to 10 µM in cell culture medium containing the cells (middle plots) or no 4-hydroxytamoxifen was added ("No tamoxifen", far left and far right plots). Untransduced Jurkat-76 cells were used as negative control for TCR expression and Jurkat-76 tansduced with wt G11-3 (Milosevic S. et al., J Virol 2006 Nov 80(21):10357-64) were used as positive control for G11-3 TCR expression. Cells were stained with anti-CD3-PECy7 and anti panTCR-PE. Plots were generated using the analysis tool FlowJo V10.
Figure 3A:
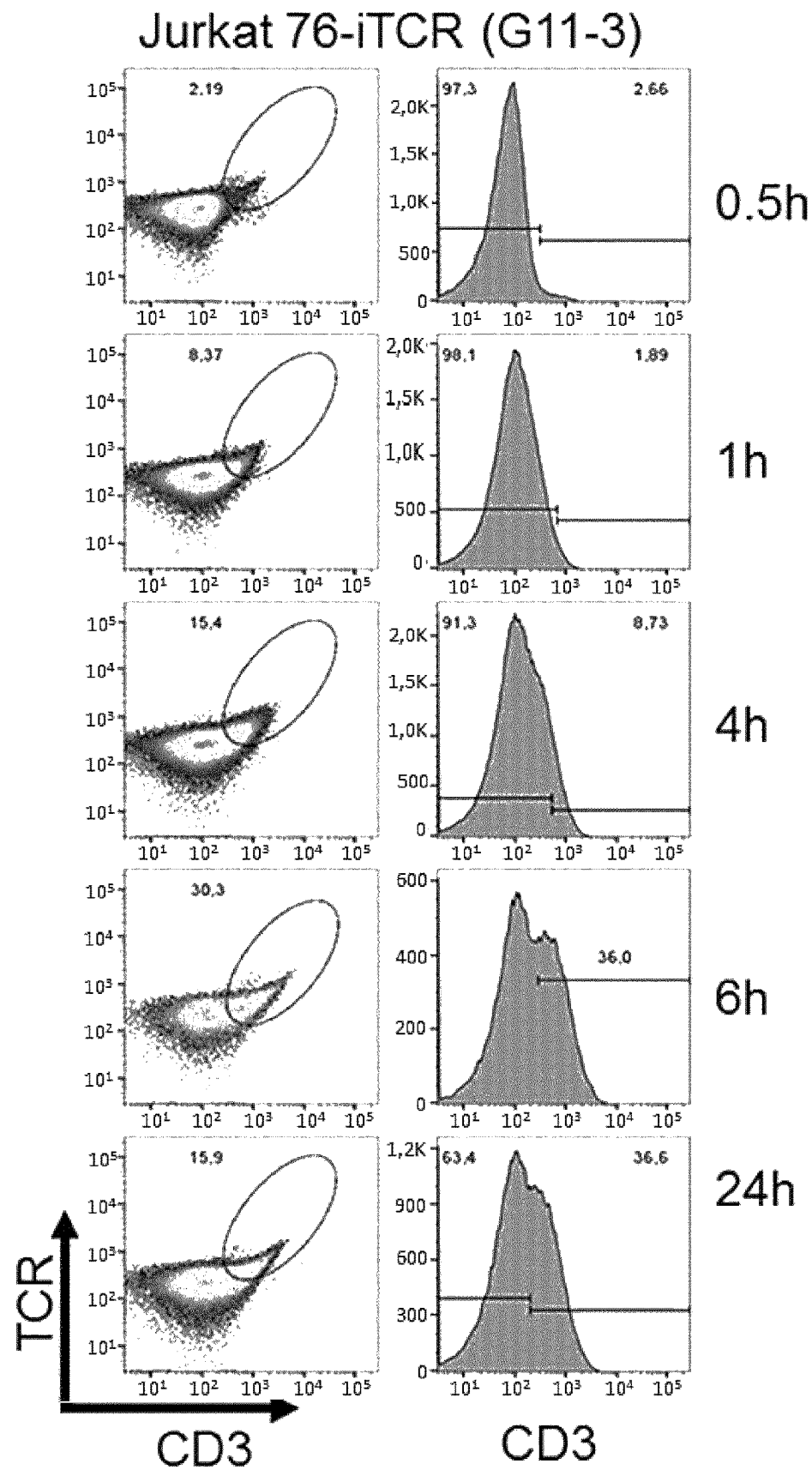
FIG. 3a shows TCR⁻ Jurkat-76 cells transduced with iTCR-G11-3 and assessed for membrane expression of CD3-TCR complex by flow cytometry after induction with 10 µM 4-hydroxytamoxifen or without tamoxifen. Untransduced TCR⁻ Jurkat-76 cells were used as negative control for TCR expression. Cells were stained with anti-CD3-PECy7 and anti-panTCR-PE and flow cytometry was performed 0.5 h, 1 h, 4 h, 6 h and 24 h after 4-hydroxytamoxifen treatment.
Figure 3A:
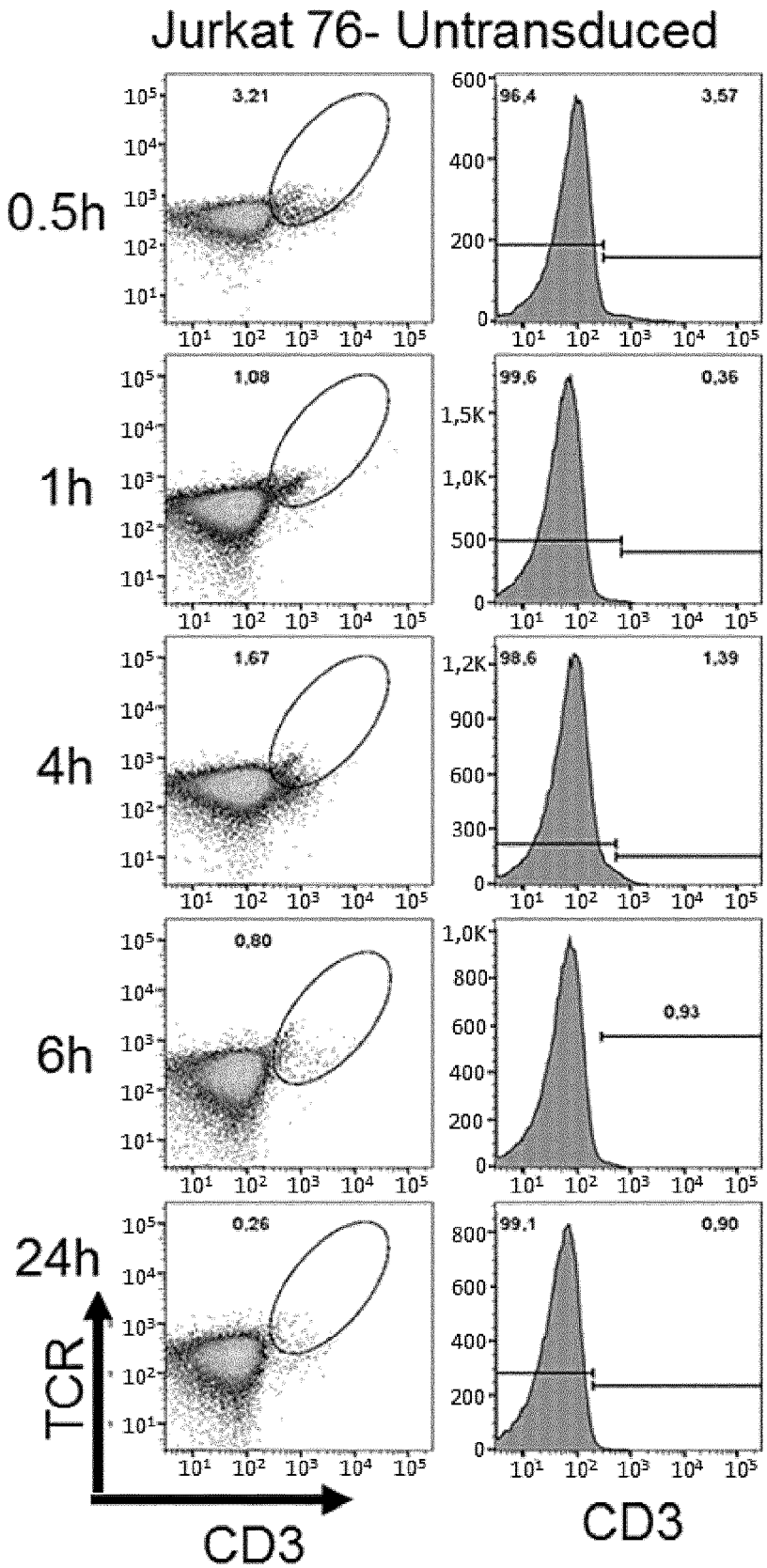
Figure 3B:
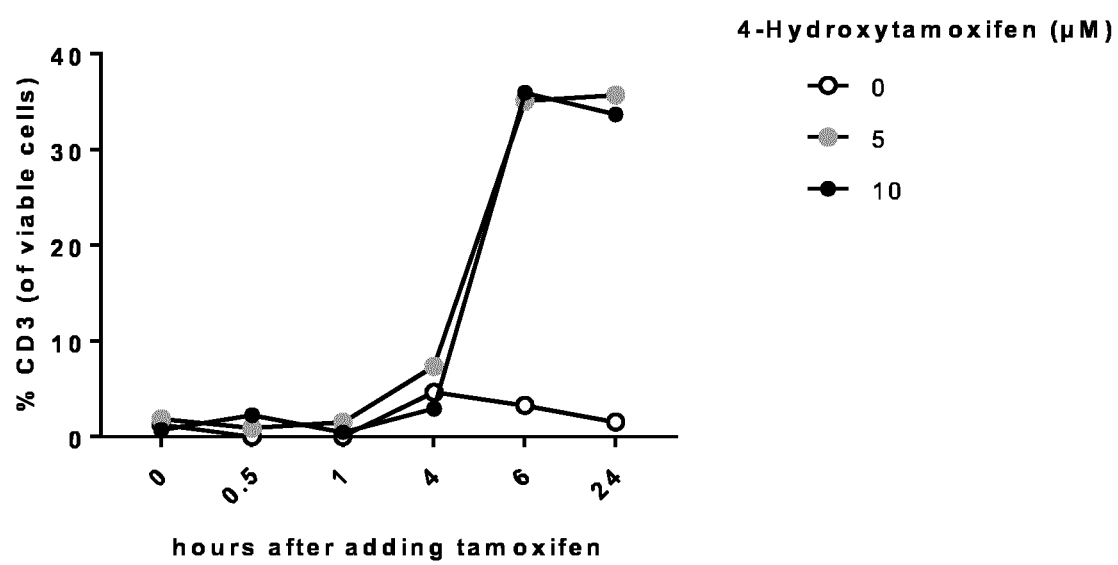
FIG. 3b shows the kinetics of iTCR-G11-3 induction over time (0.5 h, 1 h, 4 h, 6 h and 24 h) using either 5 µM or 10 µM 4-hydroxytamoxifen. Cells were stained with anti-CD3-PECy7 and anti-panTCR-PE and flow cytometry was performed 0.5 h, 1 h, 4 h, 6 h and 24 h after 4-hydroxytamoxifen treatment. Graph was plotted using graphPad Prism 7. Plots were generated using the analysis tool FlowJo V10.

Testing for Impairment of MHC Class II-Restricted iTCR Alpha and Beta Chains Pairing and Induction of Alpha and Beta Pairing Using 4-hydroxytamoxifen in Jurkat-76 Cells A synthetic cassette containing the iTCR-G11-3 was cloned into the lentiviral vector pCDH and transduced into $0.5 \times 10^6$ TCR$^{-/-}$ Jurkat-76 cells (FIGS. 2-6). The iTCR-G11-3 TCR cassette contains the V-alpha and V-beta sequences of the MHC class II restricted TCR G11-3 (Milosevic S. et al., J Virol 2006 Nov 80(21):10357-64), the mutations in the alpha and beta-constant regions shown in Table 1 and ERT2 in the C-terminus of each alpha and beta constant regions. ERT2 is the mutated form of the human ligand-binding domain of estrogen receptor which can bind tamoxifen active metabolites but not estradiol (Feil R., et al., Biochem Biophys Res Commun. 1997 Aug. 28;237(3):752-7). The ERT2 nucleotide and amino acid sequences are depicted in SEQ ID NO: 7 and 8, respectively. Lack of expression of iTCR-G11-3 was tested by staining non-induced Jurkat cells carrying iTCR-G11-3 with anti-CD3 (CD3-PECy7, SK7, 557851, BD) and anti-TCR (panTCR-PE, IP26, B49177, Beckman Coulter) using flow cytometry. Without induction with 4-hydroxytamoxifen no CD3 or TCR could be detected on the surface of the cells. In contrast, by inducing Jurkat cells carrying iTCR-G11-3 with 10 μM 4-hydroxytamoxifen both TCR and CD3 could be detected on the surface of the cells 6 h after induction (FIG. 2). To identify the earliest and latest time-points at which the surface expression of the iTCR can be detected, Jurkat cells carrying iTCR-G11-3 were induced with 5 or 10 μM 4-hydroxytamoxifen and assayed for CD3 and TCR expression at 0.5 h, 1 h, 4 h, 6 h and 24 h after treatment (FIGS. 3a and 3b). Non-induced Jurkats and untransduced TCR$^{-/-}$ Jurkats were used as negative controls for TCR/CD3 surface expression. Surface iTCR expression could be detected as early as 4 h after induction and expression was sustained even 24 h later.

Example 3

Figure 4:
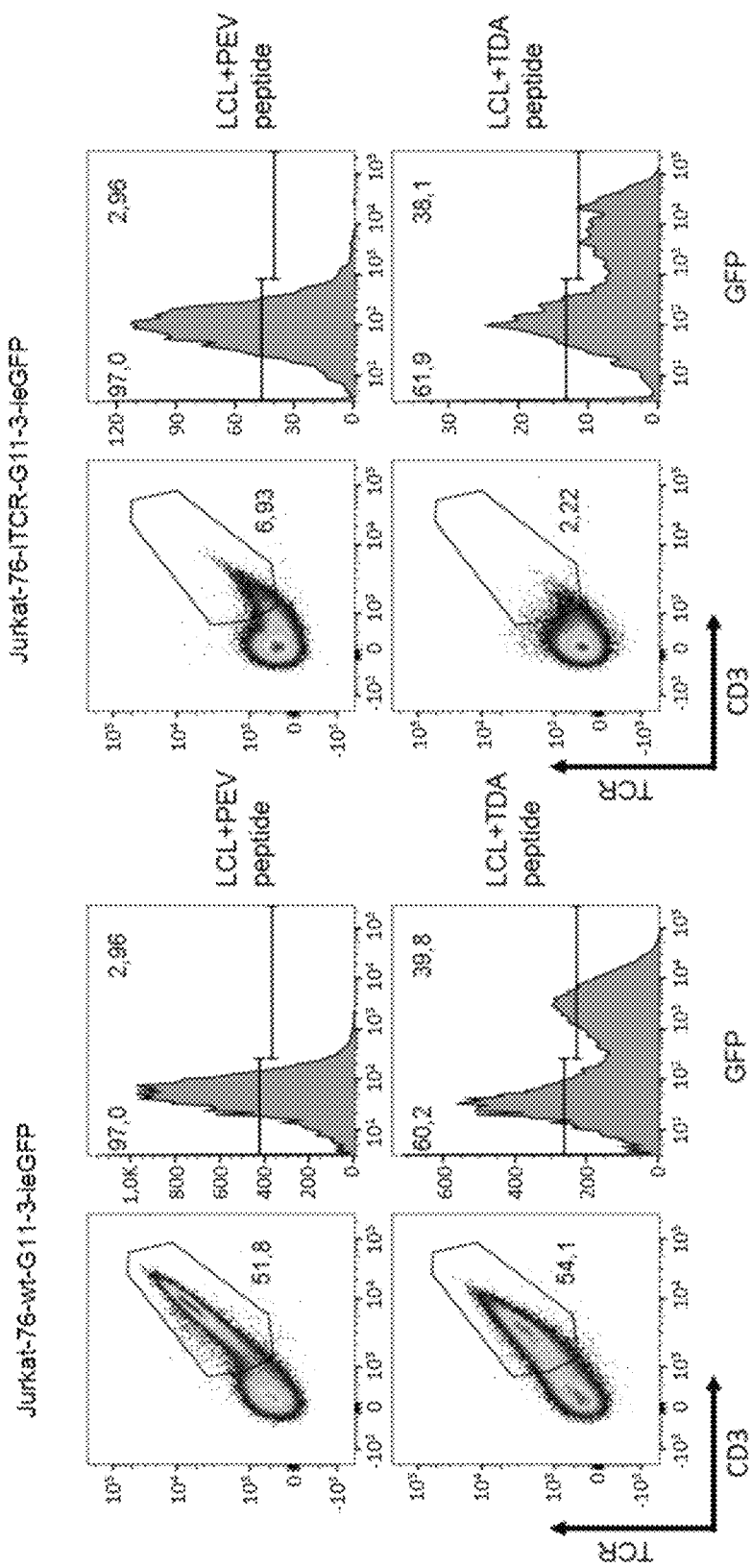
FIG. 4 shows Jurkat-76 transduced with iTCR-G11-3 and with inducible NFAT-responsive GFP reporter (ieGFP) and induced for 6 h with 5 µM 4-hydroxytamoxifen. LCL loaded either with relevant TDAWRFAMNYPRNPT (SEQ ID NO: 9) ("TDA") peptide or with irrelevant PEVWILSPLLRHG (SEQ ID NO: 10) ("PEV") peptide were added to the cultures. The ratio of LCL:Jurkat-76 in the co-cultures was 1:1. Jurkat-76 transduced with wt (wild-type) G11-3 were used as positive control. Flow cytometry was performed 24 h after co-incubation and cells were assessed for CD3, TCR and GFP expression. Plots were generated using the analysis tool FlowJo V10.
Figure 5A:
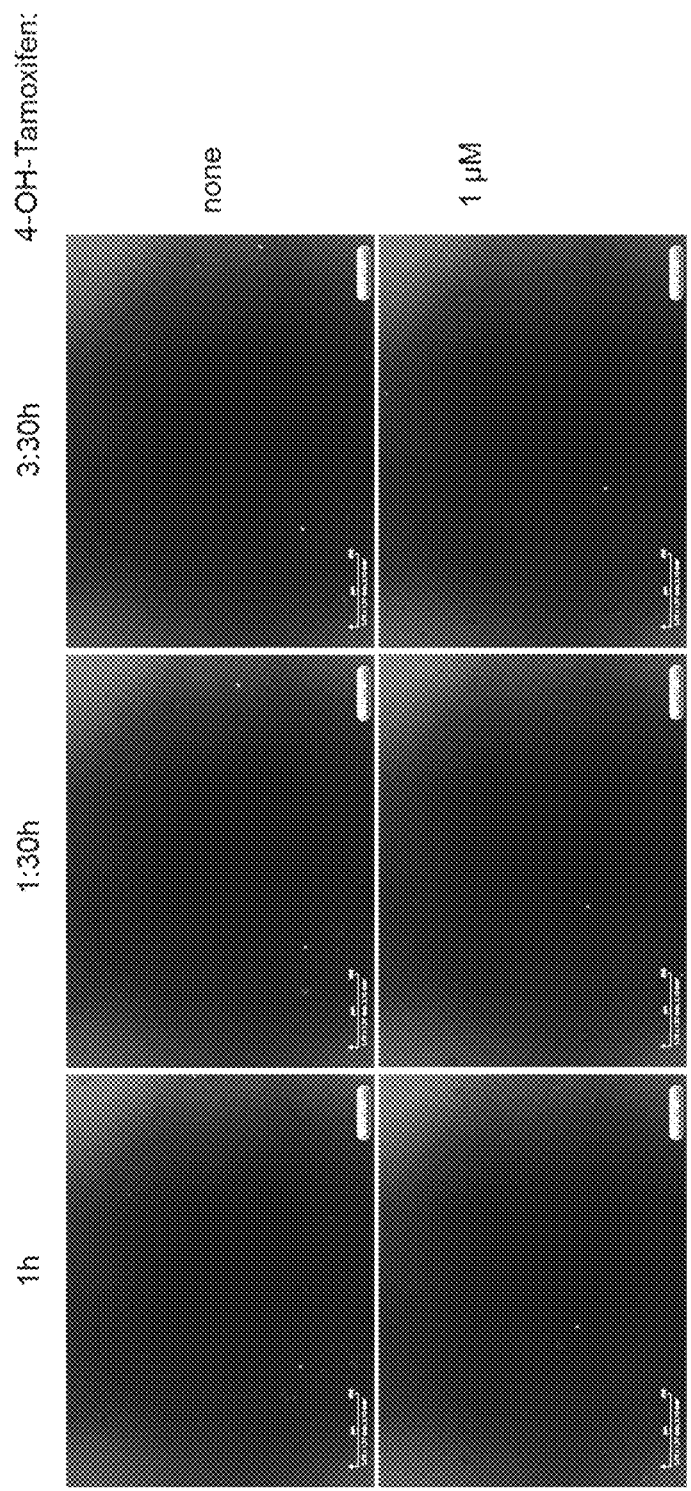
FIG. 5a shows Jurkat-76 transduced with iTCR-G11-3 and with ieGFP and induced overnight with 1 µM 4-hydroxytamoxifen or left untreated (none). LCLs loaded with irrelevant PEV peptide were added to the cultures and GFP induction was followed over time (shown are 1 h, 1.5 h and 3.5 h) using the Incucyte Zoom device (IncuCyte Zoom HD/2CLR System, Essen Bioscience).
Figure 5B:
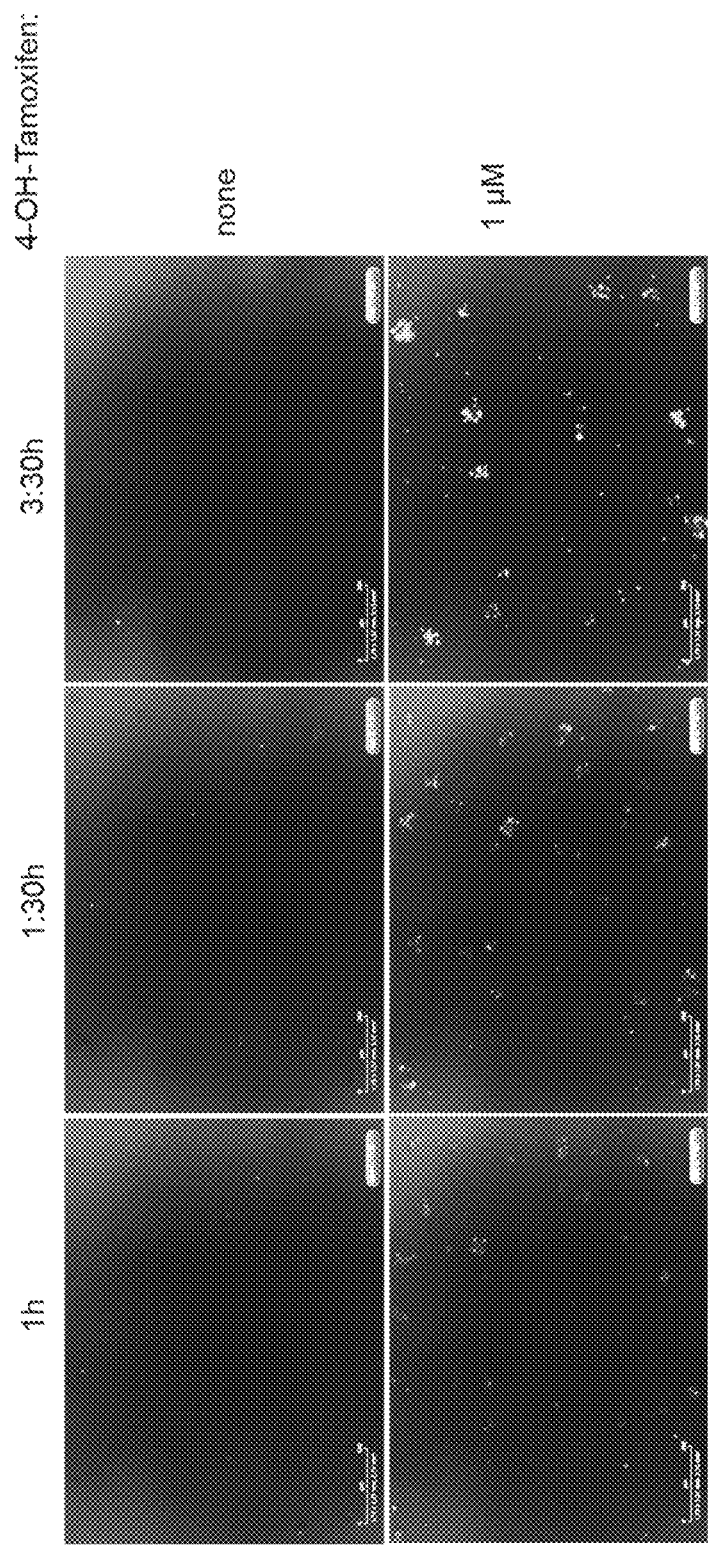
FIG. 5b shows Jurkat-76 transduced with iTCR-G11-3 and with ieGFP and induced overnight with 1 µM 4-hydroxytamoxifen or left untreated (none). LCLs loaded with relevant TDA peptide were added to the cultures and GFP induction was followed over time (shown are 1 h, 1.5 h and 3.5 h) using the Incucyte Zoom device.
Figure 5C:
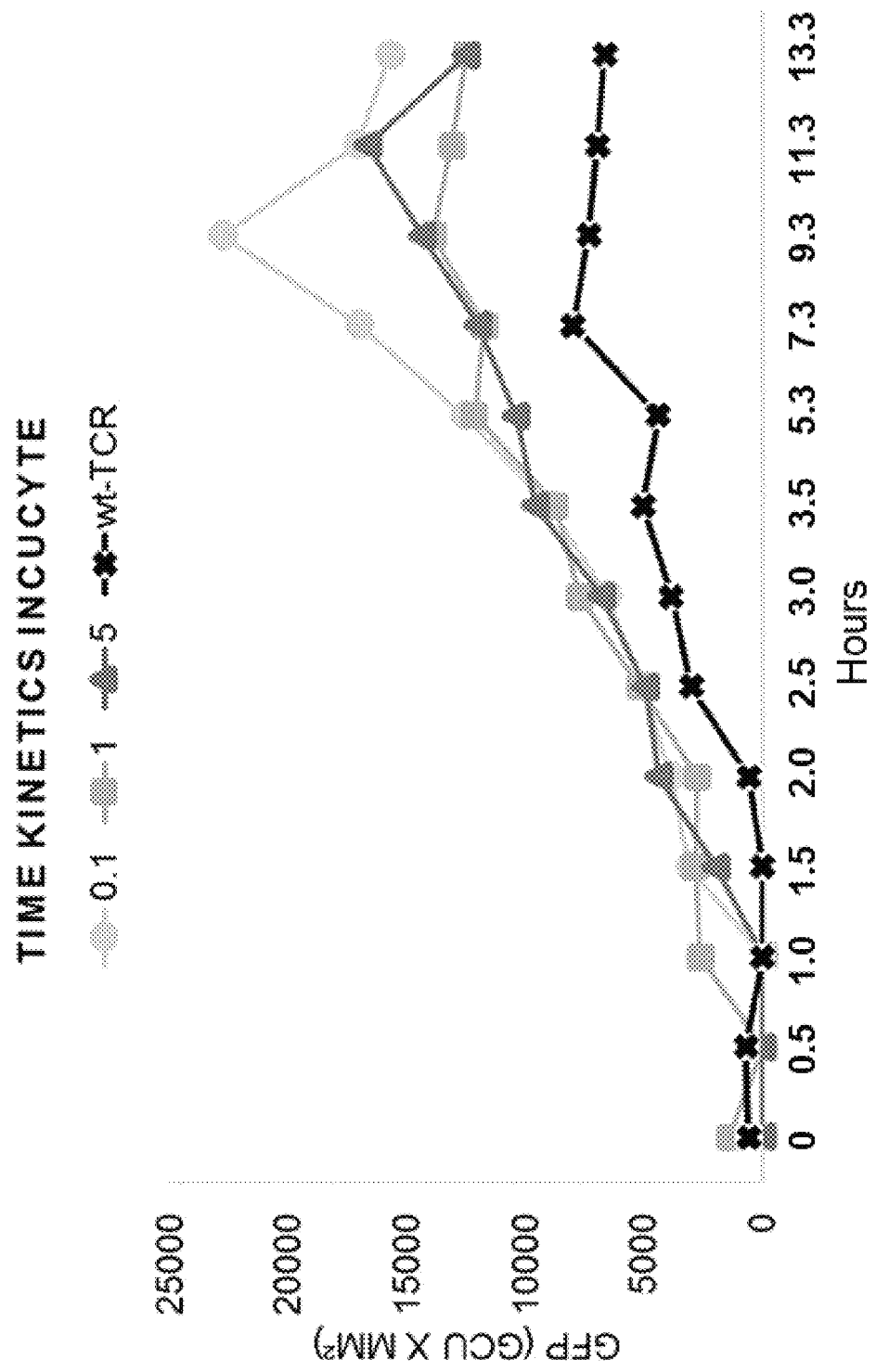
FIG. 5c: Jurkat-76 transduced with iTCR-G11-3 and with ieGFP were induced overnight with 0.1 µM, 1 µM or 5 µM 4-hydroxytamoxifen. LCL loaded with relevant TDA peptide were added to the cultures and GFP induction was followed using the Incucyte Zoom device for 13 h. Jurkat-76 transduced with wt-G11-3 were used as positive control. Shown are the first 14 hours of the kinetics. Graph was plotted using Excel. GFP fluorescence intensity is depicted on the y-axis as green calibration units (GCU)× mm².
Figure 6:
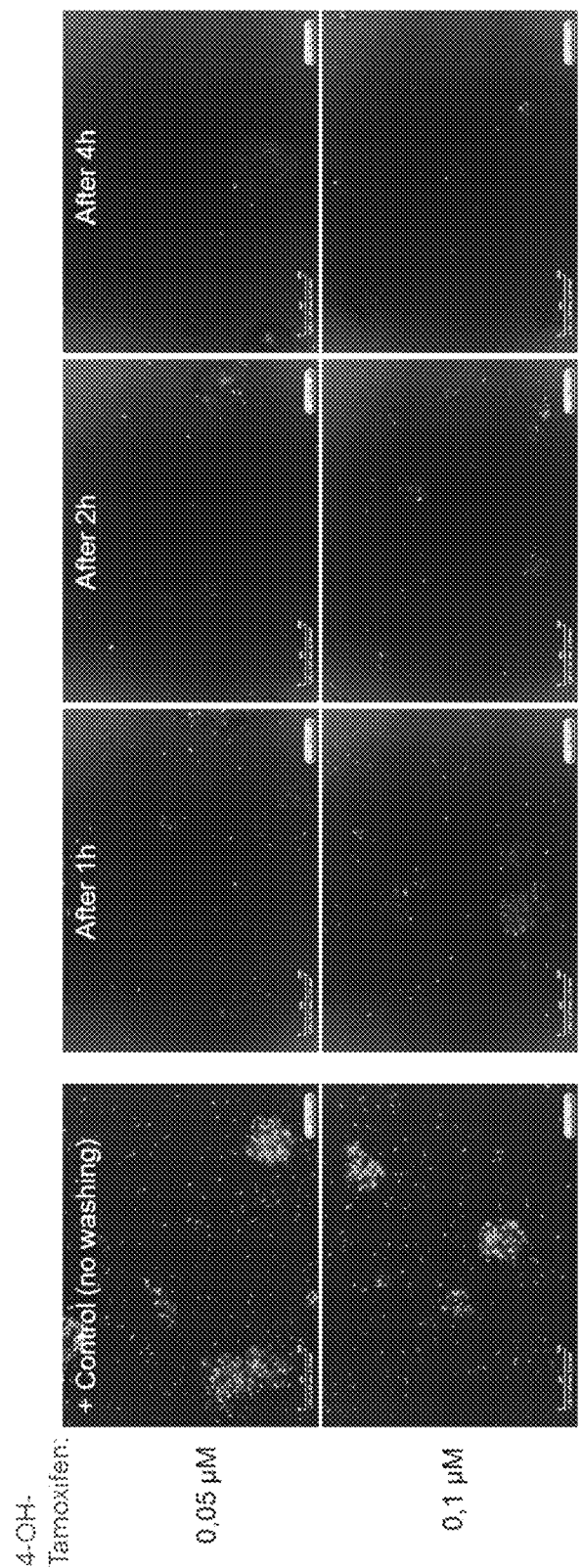
FIG. 6: Jurkat-76 transduced with iTCR-G11-3 and with ieGFP were induced overnight with 0.05 µM or 0.1 µM 4-hydroxytamoxifen. Samples were washed and LCL loaded with relevant TDA peptide were added after 1 h, 2 h and 4 h of washing and GFP induction was followed using the Incucyte Zoom device. For the positive control (pictures in the far left column) LCL loaded with relevant TDA peptide was added to the cultures and no washing was performed.

Testing MHC Class II-Restricted iTCR Function after Induction of iTCR Alpha and Beta Chains Pairing with 4-Hydroxytamoxifen in Jurkat-76 Cells As TCR transduced Jurkat cells in general do not secrete cytokines upon pMHC recognition, the inventors made use of an inducible NFAT-responsive GFP reporter cassette (ieGFP) as read out for functional TCR signaling. The ieGFP cassette was cloned in the lentiviral vector pCDH (System Biosciences) and transduced into 0.5×106 TCR−/− Jurkat-76 cells. The same Jurkat cells carrying ieGFP were then transduced with the lentiviral vector carrying the iTCR-G11-3 cassette (FIGS. 4-6). The wt G11-3 TCR was also transduced in Jurkat cells carrying ieGFP and served as a positive control for G11-3 TCR signaling (FIGS. 4 and 5c). LCL cells (used as antigen presenting cells) loaded with either the irrelevant peptide "PEV" (PEVWILSPLLRHG, SEQ ID NO: 10) or with the peptide "TDA" (TDAWRFAMNYPRNPT, SEQ ID NO: 9) which is recognized by the G11-3 TCR were incubated with either iTCR-G11-3-ieGFP Jurkat cells or with wt-G11-3-ieGFP Jurkat cells. Peptides were loaded at a concentration of 1×10-5M. As expected, a GFP signal, and thus functional TCR signaling, could only be seen for either Jurkat cells expressing wt-G11-3 or Jurkat cells expressing iTCR-G11-3 after induction with 5 μM 4-hydroxytamoxifen and incubation with LCL+TDA (FIG. 4). Flow cytometry analyses was performed staining for anti-CD3 (CD3-PECy7, SK7, 557851, BD) and anti-TCR (panTCR-PE, IP26, B49177, Beckman Coulter).

Example 4

Determination of Speed of iTCR Signalling Post pMHC Recognition and Speed of Switch Off of TCR Signal Cascade Upon Removal of 4-Hydroxytamoxifen To determine how fast iTCR-G11-3 can signal, $1 \times 10^4$ Jurkat cells carrying iTCR-G11-3 and ieGFP were induced overnight (ON) with 1 μM 4-hydroxytamoxifen. To monitor lack of TCR expression without induction, Jurkat cells carrying iTCR-G11-3 and ieGFP were left untreated as control. Either LCL loaded with PEV irrelevant peptide (FIG. 5a) or LCL loaded with TDA relevant peptide (FIG. 5b) were added to the cultures and GFP signal was followed over time using the Incucyte device. GFP signal starts as soon as 1 h after incubation with APC (antigen presenting cells) loaded with relevant peptide (FIGS. 5b and 5c) and the signal continues to increase up to approximately 7 h after incubation (FIG. 5c). Peptides were loaded at a concentration of $1 \times 10^{-5}$M. Interestingly, the GFP signal elicited by the iTCR-G11-3 TCR was always higher over time than the signal elicited by the wt-G11-3 TCR (FIG. 5c). The induction of GFP was not seen when irrelevant peptide was presented to iTCR expressing T cells on LCL serving as APCs.

To analyze how fast the iTCR can be downregulated upon removal of 4-hydroxytamoxifen, Jurkat cells expressing iTCR-G11-3 and ieGFP were first induced overnight with 0.05 μM or 0.1 μM 4-hydroxytamoxifen. The next day the cells were washed free of 4-hydroxytamoxifen or left unwashed (positive control) and incubated with LCL loaded with the relevant TDA peptide either 1 h, 2 h or 4 h after removal of 4-hydroxytamoxifen and subsequently GFP signal was detected using Incucyte (FIG. 6). A reduction in the GFP signal compared to the unwashed control was already visible 1 h after cells induced with 0.05 μM 4-hydroxytamoxifen were washed out of the dimerizing agent and 4 h after washing out 0.1 μM 4-hydroxytamoxifen. Thus, the iTCR could be quickly induced and also quickly downregulated upon removal of the dimerizing agent.

Example 5

Figure 7A:
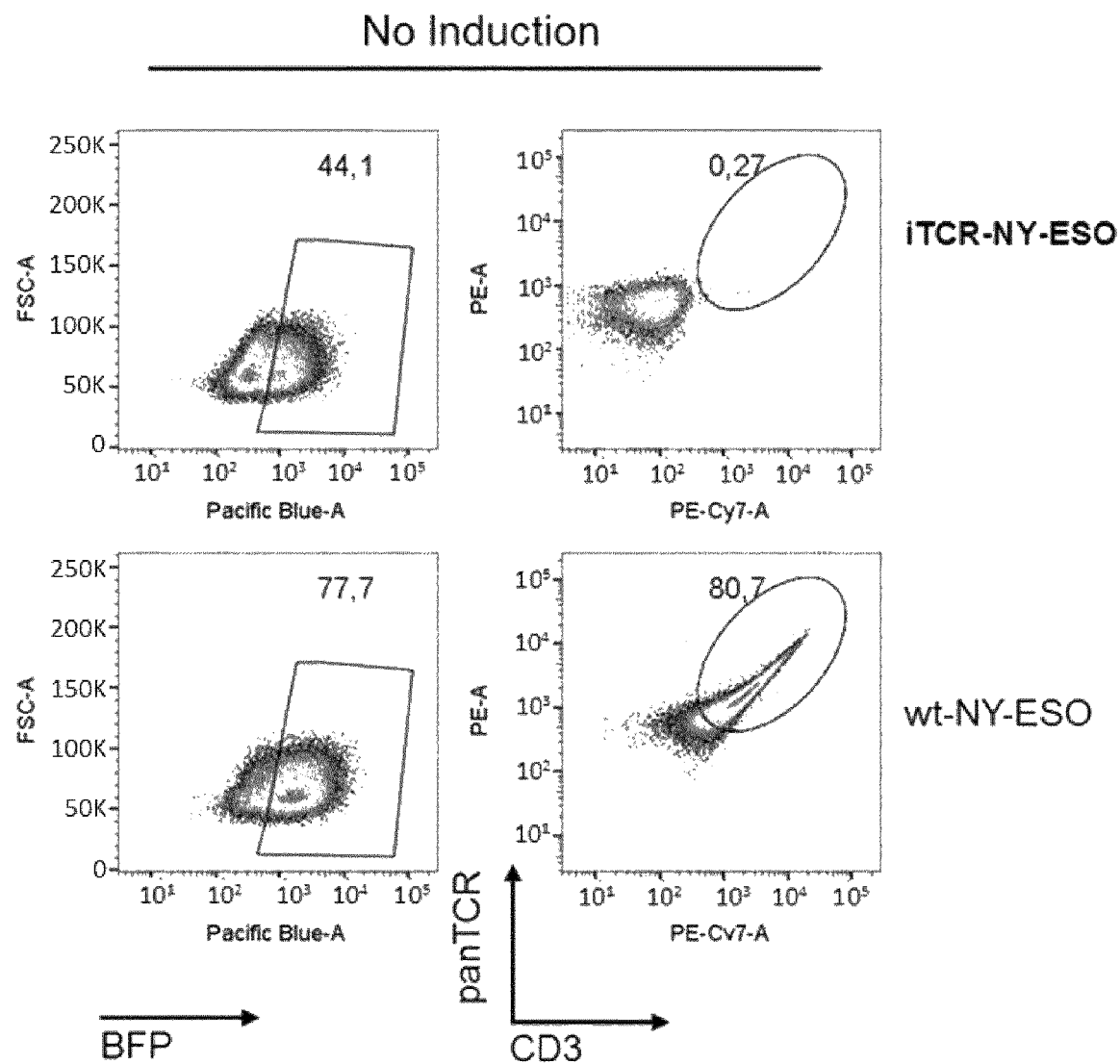
FIG. 7a shows TCR⁻ Jurkat-76 cells transduced with either the inducible TCR iTCR NY-ESO (iTCR-NY-ESO, MHC-I restricted TCR, upper plots) or with wt-NY-ESO TCR (lower plots) and tested by flow cytometry for membrane expression of CD3-TCR complex. Transduced cells also express BFP (blue fluorescent protein, vector encoding for iTCR also contains blue fluorescent protein (mTag-BFP) as reporter gene, which is separately expressed, thus only transduced cells are BFP positive) (plots on the left). Plots on the right show CD3 and TCR staining for BFP+ cells. Cells were stained with anti-CD3-PECy7 and anti-panTCR-PE. Plots were generated using the analysis tool FlowJo V10.
Figure 7B:
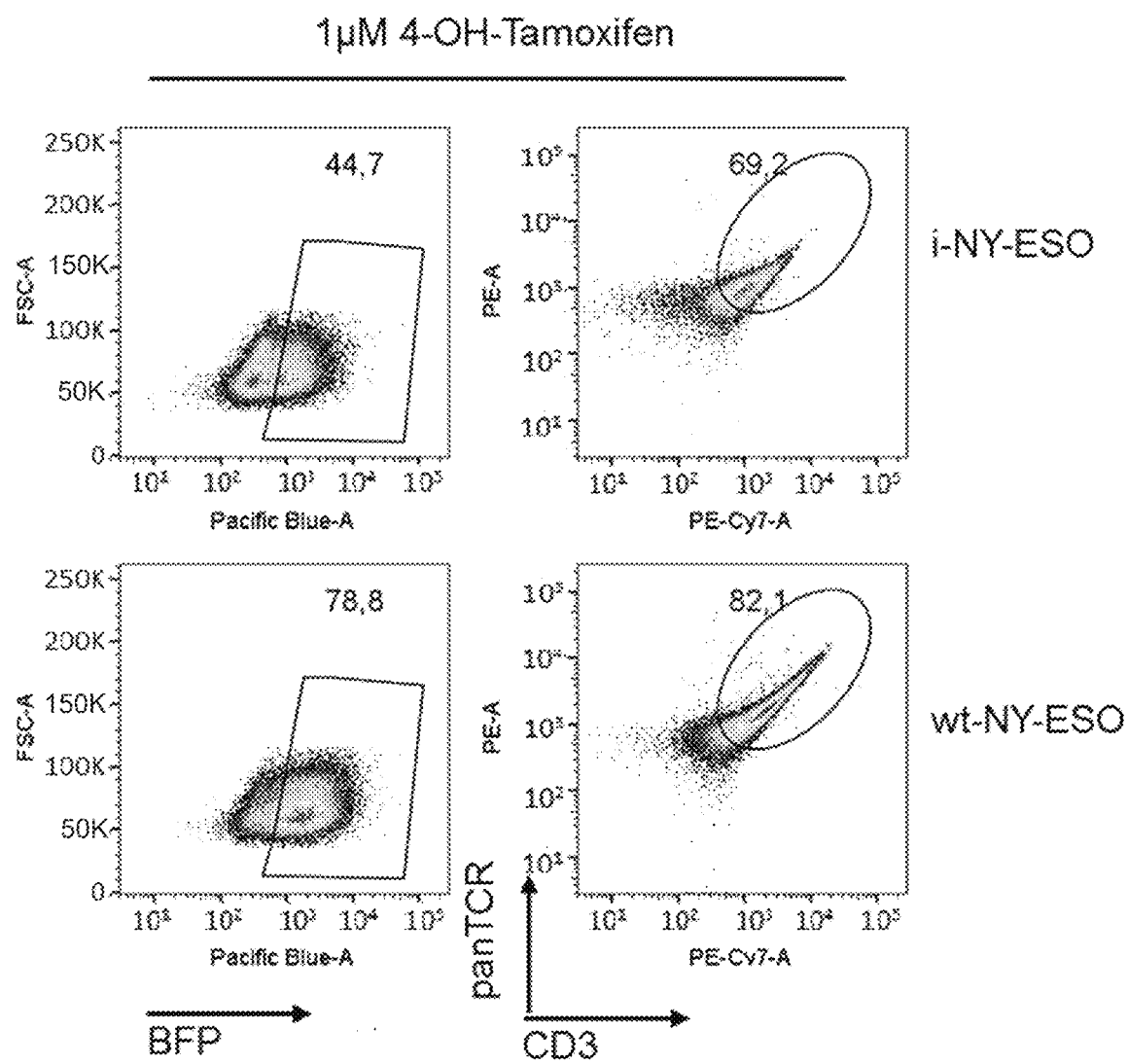
FIG. 7b shows TCR⁻ Jurkat-76 cells transduced with either the inducible TCR NY-ESO (iTCR-NY-ESO, MHC-I restricted TCR, upper plots) or with wt-NY-ESO TCR (lower plots) and induced with 1 µM 4-hydroxytamoxifen (stock of 5 mM in DMSO). 4-hydroxytamoxifen was diluted to 1 µM in cell culture medium containing the cells. Transduced cells also express BFP (plots on the left). Plots on the right show CD3 and TCR staining for BFP+ cells. Cells were stained with anti-CD3-PECy7 and anti-panTCR-PE. Plots were generated using the analysis tool FlowJo V10.
Figure 8A:
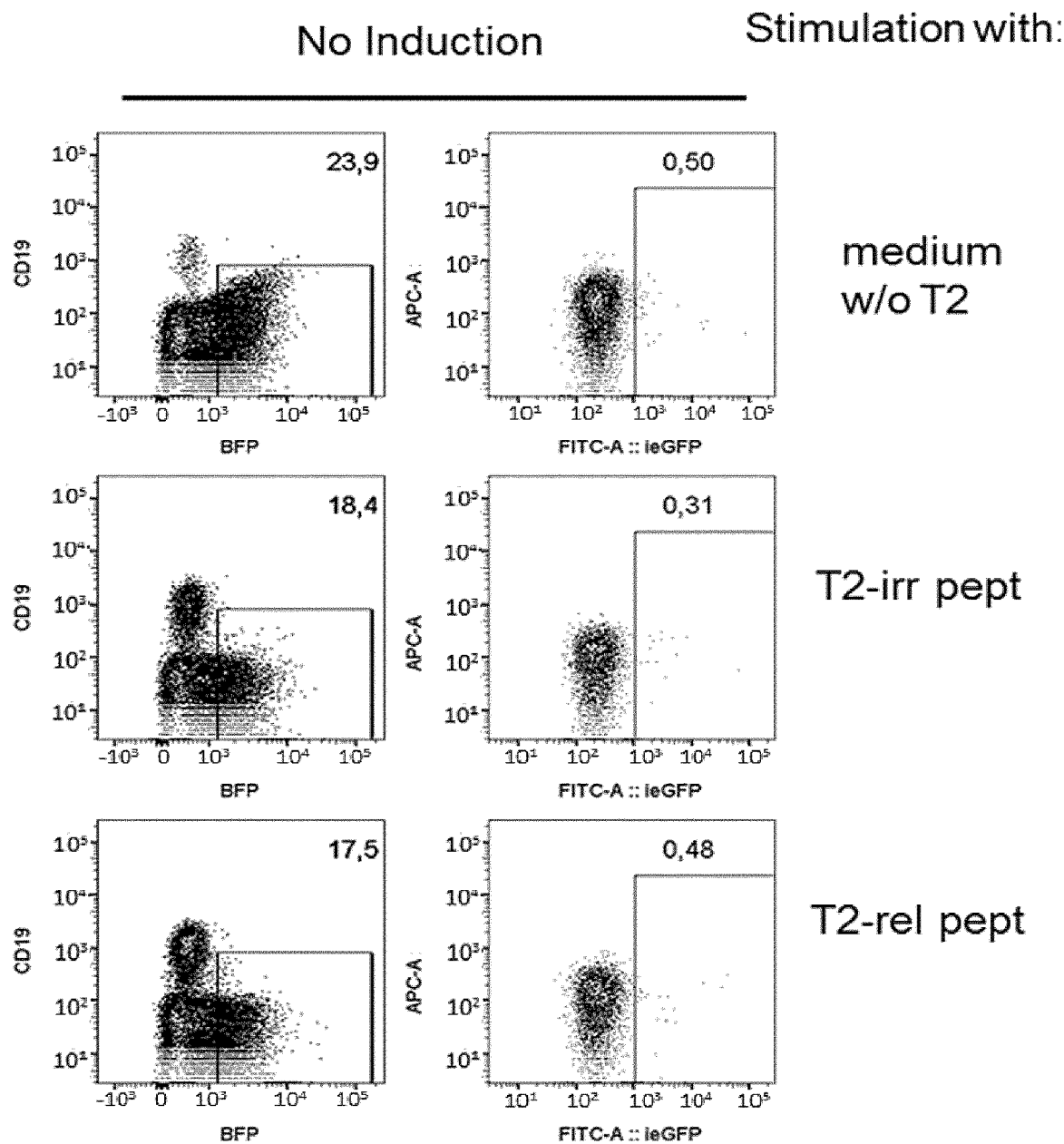
FIG. 8a: Jurkat-76 transduced with iTCR-NY-ESO-mTag-BFP (MHC-I restricted TCR) and with ieGFP were incubated with T2 cells loaded either with irrelevant VLDG-LDVLL peptide (SEQ ID NO: 11) or with relevant peptide SLLMWITQC (SEQ ID NO: 12). The ratio of T2:Jurkat-76 in the co-cultures was 1:1. Flow cytometry was performed 24 h after co-incubation staining for CD19 and determining blue fluorescence, fluorescence in APC and FITC channel. Gating strategy was to gate on CH19⁻ (negative) (thus excluding T2-target cells, which are CD19⁻ (positive)) and BFP+ cells and to determine fluorescence of ieGFP in FITC channel of FACS. Plots were generated using the analysis tool FlowJo V10.
Figure 8B:
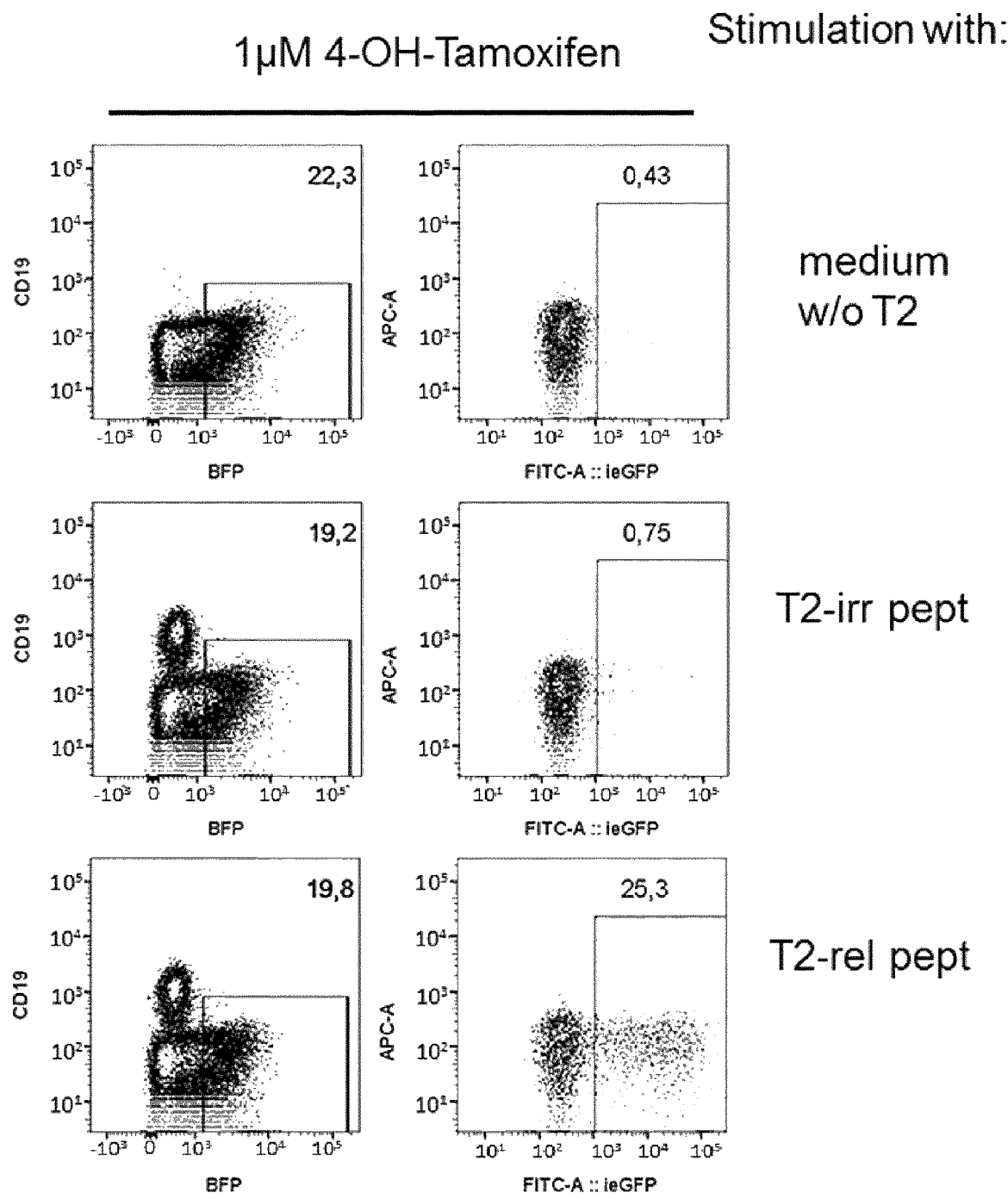
FIG. 8b: Jurkat-76 transduced with iTCR-NY-ESO (MHC-I restricted TCR) and with ieGFP were induced overnight with 1 µM Endoxifen ((E/Z)-Endoxifen hydrochloride hydrate, Sigma-Aldrich)) and were then incubated with T2 cells loaded either with irrelevant VLDG-LDVLL (SEQ ID NO: 11) ("T2-irr. Pept.") peptide or with relevant peptide SLLMWITQC (SEQ ID NO: 12) ("T2-rel. pept."). The ratio of T2:Jurkat-76 in the co-cultures was 1:1. Flow cytometry was performed 24 h after co-incubation and cells were assessed for BFP (transductants), CD3, TCR and GFP expression. Plots were generated using the analysis tool FlowJo V10.

Testing MHC Class I-Restricted iTCR Expression and Function after Induction of iTCR Alpha and Beta Chains Pairing with 4-Hydroxytamoxifen in Jurkat-76 Cells A synthetic cassette containing the iTCR-NY-ESO TCR and mTag-BFP separated by P2A was cloned into the lentiviral vector pCDH and transduced into $0.5 \times 10^6$ TCR$^{-/-}$ Jurkat-76 cells (FIGS. 7 and 8). Since the vector encoding for the iTCR also contains the blue fluorescence protein (mTag-BFP) as reporter gene, which is separately expressed, all transduced cells are BFP positive. The iTCR-NY-ESO TCR cassette contains the V-alpha and V-beta sequences of the MHC class I restricted TCR that recognizes NY-ESO antigen (Benchmark NY-ESO TCR; cf. WO 2005/113595), the mutations in the alpha and beta-constant regions shown in Table 1 and ERT2 in the C-terminus of each alpha and beta constant regions. Lack of expression of iTCR-NY-ESO was tested by staining non-induced Jurkat cells carrying iTCR-NY-ESO with anti-CD3 and anti-TCR for flow cytometry and no CD3 or TCR could be detected on the surface of the cells without induction with 4-hydroxytamoxifen (FIG. 7a). In contrast, by inducing Jurkat cells carrying iTCR-NY-ESO with 1 μM 4-hydroxytamoxifen both TCR and CD3 could be detected on the surface of the cells (FIG. 7b). Flow cytometry analyses was performed staining for anti-CD3 (CD3-PECy7, SK7, 557851, BD) and anti-TCR (panTCR-PE, IP26, B49177, Beckman Coulter). To determine whether iTCR-NY-ESO is functional upon induction, Jurkat cells carrying ieGFP were transduced with the lentiviral vector carrying the iTCR-NY-ESO cassette. The wt NY-ESO TCR was also transduced into Jurkat cells carrying ieGFP and served as a positive control for NY-ESO TCR signaling. T2 cells loaded with either the irrelevant peptide VLDGLDVLL (SEQ ID NO: 11) (FIG. 8a) or with the relevant peptide SLLMWITQC (SEQ ID NO: 12) (FIG. 8b) which is recognized by the NY-ESO TCR were incubated with either iTCR-NY-ESO-ieGFP Jurkats or with wt-NY-ESO-ieGFP Jurkats. Peptides were loaded at a concentration of $1 \times 10^{+5}$ M. As expected, a GFP signal, and thus functional TCR signaling, could only be seen for either Jurkats expressing wt-NY-ESO or Jurkats expressing iTCR-NY-ESO after induction with 1 μM 4-hydroxytamoxifen and incubation with T2+ relevant peptide. Gating strategy was gating on CD19$^{negative}$, BFP positive cells and subsequent determination of ieGFP fluorescence (CD19-APCeF780, HIB 19, 47-0199-42, eBioscience).

Example 6

Figure 9:
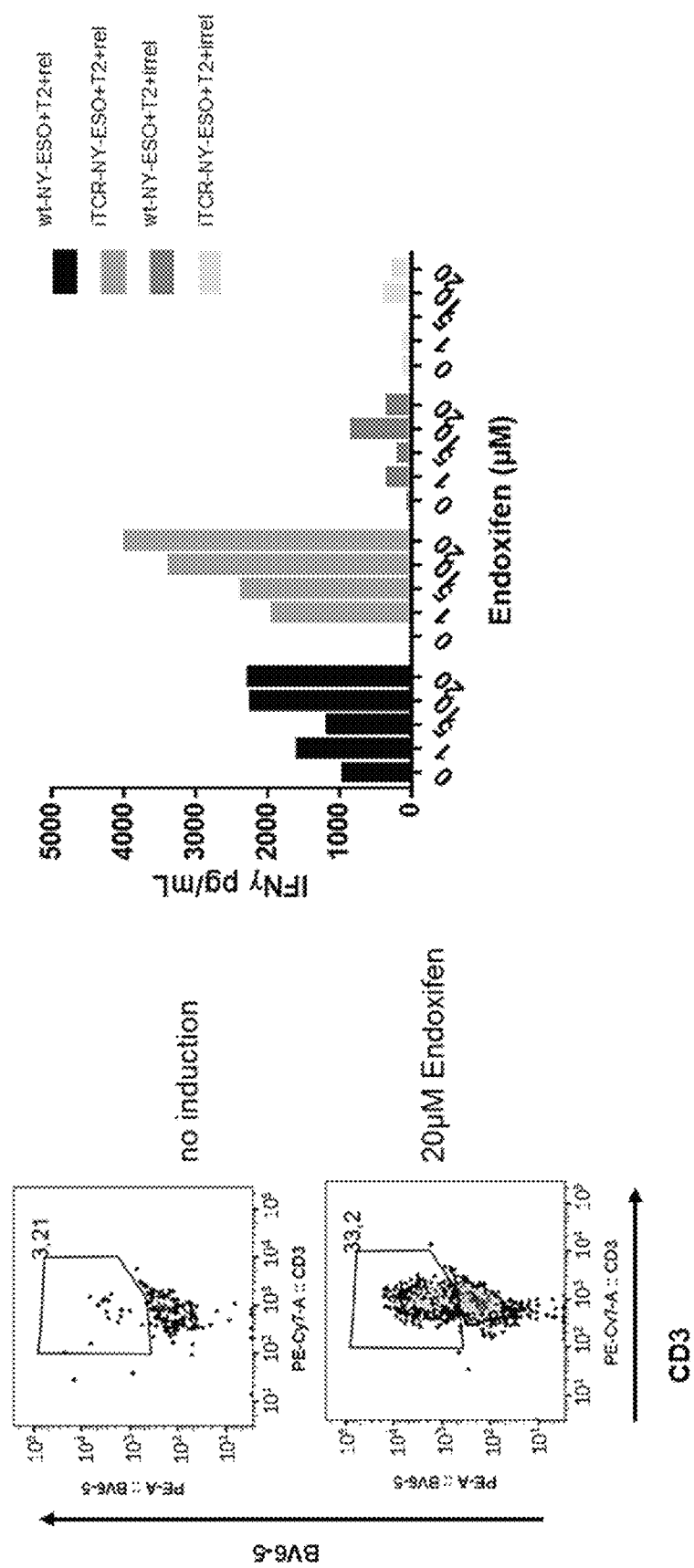
FIG. 9: CD8+ PBL transduced with iTCR-NY-ESO (MHC-I restricted TCR) or CD8+ PBL expressing wt-NY-ESO were induced overnight with 1, 5, 10 or 20 µM Endoxifen or were left uninduced (no Endoxifen). 24 h after induction T2 cells loaded with relevant peptide SLL-MWITQC (SEQ ID NO: 12) or irrelevant peptide VLDG-LDVLL (SEQ ID NO: 11) were added to the cultures. IFN-γ secretion was detected by standard IFN-γ ELISA performed with the culture supernatants 24 h after stimulation with T2 targets. Flow cytometry was performed 48 h after induction and cells were assessed for BFP (transductants), CD3 and BV6-5. Exemplary plots shown are iTCR-NY-ESO transduced CD8+ PBL without induction or with 20 μM Endoxifen. Plots were generated using the analysis tool FlowJo V10. Graph was plotted using graphPad Prism 7.

Testing Mhc Class I-Restricted Itcr Expression and Function after Induction of iTCR Alpha and Beta Chains Pairing with Endoxifen in CD8+PBL PBL from a healthy donor was enriched for CD8$^+$ cells using a commercial cell isolation kit (CD8+untouched) and transduced with the lentiviral vector carrying the iTCR-NY-ESO cassette or with the lentiviral vector carrying wt-NY-ESO as positive control. As induction of the iTCR-NY-ESO with 4-Hydroxytamoxifen did not induce iTCR-NY-ESO in PBL in any of the concentrations tried (data not shown), the inventors used another active Tamoxifen metabolite called Endoxifen. CD8$^+$ cells carrying either iTCR-NY-ESO were induced overnight with 20 μM Endoxifen or left untreated. Cells were then stained for CD3 (CD3-PECy7, SK7, 557851, BD) and the specific V-beta family BV6-5 (antibody: TRBV6-5-PE, IMMU 222, IM2292, Beckman Coulter). Treatment with Endoxifen resulted in induction of iTCR-NY-ESO on the surface of the cells (FIG. 9). Without treatment only the endogenously expressing BV6-5 positive cells can be seen.

To determine whether iTCR-NY-ESO is functional when induced in PBL, T2 cells loaded with the relevant peptide SLLMWITQC (SEQ ID NO: 12) or irrelevant peptide VLDGLDVLL (SEQ ID NO: 11) were incubated with 1, 5, 10 or 20 μM Endoxifen-induced iTCR-NY-ESO CD8$^+$ PBL or with uninduced iTCR-NY-ESO CD8$^+$ PBL or with CD8$^+$ PBL carrying wt-NY-ESO as positive control. Peptides were loaded at a concentration of $1 \times 10^{-5}$ M. One day later, supernatant of the cultures was collected and a standard IFN-γ ELISA was performed. IFN-γ could be detected at high levels for wt-NY-ESO, irrespective of endoxifen treatment, and for iTCR-NY-ESO only after induction with Endoxifen (FIG. 9). These results show that iTCR-NY-ESO can be induced on the surface of PBL and has the same functional characteristics as the wt-NY-ESO TCR.

Figure 10:
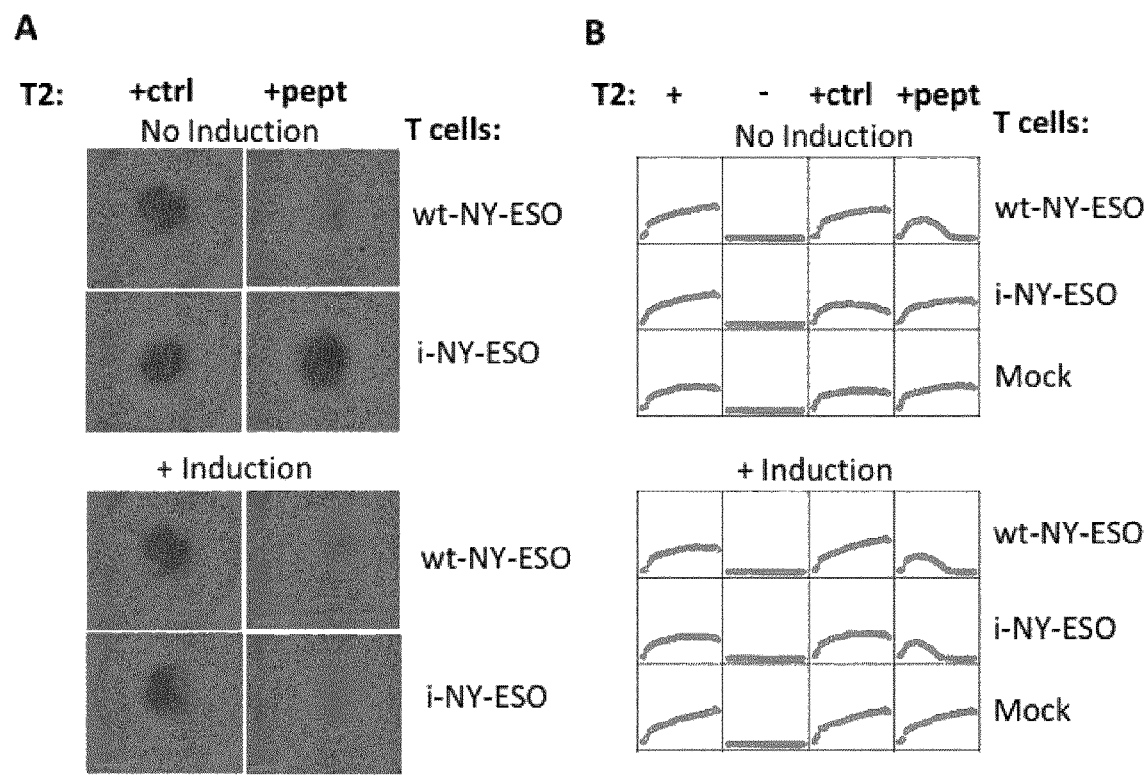
FIG. 10: CD8+ PBL transduced with i-NY-ESO (MHC-I restricted TCR) or CD8+ PBL expressing wt-NY-ESO were induced for 20 h with 10 μM Endoxifen (+induction) or left untreated (no induction). Cells were then incubated with T2 cells expressing NuclightRed loaded with relevant peptide (+pept) or with T2 NuclightRed cells loaded with irrelevant control peptide (+ctrl). Killing of T2 cells was followed over time using the Incucyte Zoom device. A) Pictures show 42 h after incubation of T cells and target cells. In the upper panel T cells were not induced with Endoxifen. Lower panel shows T cells that have been induced with Endoxifen. T2 NuclightRed cells appear in the middle and are dark grey. Effector cells are light grey. B) Graphs show density of T2 NuclightRed cells overtime (up to 42 h). Mock are untransduced CD8+PBL.

In a further experiment, it was found that T cells carrying i-TCR are cytotoxic and can eliminate targets. Again, CD8$^+$ PBL transduced with i-NY-ESO (MHC-I restricted TCR) or CD8$^+$ PBL expressing wt-NY-ESO were induced for 20 h with 10 μM Endoxifen (+induction) or left untreated (no induction). Cells were then incubated with T2 cells expressing NuclightRed loaded with relevant peptide (+pept) or with T2 NuclightRed cells loaded with irrelevant control peptide (+ctrl). Killing of T2 cells was followed over time using the Incucyte Zoom device. The pictures in FIG. 10A show 42h after incubation of T cells and target cells. In the upper panel T cells were not induced with Endoxifen. Lower panel shows T cells that have been induced with Endoxifen. T2 NuclightRed cells appear in the middle and are dark grey. Effector cells are light grey. In FIG. 10 B, graphs show density of T2 NuclightRed cells over time (up to 42h). In FIG. 10 the cells labelled Mock are untransduced CD8+ PBL.

Example 7

Testing for CD3 and TCR Expression in TCR−/− Cells Transduced with wt TCR and with TCR Carrying the Mutations K4V, N5P and Y37K in the Beta Chain (SEQ ID NO 4, See Table 2)

Figure 13:
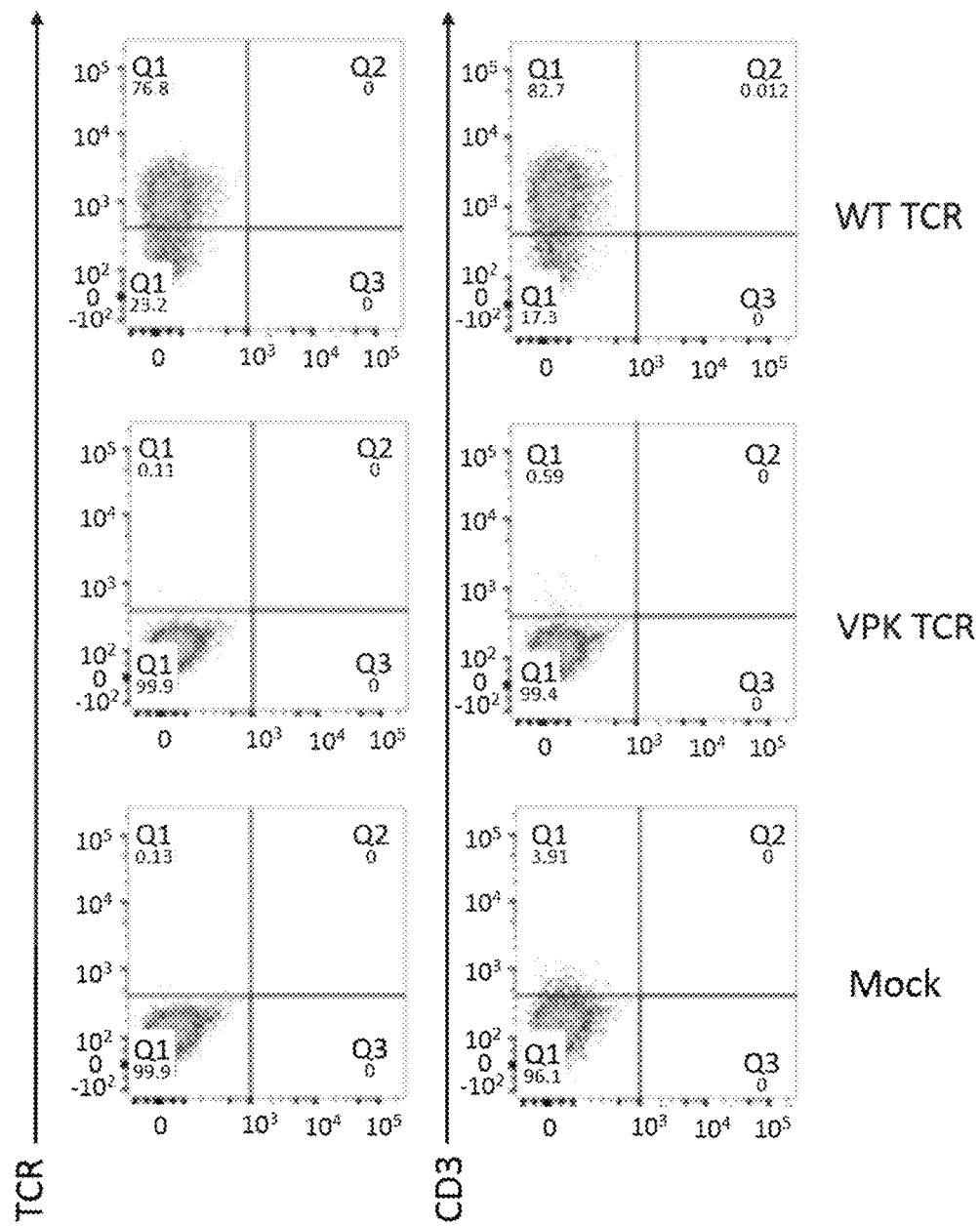
FIG. 13: TCR+ Jurkat-76 cells transduced with wt TCR recognizing PRAME antigen (wt TCR) and with TCR recognizing PRAME antigen with amino acid residues 4, 5, and 37 in the Constant beta chain (SEQ ID NO: 4) mutated, respectively to V, P and K. Mock control are Jurkat-76 TCR-/- cells untransduced. The cells were assessed for CD3 and TCR expression by flow cytometry. Plots were generated using the analysis tool FlowJo V10.

Jurkat-76 TCR−/− were transduced with wt TCR recognizing PRAME antigen (wt TCR) and with TCR recognizing PRAME carrying amino acid mutations K4V, N5P and Y37K in the Constant beta chain (SEQ ID NO:4). Mock control are Jurkat-76 TCR−/− cells untransduced. Flow cytometry was performed and cells were assessed for CD3 and TCR expression. Plots were generated using the analysis tool FlowJo V10. As can be seen from FIG. 13, the mutated TCR show no expression of CD3 and TCR, which shows that the mutated TCR cannot be expressed on the membrane.

Example 8

Mutations K4V, N5P and Y37K in the Beta Chain (SEQ ID NO 4, Table 2) Disrupt TCR Expression Which Can be Rescued by Dimerization of the Estrogen Receptors Contained in the C Terminus of the Alpha and Beta Constant Chains

Figure 14:
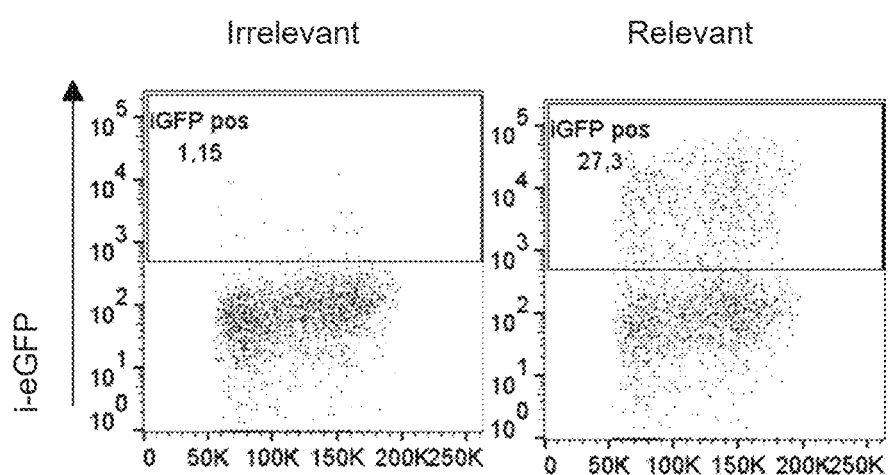
FIG. 14: TCR+ Jurkat-76 cells containing ieGFP reporter were transduced with G11-3 TCR carrying estrogen receptor in both C terminus of Constant alpha and beta chains and with amino acid residues 4, 5, and 37 in the Constant beta chain (SEQ ID NO: 4) mutated, respectively to V, P and K. Cells were induced with 1 μM endoxifen for 24 h. Cells were then incubated with LCL cells loaded either with relevant TDAWRFAMNYPRNPT (SEQ ID NO: 9) peptide (relevant) or with irrelevant PEVWILSPLLRHG (SEQ ID NO: 10) peptide (irrelevant). The ratio of LCL:Jurkat-76 in the cocultures was 1:1. Flow cytometry assessment of induced eGFP was performed 24 h after coincubation. Plots were generated using the analysis tool FlowJo V10.

Jurkat-76 containing ieGFP reporter were transduced with G11-3 TCR carrying estrogen receptor in both C terminus of Constant alpha and beta chains and with amino acid residues K4V, N5P and Y37K in the Constant beta chain (Seq ID 4, Table 2). Cells were induced with 1 μM endoxifen for 24 h. Cells were then incubated with LCL cells loaded either with irrelevant peptide or with relevant peptide. The ratio of LCL:Jurkat-76 in the cocultures was 1:1. Flow cytometry was performed 24 h after coincubation and cells were assessed for eGFP expression. Plots were generated using the analysis tool FlowJo V10. FIG. 14 shows that ieGFP was expressed in response to the relevant peptide. This reveals that TCR carrying mutations in the positions 4, 5 and 37 of the beta constant chain is still functional after Endoxifen-induced dimerization. Thus, amino acid in the positions 4, 5, and 37 in the Constant beta chain (SEQ ID 4) can be mutated without disturbing TCR-CD3 complex formation after dimerization induced by Endoxifen.

---

The invention claimed is:

1. A combination comprising one or more nucleic acid molecules, said one or more nucleic acid molecules comprising:
   (a) a nucleic acid sequence A, comprising
      (i) a nucleic acid sequence encoding an amino acid sequence being at least 90% identical to SEQ ID NO: 2 and optionally comprising at least one amino acid substitution compared to the amino acid sequence of SEQ ID NO: 2 selected from the group consisting of T44A and T47A, and
      (ii) a nucleic acid sequence encoding an inducible dimerization domain linked to, and downstream of, said nucleic acid sequence of (a)(i); and
   (b) a nucleic acid sequence B, comprising
      (i) a nucleic acid sequence encoding an amino acid sequence being at least 90% identical to SEQ ID NO: 4 and comprising at least one amino acid substitution compared to the amino acid sequence of SEQ ID NO: 4 selected from the group consisting of K4V, N5P, Y37K, L63A, S77A and R79A, and
      (ii) a nucleic acid sequence encoding an inducible dimerization domain linked to, and downstream of, said nucleic acid of (b)(ii), wherein said dimerization domain corresponds to the dimerization domain of (a)(ii),
   wherein said amino acid sequence of (a)(i) comprises at least one amino acid substitution compared to SEQ ID NO: 2.

2. The combination of claim 1, wherein the nucleic acid sequence A and the nucleic acid sequence B are comprised by separate nucleic acid molecules or comprised in one nucleic acid molecule.

3. The combination of claim 1, wherein
   (c) said nucleic acid sequence of (a)(i) encodes an amino acid sequence comprising two amino acid substitutions compared to the amino acid sequence of SEQ ID NO: 2, said two substitutions being T44A and T47A; and
   (d) said nucleic acid sequence of (b)(i) encodes an amino acid sequence comprising three amino acid substitutions compared to the amino acid sequence of SEQ ID NO: 4, wherein said three substitutions are K4V, N5P and Y37K, or said three substitutions are L63A, S77A, and R79A.

4. The combination of claim 1, wherein the dimerization domain is a homodimerization domain or a heterodimerization domain optionally selected from the group consisting of ERT2, FKBP, CalcineurinA (CNA), CyP-Fas, GyrB, GAI, GID1, eDHFR and FRB domain of mTOR.

5. An expression cassette system comprising:
   the combination of claim 1 as a single unitary expression cassette or
   the combination of claim 1 as first and second expression cassettes, wherein the first expression cassette comprises the nucleic acid sequence A and the second expression cassette comprises the nucleic acid sequence B.

6. A vector comprising the expression cassette system of claim 5.

7. The vector of claim 6, wherein the vector is a retroviral vector or a lentiviral vector.

8. A kit comprising:
   the combination of claim 1, and
   a dimerization agent corresponding to the dimerization domain encoded by the nucleic acid sequence (a)(ii) and the dimerization domain encoded by the nucleic acid sequence (b)(ii), said dimerization agent being capable of inducing dimerization of said dimerization domains.

9. The kit of claim 8, wherein the dimerization agent is selected from the group consisting of 4-hydroxytamoxifen, Endoxifen, 4-(1-[4-(Dimethylaminoethoxy) phenyl]-2-phenyl-1-butenyl) phenol, AP21967, 23,27-Epoxy-3H-pyrido [2,1-c][1,4]oxaazacyclohentriacontine, FK1012, FK506, FKCsA, Rapamycin, Coumermycin, Gibberellin.

10. A host cell comprising the combination of claim 1.

11. The host cell of claim 10, wherein the host cell is a T lymphocyte.

12. The host cell of claim 10, wherein said host cell comprises a dimerization agent corresponding to the dimerization domain encoded by the nucleic acid sequence (a) (ii) and the dimerization domain encoded by the nucleic acid sequence (b)(ii), said dimerization agent being capable of inducing dimerization of said dimerization domains.

13. The host cell of claim 12, wherein the dimerization agent is selected from the group consisting of 4-hydroxytamoxifen, Endoxifen, 4-(1-[4-(Dimethylaminoethoxy) phenyl]-2-phenyl-1-butenyl) phenol, AP21967, 23,27-Epoxy-3H-pyrido [2,1-c][1,4]oxaazacyclohentriacontine, FK1012, FK506, FKCsA, Rapamycin, Coumermycin, Gibberellin.

14. A protein encoded by the combination of claim 1.

15. A method for dimerizing a protein encoded by the combination of claim 1, comprising:
   combining a population of proteins encoded by nucleic acid sequence A and nucleic acid sequence B with a dimerization agent corresponding to the dimerization domain encoded by the nucleic acid sequence (a)(ii) and the dimerization domain encoded by the nucleic acid sequence (b)(ii), said dimerization agent being capable of inducing dimerization of said dimerization domains to said population of proteins.

16. A method for preparing an inducible T cell receptor, comprising:
   introducing the combination of claim 1 in vitro into a host cell under conditions allowing the expression of the protein encoded by nucleic acid sequence A and nucleic acid sequence B.

17. A method for the treatment of cancer, comprising administering the combination as defined in claim 1, the expression cassette system as defined in claim 5, the vector as defined in claim 6, the host cell as defined in claim 10, or the protein as defined in claim 8 to a subject in need thereof.

18. The method of claim 17, wherein said cancer is solid cancer or blood cancer.

19. A pharmaceutical composition comprising:
   the combination as defined in claim 1, the expression cassette system as defined in claim 6, the vector as defined in claim 6, the host cell as defined in claim 10, or the protein as defined in claim 14; and
   a pharmaceutically acceptable excipient.

* * * * *

SEQUENCE LISTING

<160> NUMBER OF SEQ ID NOS: 48

<210> SEQ ID NO 1
<211> LENGTH: 420
<212> TYPE: DNA
<213> ORGANISM: Homo sapiens

<400> SEQUENCE: 1

```
atccagaatc cggaccccgc cgtgtaccag ctgagagaca gcaagagcag cgacaagagt      60
gtgtgcctgt tcaccgactt cgactcccag accaacgtgt cccagagcaa ggacagcgac     120
gtgtacatca ccgacaagac cgtgctggac atgcggagca tggacttcaa gagcaacagc     180
gccgtggcct ggtccaacaa gagcgatttc gcctgcgcca acgccttcaa caacagcatt     240
atccccgagg acacattctt cccaagcccc gagagcagct gcgacgtgaa gctggtggaa     300
aagagcttcg agacagacac caacctgaat ttccagaacc tgagcgtgat cggcttcaga     360
atcctgctgc tgaaggtggc cggcttcaac ctgctgatga ccctgcggct gtggtccagc     420
```

<210> SEQ ID NO 2
<211> LENGTH: 140
<212> TYPE: PRT
<213> ORGANISM: Homo sapiens

<400> SEQUENCE: 2

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 3
<211> LENGTH: 537

```
<212> TYPE: DNA
<213> ORGANISM: Homo sapiens

<400> SEQUENCE: 3
gaagatctga agaacgtgtt cccccagag gtggccgtgt tcgagcctag cgaggccgag    60
atcagccaca cccagaaagc caccctcgtg tgcctggcca ccggcttcta tcccgaccac   120
gtggaactgt cttggtgggt caacggcaaa gaggtgcaca gcggcgtgtc caccgatccc   180
cagcctctga agaacagcc cgccctgaac gacagccggt actgcctgag cagccggctg   240
agagtgtccg ccaccttctg gcagaacccc cggaaccact tcagatgcca ggtgcagttc   300
tacggcctga gcgagaacga cgagtggacc caggacagag ccaagcccgt gacccagatc   360
gtgtctgccg aagcctgggg cagagccgat tgcggcttta ccagcgagag ctaccagcag   420
ggcgtgctga gcgccaccat cctgtacgag atcctgctgg gcaaggccac cctgtacgcc   480
gtgctggtgt ctgccctggt gctgatggct atggtcaagc ggaaggacag ccggggc      537

<210> SEQ ID NO 4
<211> LENGTH: 179
<212> TYPE: PRT
<213> ORGANISM: Homo sapiens

<400> SEQUENCE: 4

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 5
<211> LENGTH: 140
<212> TYPE: PRT
<213> ORGANISM: Artificial Sequence
<220> FEATURE:
<223> OTHER INFORMATION: Amino acid sequence of nucleic acid sequence A

<400> SEQUENCE: 5

Ile Gln Asn Pro Asp Pro Ala Val Tyr Gln Leu Arg Asp Ser Lys Ser
1               5                   10                  15
```

```
Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Ala Asp Lys Ala Val
        35                  40                  45

Leu Asp Met Arg Ser Met Asp Phe Lys Ser Asn Ser Ala Val Ala Trp
 50                  55                  60

Ser Asn Lys Ser Asp Phe Ala Cys Ala Asn Ala Phe Asn Asn Ser Ile
 65                  70                  75                  80

Ile Pro Glu Asp Thr Phe Phe Pro Ser Pro Glu Ser Ser Cys Asp Val
                 85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Lys Val Ala Gly
        115                 120                 125

Phe Asn Leu Leu Met Thr Leu Arg Leu Trp Ser Ser
130                 135                 140

<210> SEQ ID NO 6
<211> LENGTH: 179
<212> TYPE: PRT
<213> ORGANISM: Artificial Sequence
<220> FEATURE:
<223> OTHER INFORMATION: Amino acid sequence of nucleic acid sequence B

<400> SEQUENCE: 6

Glu Asp Leu Lys Asn Val Phe Pro Pro Glu Val Ala Val Phe Glu Pro
1               5                  10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Ala Lys
 50                  55                  60

Glu Gln Pro Ala Leu Asn Asp Ser Arg Tyr Cys Leu Ala Ser Ala Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 7
<211> LENGTH: 930
<212> TYPE: DNA
<213> ORGANISM: Artificial Sequence
<220> FEATURE:
<223> OTHER INFORMATION: ERT2

<400> SEQUENCE: 7
```

-continued

```
atgagagccg ccaatctgtg gcccagcccc ctgatgatca agcggagcaa gaagaactcc      60
ctggccctga gcctgaccgc cgaccagatg gtgtcagctc tgctggatgc cgagccccct     120
atcctgtaca gcgagtacga ccccacccgg ccttttagcg aggccagcat gatgggcctg     180
ctgaccaatc tggccgaccg cgagctggtg cacatgatca actgggccaa gcgggtgccc     240
ggcttcgtgg atctgacact gcacgaccag gtgcacctgc tggaatgcgc ctggctggaa     300
atcctgatga ttggcctcgt gtggcggagc atggaacacc ccgtgaagct gctgttcgcc     360
cccaacctgc tgctggaccg gaaccagggc aaatgcgtgg aaggcatggt ggaaatcttc     420
gacatgctgc tggccacctc cagccggttc agaatgatga acctgcaggg cgaagagttc     480
gtgtgtctga agtccatcat cctgctgaac agcggcgtgt acaccttcct gagcagcacc     540
ctgaagtccc tggaagagaa ggaccacatc accgggtgc tggacaagat caccgacacc     600
ctgatccacc tgatggctaa ggccggactg accctgcagc agcagcatca gagactggcc     660
cagctgctgc tgatcctgag ccacatccgg cacatgagca caagggaat ggaacatctg     720
tacagcatga agtgcaagaa cgtggtgccc ctgtacgatc tgctgctgga agccgccgat     780
gcccacagac tgcacgcccc tacatctaga ggcggagcca gcgtggaaga cagaccag      840
tctcacctgg ccagccgg ctccacaagc tctcacagcc tgcagaagta ctacatcacc      900
ggcgaggccg agggctttcc tgcaacagcc                                      930
```

<210> SEQ ID NO 8
<211> LENGTH: 310
<212> TYPE: PRT
<213> ORGANISM: Artificial Sequence
<220> FEATURE:
<223> OTHER INFORMATION: ERT2

<400> SEQUENCE: 8

```
Met Arg Ala Ala Asn Leu Trp Pro Ser Pro Leu Met Ile Lys Arg Ser
1               5                   10                  15

Lys Lys Asn Ser Leu Ala Leu Ser Leu Thr Ala Asp Gln Met Val Ser
            20                  25                  30

Ala Leu Leu Asp Ala Glu Pro Pro Ile Leu Tyr Ser Glu Tyr Asp Pro
        35                  40                  45

Thr Arg Pro Phe Ser Glu Ala Ser Met Met Gly Leu Leu Thr Asn Leu
    50                  55                  60

Ala Asp Arg Glu Leu Val His Met Ile Asn Trp Ala Lys Arg Val Pro
65                  70                  75                  80

Gly Phe Val Asp Leu Thr Leu His Asp Gln Val His Leu Leu Glu Cys
                85                  90                  95

Ala Trp Leu Glu Ile Leu Met Ile Gly Leu Val Trp Arg Ser Met Glu
            100                 105                 110

His Pro Val Lys Leu Leu Phe Ala Pro Asn Leu Leu Leu Asp Arg Asn
        115                 120                 125

Gln Gly Lys Cys Val Glu Gly Met Val Glu Ile Phe Asp Met Leu Leu
    130                 135                 140

Ala Thr Ser Ser Arg Phe Arg Met Met Asn Leu Gln Gly Glu Glu Phe
145                 150                 155                 160

Val Cys Leu Lys Ser Ile Ile Leu Leu Asn Ser Gly Val Tyr Thr Phe
                165                 170                 175

Leu Ser Ser Thr Leu Lys Ser Leu Glu Glu Lys Asp His Ile His Arg
            180                 185                 190

Val Leu Asp Lys Ile Thr Asp Thr Leu Ile His Leu Met Ala Lys Ala
```

```
                195                 200                 205
Gly Leu Thr Leu Gln Gln Gln His Gln Arg Leu Ala Gln Leu Leu Leu
    210                 215                 220

Ile Leu Ser His Ile Arg His Met Ser Asn Lys Gly Met Glu His Leu
225                 230                 235                 240

Tyr Ser Met Lys Cys Lys Asn Val Val Pro Leu Tyr Asp Leu Leu Leu
                245                 250                 255

Glu Ala Ala Asp Ala His Arg Leu His Ala Pro Thr Ser Arg Gly Gly
            260                 265                 270

Ala Ser Val Glu Glu Thr Asp Gln Ser His Leu Ala Thr Ala Gly Ser
        275                 280                 285

Thr Ser His Ser Leu Gln Lys Tyr Tyr Ile Thr Gly Glu Ala Glu
    290                 295                 300

Gly Phe Pro Ala Thr Ala
305                 310

<210> SEQ ID NO 9
<211> LENGTH: 15
<212> TYPE: PRT
<213> ORGANISM: Artificial Sequence
<220> FEATURE:
<223> OTHER INFORMATION: relevant "TDA" peptide

<400> SEQUENCE: 9

Thr Asp Ala Trp Arg Phe Ala Met Asn Tyr Pro Arg Asn Pro Thr
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: irrelevant "PEV" peptide

<400> SEQUENCE: 10

Pro Glu Val Trp Ile Leu Ser Pro Leu Leu Arg His Gly
1               5                   10

<210> SEQ ID NO 11
<211> LENGTH: 9
<212> TYPE: PRT
<213> ORGANISM: Artificial Sequence
<220> FEATURE:
<223> OTHER INFORMATION: irrelevant T2 peptide

<400> SEQUENCE: 11

Val Leu Asp Gly Leu Asp Val Leu Leu
1               5

<210> SEQ ID NO 12
<211> LENGTH: 9
<212> TYPE: PRT
<213> ORGANISM: Artificial Sequence
<220> FEATURE:
<223> OTHER INFORMATION: relevant T2 peptide

<400> SEQUENCE: 12

Ser Leu Leu Met Trp Ile Thr Gln Cys
1               5

<210> SEQ ID NO 13
<211> LENGTH: 48
<212> TYPE: DNA
```

<213> ORGANISM: Homo sapiens

<400> SEQUENCE: 13
aatatccaga accctgaccc tgccgtgtac cagctgagag actctaaa    48

<210> SEQ ID NO 14
<211> LENGTH: 42
<212> TYPE: DNA
<213> ORGANISM: Homo sapiens

<400> SEQUENCE: 14
tccagtgaca agtctgtctg cctattcacc gattttgatt ct    42

<210> SEQ ID NO 15
<211> LENGTH: 30
<212> TYPE: DNA
<213> ORGANISM: Homo sapiens

<400> SEQUENCE: 15
caaacaaatg tgtcacaaag taaggattct    30

<210> SEQ ID NO 16
<211> LENGTH: 42
<212> TYPE: DNA
<213> ORGANISM: Homo sapiens

<400> SEQUENCE: 16
gatgtgtata tcacagacaa aactgtgcta gacatgaggt ct    42

<210> SEQ ID NO 17
<211> LENGTH: 45
<212> TYPE: DNA
<213> ORGANISM: Homo sapiens

<400> SEQUENCE: 17
atggacttca agagcaacag tgctgtggcc tggagcaaca aatct    45

<210> SEQ ID NO 18
<211> LENGTH: 30
<212> TYPE: DNA
<213> ORGANISM: Homo sapiens

<400> SEQUENCE: 18
gactttgcat gtgcaaacgc cttcaacaac    30

<210> SEQ ID NO 19
<211> LENGTH: 37
<212> TYPE: DNA
<213> ORGANISM: Homo sapiens

<400> SEQUENCE: 19
agcattattc cagaagacac cttcttcccc agcccag    37

<210> SEQ ID NO 20
<211> LENGTH: 16
<212> TYPE: PRT
<213> ORGANISM: Homo sapiens
<220> FEATURE:
<221> NAME/KEY: SITE
<222> LOCATION: (16)..(16)
<223> OTHER INFORMATION: This residue is linked C-terminally to a peptide having the amino acid sequence as shown in SEQ ID NO: 21 and a gap of 6 positions in length

<400> SEQUENCE: 20

Asn Ile Gln Asn Pro Asp Pro Ala Val Tyr Gln Leu Arg Asp Ser Lys
1               5                   10                  15

<210> SEQ ID NO 21
<211> LENGTH: 14
<212> TYPE: PRT
<213> ORGANISM: Homo sapiens
<220> FEATURE:
<221> NAME/KEY: SITE
<222> LOCATION: (14)..(14)
<223> OTHER INFORMATION: This residue is linked C-terminally to a
      peptide having the amino acid sequence as shown in SEQ ID NO: 22
      and a gap of 3 positions in length

<400> SEQUENCE: 21

Ser Ser Asp Lys Ser Val Cys Leu Phe Thr Asp Phe Asp Ser
1               5                   10

<210> SEQ ID NO 22
<211> LENGTH: 10
<212> TYPE: PRT
<213> ORGANISM: Homo sapiens
<220> FEATURE:
<221> NAME/KEY: SITE
<222> LOCATION: (10)..(10)
<223> OTHER INFORMATION: This residue is linked C-terminally to a
      peptide having the amino acid sequence as shown in SEQ ID NO: 23
      and a gap of 7 positions in length

<400> SEQUENCE: 22

Gln Thr Asn Val Ser Gln Ser Lys Asp Ser
1               5                   10

<210> SEQ ID NO 23
<211> LENGTH: 14
<212> TYPE: PRT
<213> ORGANISM: Homo sapiens
<220> FEATURE:
<221> NAME/KEY: SITE
<222> LOCATION: (14)..(14)
<223> OTHER INFORMATION: This residue is linked C-terminally to a
      peptide having the amino acid sequence as shown in SEQ ID NO: 24
      and a gap of 2 positions in length

<400> SEQUENCE: 23

Asp Val Tyr Ile Thr Asp Lys Thr Val Leu Asp Met Arg Ser
1               5                   10

<210> SEQ ID NO 24
<211> LENGTH: 15
<212> TYPE: PRT
<213> ORGANISM: Homo sapiens
<220> FEATURE:
<221> NAME/KEY: SITE
<222> LOCATION: (15)..(15)
<223> OTHER INFORMATION: This residue is linked C-terminally to a
      peptide having the amino acid sequence as shown in SEQ ID NO: 25
      and a gap of 9 positions in length

<400> SEQUENCE: 24

Met Asp Phe Lys Ser Asn Ser Ala Val Ala Trp Ser Asn Lys Ser
1               5                   10                  15

<210> SEQ ID NO 25
<211> LENGTH: 10
<212> TYPE: PRT
<213> ORGANISM: Homo sapiens
<220> FEATURE:
<221> NAME/KEY: SITE

```
<222> LOCATION: (10)..(10)
<223> OTHER INFORMATION: This residue is linked C-terminally to a
      peptide having the amino acid sequence as shown in SEQ ID NO: 26
      and a gap of 2 positions in length

<400> SEQUENCE: 25

Asp Phe Ala Cys Ala Asn Ala Phe Asn Asn
1               5                   10

<210> SEQ ID NO 26
<211> LENGTH: 12
<212> TYPE: PRT
<213> ORGANISM: Homo sapiens

<400> SEQUENCE: 26

Ser Ile Ile Pro Glu Asp Thr Phe Phe Pro Ser Pro
1               5                   10

<210> SEQ ID NO 27
<211> LENGTH: 45
<212> TYPE: DNA
<213> ORGANISM: Homo sapiens

<400> SEQUENCE: 27
aaagttcctg tgatgtcaag ctggtcgaga aaagctttga aacag            45

<210> SEQ ID NO 28
<211> LENGTH: 15
<212> TYPE: PRT
<213> ORGANISM: Homo sapiens

<400> SEQUENCE: 28

Glu Ser Ser Cys Asp Val Lys Leu Val Glu Lys Ser Phe Glu Thr
1               5                   10                  15

<210> SEQ ID NO 29
<211> LENGTH: 108
<212> TYPE: DNA
<213> ORGANISM: Homo sapiens

<400> SEQUENCE: 29
atacgaacct aaactttcaa aacctgtcag tgattgggtt ccgaatcctc ctcctgaaag      60
tggccgggtt taatctgctc atgacgctgc ggctgtggtc cagctgag                 108

<210> SEQ ID NO 30
<211> LENGTH: 35
<212> TYPE: PRT
<213> ORGANISM: Homo sapiens

<400> SEQUENCE: 30

Asp Thr Asn Leu Asn Phe Gln Asn Leu Ser Val Ile Gly Phe Arg Ile
1               5                   10                  15

Leu Leu Leu Lys Val Ala Gly Phe Asn Leu Leu Met Thr Leu Arg Leu
                20                  25                  30

Trp Ser Ser
        35

<210> SEQ ID NO 31
<211> LENGTH: 69
<212> TYPE: DNA
<213> ORGANISM: Homo sapiens

<400> SEQUENCE: 31
```

```
gaggacctga caaggtgtt cccacccgag gtcgctgtgt ttgagccatc agaagcagag    60
atctcccac                                                          69
```

<210> SEQ ID NO 32
<211> LENGTH: 45
<212> TYPE: DNA
<213> ORGANISM: Homo sapiens

<400> SEQUENCE: 32

```
acccaaaagg ccacactggt gtgcctggcc acaggcttct tcccc                  45
```

<210> SEQ ID NO 33
<211> LENGTH: 48
<212> TYPE: DNA
<213> ORGANISM: Homo sapiens

<400> SEQUENCE: 33

```
gaccacgtgg agctgagctg gtgggtgaat gggaaggagg tgcacagt               48
```

<210> SEQ ID NO 34
<211> LENGTH: 45
<212> TYPE: DNA
<213> ORGANISM: Homo sapiens

<400> SEQUENCE: 34

```
ggggtcagca cggacccgca gcccctcaag gagcagcccg ccctc                  45
```

<210> SEQ ID NO 35
<211> LENGTH: 57
<212> TYPE: DNA
<213> ORGANISM: Homo sapiens

<400> SEQUENCE: 35

```
aatgactcca gatactgcct gagcagccgc ctgagggtct cggccacctt ctggcag     57
```

<210> SEQ ID NO 36
<211> LENGTH: 124
<212> TYPE: DNA
<213> ORGANISM: Homo sapiens

<400> SEQUENCE: 36

```
aaccccgca accacttccg ctgtcaagtc cagttctacg ggctctcgga gaatgacgag   60
tggacccagg atagggccaa acccgtcacc cagatcgtca gcgccgaggc ctggggtaga  120
gcag                                                              124
```

<210> SEQ ID NO 37
<211> LENGTH: 23
<212> TYPE: PRT
<213> ORGANISM: Homo sapiens
<220> FEATURE:
<221> NAME/KEY: SITE
<222> LOCATION: (23)..(23)
<223> OTHER INFORMATION: This residue is linked C-terminally to a
      peptide having the amino acid sequence as shown in SEQ ID NO: 38
      and a gap of 2 positions in length

<400> SEQUENCE: 37

```
Glu Asp Leu Asn Lys Val Phe Pro Pro Glu Val Ala Val Phe Glu Pro
1               5                   10                  15

Ser Glu Ala Glu Ile Ser His
            20
```

```
<210> SEQ ID NO 38
<211> LENGTH: 15
<212> TYPE: PRT
<213> ORGANISM: Homo sapiens
<220> FEATURE:
<221> NAME/KEY: SITE
<222> LOCATION: (15)..(15)
<223> OTHER INFORMATION: This residue is linked C-terminally to a
      peptide having the amino acid sequence as shown in SEQ ID NO: 39
      and a gap of 2 positions in length

<400> SEQUENCE: 38

Thr Gln Lys Ala Thr Leu Val Cys Leu Ala Thr Gly Phe Phe Pro
1               5                   10                  15

<210> SEQ ID NO 39
<211> LENGTH: 16
<212> TYPE: PRT
<213> ORGANISM: Homo sapiens
<220> FEATURE:
<221> NAME/KEY: SITE
<222> LOCATION: (16)..(16)
<223> OTHER INFORMATION: This residue is linked C-terminally to a
      peptide having the amino acid sequence as shown in SEQ ID NO: 40
      and a gap of 2 positions in length

<400> SEQUENCE: 39

Asp His Val Glu Leu Ser Trp Trp Val Asn Gly Lys Glu Val His Ser
1               5                   10                  15

<210> SEQ ID NO 40
<211> LENGTH: 15
<212> TYPE: PRT
<213> ORGANISM: Homo sapiens
<220> FEATURE:
<221> NAME/KEY: SITE
<222> LOCATION: (15)..(15)
<223> OTHER INFORMATION: This residue is linked C-terminally to a
      peptide having the amino acid sequence as shown in SEQ ID NO: 41
      and a gap of 1 position in length

<400> SEQUENCE: 40

Gly Val Ser Thr Asp Pro Gln Pro Leu Lys Glu Gln Pro Ala Leu
1               5                   10                  15

<210> SEQ ID NO 41
<211> LENGTH: 19
<212> TYPE: PRT
<213> ORGANISM: Homo sapiens
<220> FEATURE:
<221> NAME/KEY: SITE
<222> LOCATION: (19)..(19)
<223> OTHER INFORMATION: This residue is linked C-terminally to a
      peptide having the amino acid sequence as shown in SEQ ID NO: 42
      and a gap of 1 position in length

<400> SEQUENCE: 41

Asn Asp Ser Arg Tyr Cys Leu Ser Ser Arg Leu Arg Val Ser Ala Thr
1               5                   10                  15

Phe Trp Gln

<210> SEQ ID NO 42
<211> LENGTH: 41
<212> TYPE: PRT
<213> ORGANISM: Homo sapiens

<400> SEQUENCE: 42

Asn Pro Arg Asn His Phe Arg Cys Gln Val Gln Phe Tyr Gly Leu Ser
1               5                   10                  15
```

Glu Asn Asp Glu Trp Thr Gln Asp Arg Ala Lys Pro Val Thr Gln Ile
            20                  25                  30

Val Ser Ala Glu Ala Trp Gly Arg Ala
        35                  40

<210> SEQ ID NO 43
<211> LENGTH: 19
<212> TYPE: DNA
<213> ORGANISM: Homo sapiens

<400> SEQUENCE: 43
gactgtggct ttacctcgg                                              19

<210> SEQ ID NO 44
<211> LENGTH: 6
<212> TYPE: PRT
<213> ORGANISM: Homo sapiens

<400> SEQUENCE: 44

Asp Cys Gly Phe Thr Ser
1               5

<210> SEQ ID NO 45
<211> LENGTH: 108
<212> TYPE: DNA
<213> ORGANISM: Homo sapiens

<400> SEQUENCE: 45
gtgtcctacc agcaaggggt cctgtctgcc accatcctct atgagatcct gctagggaag      60
gccaccctgt atgctgtgct ggtcagcgcc cttgtgttga tggccatg                 108

<210> SEQ ID NO 46
<211> LENGTH: 36
<212> TYPE: PRT
<213> ORGANISM: Homo sapiens

<400> SEQUENCE: 46

Val Ser Tyr Gln Gln Gly Val Leu Ser Ala Thr Ile Leu Tyr Glu Ile
1               5                   10                  15

Leu Leu Gly Lys Ala Thr Leu Tyr Ala Val Leu Val Ser Ala Leu Val
            20                  25                  30

Leu Met Ala Met
        35

<210> SEQ ID NO 47
<211> LENGTH: 18
<212> TYPE: DNA
<213> ORGANISM: Homo sapiens

<400> SEQUENCE: 47
gtcaagagaa aggatttc                                               18

<210> SEQ ID NO 48
<211> LENGTH: 6
<212> TYPE: PRT
<213> ORGANISM: Homo sapiens

<400> SEQUENCE: 48

Val Lys Arg Lys Asp Phe
1               5